United States Patent [19]
Daub et al.

[11] Patent Number: 5,268,388
[45] Date of Patent: Dec. 7, 1993

[54] SUBSTITUTED SEMICARBAZONE ARTHROPODICIDES

[75] Inventors: John P. Daub; George P. Lahm, both of Wilmington, Del.; Bradford S. Marlin, Cochranville, Pa.

[73] Assignee: E. I. Du Pont de Nemours and Company, Wilmington, Del.

[21] Appl. No.: 971,008

[22] Filed: Nov. 2, 1992

Related U.S. Application Data

[60] Division of Ser. No. 689,042, May 20, 1991, Pat. No. 5,182,303, which is a continuation-in-part of Ser. No. 436,361, Nov. 13, 1989, abandoned, which is a continuation-in-part of Ser. No. 290,404, Dec. 27, 1988, abandoned.

[51] Int. Cl.$^5$ ............... A61K 31/34; A61K 31/38; C07D 367/82; C07D 333/66
[52] U.S. Cl. ............... 514/470; 514/80; 514/96; 514/100; 514/415; 514/443; 544/143; 546/196; 548/483; 548/111; 549/53; 549/55; 549/57; 549/466; 549/467; 549/6; 549/220
[58] Field of Search ............... 549/53, 55, 57, 466, 549/467, 6, 220, 113; 548/983; 544/143; 546/196; 514/80, 96, 100, 415, 443, 470

[56] References Cited

U.S. PATENT DOCUMENTS

| | | | |
|---|---|---|---|
| 4,547,524 | 10/1985 | Kaneko | 514/594 |
| 4,593,027 | 6/1986 | Mulder et al. | 564/36 |

FOREIGN PATENT DOCUMENTS

| | | |
|---|---|---|
| 3913 | 9/1979 | European Pat. Off. |
| 26646 | 4/1981 | European Pat. Off. |
| 254461 | 1/1988 | European Pat. Off. |
| 8800197 | 1/1988 | PCT Int'l Appl. |

OTHER PUBLICATIONS

J. Indian Chem. Soc., 37, pp. 443–450 (1966).
Misra et al., J. Indian Chem. Soc., 52(10) pp. 981–982 (1975), Chem. Abst. vol. 84, 73957m (1976).
Landquist, J. Chem. Soc. (C), pp. 63–66 (1970).
Treibs et al., Berichte, 86(5), pp. 616–625 (1953).

*Primary Examiner*—Bernard Dentz
*Attorney, Agent, or Firm*—James A. Costello

[57] ABSTRACT

Certain substituted semicarbazones, including all geometric and stereoisomers thereof, agricultural compositions containing them and their use as arthropodicides.

8 Claims, No Drawings

SUBSTITUTED SEMICARBAZONE ARTHROPODICIDES

This is a division of application Ser. No. 07/689,042, filed May 20, 1991, now U.S. Pat. No. 5,182,303, which is a continuation-in-part of application Ser. No. 07/436,361, filed on Nov. 13, 1989, now abandoned, which was a continuation-in-part of U.S. Ser. No. 07/290,404, filed Dec. 27, 1988, now abandoned.

BACKGROUND OF THE INVENTION

U.S. Pat. No. 4,547,524 discloses benzoyl hydrazone derivatives as insecticides.

WO 8800197 discloses as part of a broader scope substituted semicarbazones derived from chromanones and thiochromanones as intermediates used in the preparation of insecticides.

EP-3,913 discloses substituted benzophenone hydrazones to be useful as insecticides.

EP-26,040 discloses a broad scope of substituted hydrazones to be useful as insecticides.

EP-254,461 discloses N-substituted hydrazones to be useful as insecticides.

GB-A-1,374,725 discloses structurally related semicarbazide insecticides.

J. Ind. Chem. Soc. 37, pages 443 to 50 (1960) discloses a compound of the formula:

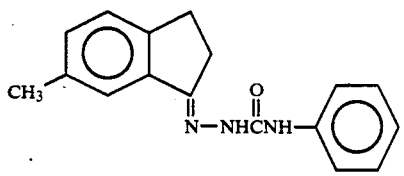

but no utility therefor.

SUMMARY OF THE INVENTION

This invention pertains to compounds of Formula I, including all geometric isomers, stereoisomers, and agronomically and nonagronomically suitable salts thereof, compositions containing them, and their use as agronomic and nonagronomic arthropodicides:

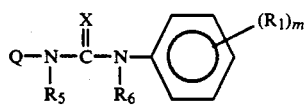    I wherein:
Q is

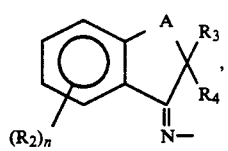    Q-1

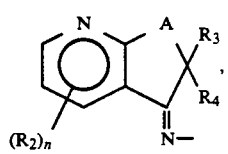    Q-2

-continued

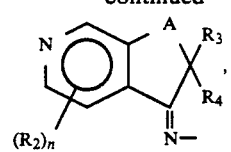    Q-3

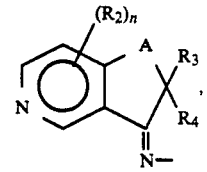    Q-4

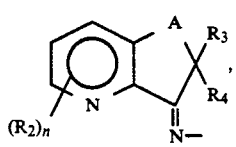    Q-5

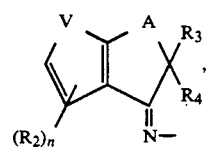    Q-6

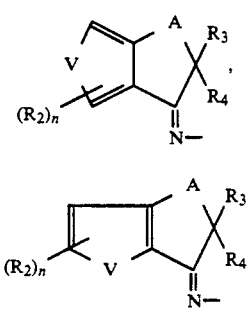    Q-7

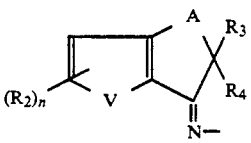    Q-8

A is $(CH_2)_t$, O, $S(O)_q$, $NR_7$, $OCH_2$ or $S(O)_qCH_2$, wherein, each carbon individually can be substituted with 1 to 2 substituents selected from 1 to 2 halogen, $C_1$-$C_6$ alkyl, $C_3$-$C_6$ cycloalkyl, $C_3$-$C_6$ halocycloalkyl, $C_4$-$C_7$ alkylcycloalkyl, $C_2$-$C_4$ alkoxycarbonyl, or phenyl optionally substituted with 1 to 3 substituent independently selected from W;

$R_1$ and $R_2$ are independently $R_8$, halogen, CN, $NO_2$, $N_3$, SCN, $OR_8$, $SR_8$, $SOR_8$, $SO_2R_8$, $NR_8R_9$, $C(O)R_8$, $CO_2R_8$, $C(O)NR_8R_9$, $OC(O)R_8$, $OCO_2R_8$, $OC(O)NR_8R_9$, $NR_9C(O)R_8$, $NR_9C(O)NR_8R_9$, $OSO_2R_8$, $NR_9SO_2R_8$, or when m is 2, $R_1$ is optionally taken together to form a 5 or 6 membered fused ring as $OCH_2O$, $OCH_2CH_2O$ OR $CH_2CH_2O$ each of which is optionally substituted with 1 to 4 halogen atoms or 1 to 2 methyl groups, or when n is 2, $R_2$ is optionally taken together to form a 5 or 6 membered fused ring as $OCH_2O$, $OCH_2CH_2O$ or $CH_2CH_2O$ each of which can be substituted 1 to 4 halogens or 1 to 2 methyl groups; $R_2$ being other than $CH_3$ when $R_1$, $R_3$ and $R_4$ are H and A is $CH_2$;

$R_3$ is H, $C_1$-$C_6$ alkyl, $C_1$-$C_6$ haloalkyl, $C_4$-$C_6$ alkylcycloalkyl, $C_2$-$C_6$ alkenyl, $C_2$-$C_6$ haloalkenyl, $C_2$-$C_6$ alkynyl, $C_2$-$C_6$ haloalkynyl, $C_2$-$C_6$ alkoxyalkyl, $C_2$-$C_6$ cyanoalkyl, $C_3$-$C_8$ alkoxycarbonylalkyl, $OR_8$, $S(O)_qR_8$, $NR_8R_9$, CN, $CO_2R_8$, $C(O)R_8$, $C(O)NR_8R_9$, $C(S)NR_8R_9$, $C(S)R_8$, $C(S)SR_8$, phenyl optionally substituted with $(R_{10})_p$ or benzyl optionally substituted with 1 to 3 substituents independently selected from W or $R_3$ is $C_3$-$C_6$ cycloalkyl optionally substituted with 1 to 2 halogens or 1 to 2 $CH_3$;

$R_4$ is H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_2$-$C_6$ alkoxyalkyl, $C_2$-$C_6$ cyanoalkyl, phenyl optionally substituted with $(R_{10})_p$ or benzyl optionally substituted with 1 to 3 substituents independently selected from W;

$R_5$ and $R_6$ are independently H, $C_1$-$C_{22}$ alkyl, $C_2$-$C_{22}$ alkoxyalkyl, $C_2$-$C_{22}$ alkylcarbonyl, $C_2$-$C_{22}$ alkoxycarbonyl, $C_2$-$C_{22}$ haloalkyl carbonyl, $C_2$-$C_{22}$ haloalkoxycarbonyl, $SR_{11}$, CHO, $C_1$-$C_4$ alkylsulfonyl, phenylsulfonyl optionally substituted with 1 to 3 substituents independently selected from W; $C_7$-$C_{15}$ phenoxycarbonyl optionally substituted with 1 to 3 substituents selected from W; $C_7$-$C_{15}$ phenylcarbonyl optionally substituted with 1 to 3 substituents independently selected from W; $C(O)CO_2C_1$ to $C_4$ alkyl, $C_8$-$C_{12}$ benzyloxycarbonyl optionally substituted with 1 to 3 substituents independently selected from W; or $R_5$ and $R_6$ are independently phenyl optionally substituted with 1 to 3 substituents independently selected from W, or benzyl optionally substituted with 1 to 3 substituents independently selected from W;

$R_7$ is H, $C_1$-$C_4$ alkyl or phenyl optionally substituted with W; $SR_8$, $SOR_8$, $SO_2R_8$, $C(O)R_8$, $CO_2R_8$, $C(O)NR_8R_9$, $C(S)NR_8R_9$, $C(S)R_8$, $C(S)OR_8$, $P(O)(OR_8)_2$, $P(S)(OR_8)_2$, $P(O)(R_8)OR_8$ or $P(O)(R_8)SR_8$; provided that when $R_7$ is other than $COR_8$, $C(O)NR_8R_9$ or $C(S)NR_8R_9$ then $R_8$ is other than H;

$R_8$ is H, $C_1$-$C_6$ alkyl, $C_1$-$C_6$ haloalkyl, $C_4$-$C_7$ cycloalkylalkyl halocycloalkylalkyl $C_2$-$C_6$ alkenyl, $C_2$-$C_6$ haloalkenyl, $C_2$-$C_6$ alkynyl, $C_2$-$C_6$ haloalkynyl, $C_2$-$C_6$ alkoxyalkyl, $C_2$-$C_6$ alkylthioalkyl, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, phenyl optionally substituted with 1 to 3 substituents independently selected from W or benzyl optionally substituted with 1 to 3 substituents independently selected from W;

$R_9$ is H, $C_1$-$C_4$ alkyl, $C_2$-$C_4$ alkenyl, $C_2$-$C_4$ alkynyl, or $R_8$ and $R_9$ is optionally taken together as $(CH_2)_4$, $(CH_2)_5$ or $(CH_2CH_2OCH_2CH_2)$;

$R_{10}$ is $R_8$, halogen, CN, $NO_2$, $N_3$, SCN, $OR_8$, $SR_8$, $SOR_8$, $SO_2R_8$, $NR_8R_9$, $COR_8$, $CO_2R_8$, $CONR_8R_9$, $SO_2NR_8R_9$, $OC(O)R_8$, $OCO_2R_8$, $OC(O)NR_8R_9$, $NR_9C(O)R_8$, $NR_9C(O)NR_8R_9$, $OSO_2R_8$, $NR_9SO_2R_8$ or when p is 2, $R_{10}$ is optionally taken together to form a 5 or 6 membered fused ring as $OCH_2O$, $OCH_2CH_2O$, or $CH_2CH_2O$ each of which is optionally substituted with independently, 1 to 4 halogen atoms or 1 to 2 methyl groups;

$R_{11}$ is $C_1$-$C_{22}$ alkyl, $C_1$-$C_{22}$ haloalkyl, phenyl optionally substituted with 1 to 3 substituents independently selected from W, or $R_{11}$ is $NR_{12}C(O)R_{13}$, $NR_{12}S(O)_aR_{13}$, $C(O)R_{13}$, $NR_{12}R_{16}$, $SR_{14}$,

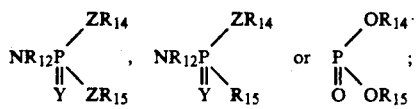

$R_{12}$ and $R_{16}$ are independently selected from $C_1$-$C_6$ alkyl, $C_1$-$C_6$ haloalkyl, $C_3$-$C_6$ cycloalkyl, $C_4$-$C_7$ cycloalkylalkyl, $C_2$-$C_6$ cyanoalkyl, $C_2$-$C_6$ alkoxyalkyl, $C_3$-$C_8$ alkoxycarbonylalkyl, $C_4$-$C_8$ dialkylaminocarbonylalkyl, phenyl optionally substituted by 1 to 2 substituents selected from W, benzyl optionally substituted by 1 to 2 substituents selected from W and phenethyl optionally substituted by 1 to 2 substituents selected from W, or $R_{12}$-$R_{16}$ is optionally taken together as $(CH_2)_4$, $(CH_2)_5$ or $(CH_2)_2O(CH_2)_2$, each ring optionally substituted with 1 to 2 $CH_3$;

$R_{13}$ is F, $C_1$-$C_{20}$ alkyl, $C_1$-$C_6$ haloalkyl, $C_2$-$C_8$ dialkylamino, piperidinyl, pyrrolidinyl, morpholinyl, phenyl optionally substituted with 1 to 3 substituents selected from W, or $R_{13}$ is $C_1$-$C_{20}$ alkoxy $C_1$-$C_6$ haloalkoxy or $C_1$-$C_4$ alkoxy substituted with cyano, nitro, $C_1$-$C_4$ alkoxy, $C_4$-$C_8$ alkoxyalkoxy, $C_1$-$C_2$ alkylthio, $C_2$-$C_3$ alkoxycarbonyl, $C_3$-$C_5$ dialkylaminocarbonyl or phenyl optionally substituted with 1 to 3 substituents independently selected from W, or $R_{13}$ is phenoxy optionally substituted with 1 to 3 substituents selected from W;

$R_{14}$ and $R_{15}$ are independently selected from $C_1$-$C_4$ alkyl, $C_2$-$C_4$ haloalkyl, phenyl optionally substituted with 1 to 3 substituents independently selected from W or $R_{14}$ and $R_{15}$ is optionally taken together as $(CH_2)_2$, $(CH_2)_3$ or $CH_2C(CH_3)_2CH_2$;

W is halogen, CN, $NO_2$, $C_1$-$C_2$ alkyl, $C_1$-$C_2$ haloalkyl, $C_1$-$C_2$ alkoxy, $C_1$-$C_2$ haloalkoxy, $C_1$-$C_2$ alkylthio, $C_1$-$C_2$ haloalkylthio, $C_1$-$C_2$ alkylsulfonyl or $C_1$-$C_2$ haloalkylsulfonyl;

m is 1 to 5;
n is 1 to 4;
t is 0 to 3;
q is 0 to 2;
p is 1 to 3;
a is 0 to 2;
V is O or S;
X is O or S; X being O when A is $CH_2$ and $R_2$, $R_3$ and $R_4$ are H;
Y is O or S; and
Z is O or S.

Preferred Compounds (A) are those compounds of Formula I wherein;

when $R_3$ or $R_4$ is H and A is oxygen then the remaining $R_3$ or $R_4$ is other than phenyl or phenyl optionally substituted with W and when t is 0 then $R_3$ or $R_4$ are other than Ph or phenyl optionally substituted with W.

Preferred Compounds (B) are Compounds of Formula I wherein;

$R_1$, $R_2$ and $R_{10}$ are $R_8$, halogen, CN, $NO_2$, $OR_8$, $SR_8$, $SOR_8$, $SO_2R_8$, $NR_8R_9$, $CO_2R_8$, $SO_2NR_8R_9$, or when m, n or q is 2, then $R_1$, $R_2$ or $R_{10}$ respectively is optionally taken together to form a 5 or 6 membered fused ring as $OCH_2O$, $OCH_2CH_2O$ or $CH_2CH_2O$ each of which is optionally substituted with 1 to 4 halogens or 1 to 2 methyl groups;

$R_8$ is H, $C_1$-$C_6$ alkyl, $C_1$-$C_6$ haloalkyl, $C_3$-$C_6$ cycloalkylalkyl, $C_3$-$C_6$ halocycloalkylalkyl, $C_2$-$C_6$ alkenyl, $C_2$-$C_6$ haloalkenyl, $C_2$-$C_6$ alkynyl, $C_3$-$C_6$ cycloalkyl, phenyl optionally substituted with 1 to 2 substituents independently selected from W or benzyl optionally substituted with 1 to 2 substituents independently selected from W;

$R_5$ and $R_6$ are independently H, $C_1$-$C_3$ alkyl, $C_2$-$C_4$ alkylcarbonyl, $C_2$-$C_4$ alkoxycarbonyl, CHO, $SR_{11}$, phenyl optionally substituted with 1 to 2 substituents independently selected from W, or benzyl optionally substituted with 1 to 2 substituents independently selected from W;

$R_{11}$ is $C_1$-$C_3$ alkyl, phenyl optionally substituted with 1 to 2 substituents independently selected from W, $NR_{12}C(O)R_{13}$, $NR_{12}S(O)_aR_{13}$, $C(O)R_{13}$, $NR_{12}R_{16}$;

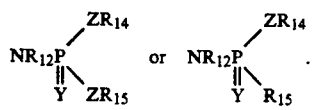

$R_{12}$ and $R_{16}$ are independently selected from $C_1$-$C_6$ alkyl, $C_1$-$C_6$ haloalkyl, $C_5$-$C_6$ cycloalkyl, $C_3$-$C_8$ alkoxycarbonylalkyl, phenyl, benzyl and phenethyl or each phenyl, benzyl and phenethyl optionally substituted with 1 to 2 substituents independently selected from W, or $R_{12}$ and $R_{16}$ can be taken together as $(CH_2)_4$, $(CH_2)_5$ or $(CH_2)_2O(CH_2)_2$;

$R_{14}$ and $R_{15}$ are independently selected from $C_1$ to $C_3$ alkyl or phenyl;

m is 1 to 2;
n is 1 to 2;
p is 1 to 2;
q is 0;
V is S; and
a is 2.

Preferred Compounds (C) are Compounds B wherein:

$R_3$ is H, $C_1$-$C_4$ alkyl, $C_1$-$C_4$ haloalkyl, $C_2$-$C_4$ alkenyl, $C_2$-$C_4$ alkynyl, CN, phenyl optionally substituted with $(R_{10})p$ or benzyl optionally substituted with 1 to 2 substituents independently selected from W;

$R_4$ is H, $C_1$-$C_3$ alkyl, $C_3$-$C_4$ alkenyl or $C_3$-$C_4$ alkynyl;

$R_5$ is H, Me, $CO_2Me$, $CO_2Et$, $SR_{11}$ or phenyl optionally substituted with 1 to 2 substituents independently selected from W;

$R_6$ is H, Me, C(O)Me, $CO_2Me$ or $SR_{11}$;

$R_{11}$ is $C_1$-$C_3$ alkyl, $NR_{12}C(O)R_{13}$, $NR_{12}S(O)_aR_{13}$, $C(O)R_{13}$, or phenyl optionally substituted with Cl, $NO_2$ or $CH_3$;

$R_{12}$ is $C_1$-$C_4$ alkyl or phenyl optionally substituted with Cl or $CH_3$;

$R_{13}$ is $C_1$-$C_{12}$ alkyl, $C_1$-$C_{12}$ alkoxy, $C_1$-$C_6$ haloalkyl, dimethylamino, phenyl optionally substituted with Cl or $CH_3$, or $R_{13}$ is $C_1$-$C_4$ alkoxy substituted with $C_2$-$C_4$ alkoxy or 1 to 6 halogens;

A is $CH_2$, $CH_2CH_2$, O, S, $OCH_2$, $NR_7$ or $SCH_2$, wherein, each carbon is optionally substituted with $C_1$-$C_3$ alkyl or phenyl, wherein, the phenyl is optionally substituted with W; and;

$R_7$ is H, $C_1$-$C_4$ alkyl, $C_2$-$C_4$ alkenyl, $C_2$-$C_4$ alkynyl, $C_2$-$C_4$ alkylcarbonyl, $C_2$-$C_4$ alkoxycarbonyl or $C_1$-$C_4$ alkylsulfonyl.

Preferred Compound (D) are Compounds C wherein:

$R_1$ and $R_2$ are independently selected from F, Cl, Br, CN, $NO_2$, OMe, $CF_3$, $OCF_2H$, $OCF_2CF_2H$, SMe, $SO_2Me$, $SCF_2H$ or when m or n is 2 $R_1$ or $R_2$ respectively is optionally taken together as $CH_2C(CH_3)2O$ or $CF_2CF_2O$;

$R_3$ is Cl to $C_4$ alkyl, allyl, propargyl, or phenyl optionally substituted with F, Cl, Br, $CF_3$, $OCF_2H$, $OCF_3$, $SCF_2H$, CN, $NO_2$, $CH_3$, OMe or $CO_2Me$;

$R_4$ is H or $CH_3$;

$R_5$ is H, $CH_3$ $CO_2CH_3$, $CO_2Et$, or phenyl optionally substituted with F or Cl;

$R_6$ is H, $CH_3$, $C(O)CH_3$ or $CO_2CH_3$; and

A is O, S or $CH_2$, optionally substituted with $C_1$-$C_3$ alkyl or phenyl which may also be optionally substituted with W.

Preferred Compounds (E) are Compounds D wherein A is $CH_2$; and $R_3$ is optionally substituted phenyl or $C_1$ to $C_4$ alkyl. Preferred Compounds (F) are compounds of Formula I wherein Q is Q-1. Preferred Compounds (G) are compounds of Formula I wherein Q is Q-2. Preferred Compounds (H) are compounds of Formula I wherein Q is Q3 Preferred Compounds (I) are compounds of Formula I wherein Q is Q4. Preferred Compounds (J) are compounds of Formula I wherein Q is $Q_5$. Preferred Compounds (K) are compounds of Formula I wherein Q is Q6 Preferred Compounds (L) are compounds of Formula I wherein Q is $Q_7$. Preferred Compounds (M) are compounds of Formula I wherein Q is $Q_8$. Preferred Compounds (N) are Compounds (E) wherein Q is Q-1.

Specifically preferred are the compounds:

O) 2-[5-fluoro-2-(4-fluorophenyl)-2,3-dihydro-1H-inden-1-yl-idene]-N-[4-(trifluoromethoxy)phenyl]hydrazine carboxamide;

P) 2-[6-chloro-2,3-dihydro-2-methyl-2-(2-propenyl)-3-benzo-furanylidene]-N-[4-(trifluoromethoxy)phenyl]-hydrazine carboxamide;

Q) 2-(5-fluoro-2,3-dihydro-2-methyl -1H-inden-1-ylidene)-N-[4-(trifluoro methyl)phenyl]hydrazine carboxamide;

R) 2-[5-chloro-2,3-dihydro-2-(1-methylethyl) -1H-inden-1-ylidene]-N-[4-(trifluoromethyl)phenyl]hydrazine carboxamide;

S) 2-(5-chloro-2,3-dihydro-2-methyl-1H-inden-1-ylidene)-N-[4-(trifluoromethyl) phenyl]hydrazine carboxamide; and T) 2-[5-fluoro-2-(4-fluorophenyl)-2,3-dihydro-1H-inden-1-yl-idene]-N-[4-(trifluoromethyl)phenyl]hydrazine carboxamide.

DETAILS OF THE INVENTION

The compounds of Formula I, where Q is Q-1, can be prepared by the reaction of hydrazones of Formula II with an aryl isocyanate of Formula III. Compounds of Formula I, where Q is Q-2 through Q-8, can be prepared by procedures which are analogous to those for compounds where Q is Q-1; therefore, for brevity only the Q-1 compounds are described. Typical reactions involve combination of equimolar amounts of II and III in a suitable solvent at temperatures generally in the range of $-10°$ to 100° C. Although the reaction can be run neat, a solvent is generally preferred. Suitable solvents typically have sufficient polarity to effect solution of the Formula II hydrazone and include, but are not limited to, ethers such as diethyl ether, tetrahydrofuran and dioxane; halogenated hydrocarbons such as methylene chloride, chloroform and carbon tetrachloride; aromatic hydrocarbons such as benzene, toluene and xylene; esters such as ethyl acetate and polar aprotic solvents such as dimethylformamide and dimethylacetamide.

SCHEME 1

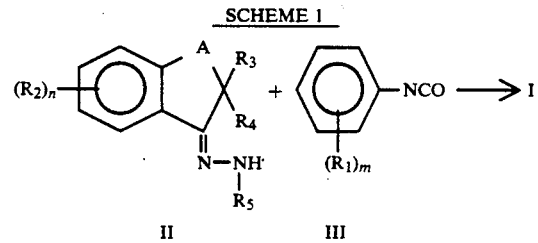

Compounds of Formula I include both geometrical and optical isomers as well as syn and anti isomers around the nitrogen-nitrogen bond. These isomers may vary in their biological activity. In some instances, it may be desirable to obtain compounds which are geometrically and/or optically pure or which are enriched in one or more of the possible isomers. All such isomers are included within the scope of this invention.

For the sake of simplifying the description of this invention, the generic formula (Formula I) encompasses certain compounds that may have long term stability problems and/or are difficult to prepare. For example, when $R_1$ is an $OCO_2R_8$ group and $R_8$ is hydrogen the $R_1$ substituent is $OCO_2H$ which will decompose to the corresponding phenol and carbon dioxide. Similarly, haloalkylamines when $R_1$ is $NR_8R_9$ and $R_8$ is $C_1$ to $C_6$ haloalkyl are unstable when the halo substituent is directly adjacent to nitrogen. These generally decompose to the corresponding hydrogen halides and imine. These compounds, however, are relatively few; their identity would be obvious to one skilled in the art, and their excision from the scope would unduly complicate and lengthen the description of the invention.

The hydrazones of Formula II can be obtained by processes known in the art involving condensation of a ketone of Formula IV with either hydrazine or a substituted derivative thereof (Formula V). This reaction is typically conducted with equimolar amounts of IV and V although greater than stoichiometric amounts of hydrazine (V) can be used. Suitable solvents include the alcohols such as methanol, ethanol, propanol, butanol and the like at temperatures in the range of 0° to 150° C., with the reflux temperature of the solvent generally being a convenient reaction temperature. Acid catalysis can also be useful, particularly for some of the more sterically hindered Formula IV compounds. Typical acid catalysts include sulfuric, hydrochloric and p-toluene sulfonic acid.

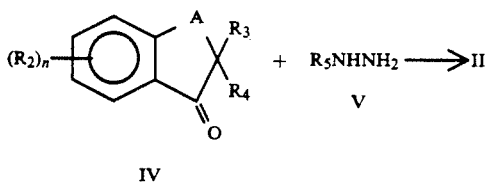

IV

An alternate process useful for the preparation of compounds of Formula I involves condensation of a phenyl substituted semicarbazide of Formula VI with a ketone of Formula III. Preferred conditions for this reaction include an acid catalyst such as hydrochloric, sulfuric or p-toluene sulfonic acid. Reaction temperatures can range from 0° to 150° C. with the reflux temperature cf the solvent used generally preferred. Suitable solvents include, but are not limited to, ethers such as tetrahydrofuran and dioxane; aromatic hydrocarbons such as benzene and toluene; and especially preferred are alcohols such as methanol, ethanol and isopropanol.

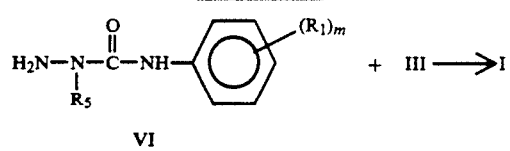

VI

Compounds of Formula I where $R_5$ and $R_6$ are other than hydrogen can generally be prepared from the corresponding compounds where $R_5$ and $R_6$ are hydrogen by reaction with electrophilic reagents such as alkyl halides, acyl halides, alkyl chloroformates and sulfenyl halides. The use of a base is generally preferred in these reactions but is dependent upon the specific nature of the reactants. For example, when the electrophilic reagent is selected from an alkyl halide, acyl halide or alkyl chloroformate, then metal hydrides such as sodium hydride or potassium hydride in solvents such as tetrahydrofuran or dimethylformamide are preferred. When sulfenyl halides are used then amine bases such as triethylamine in solvents such as diethyl ether or tetrahydrofuran are generally preferred. Of course, many of the compounds where $R_5$ is other than H can also be prepared by use of the appropriate hydrazine V in Scheme 2. For example, methyl hydrazine and methyl carbazate will produce compounds where $R_5$ is methyl and carbomethoxy, respectively.

The starting ketones of Formula II are known or can be obtained by processes analogous to known ones. Those skilled in the art will recognize the Formula II compounds to include indanones, tetralones, chromanones, thiochromanones, benzofuran-3-ones, thiobenzofuran-3-ones, isochromanones, isothiochromanones and others.

The following Examples illustrate the invention.

EXAMPLE 1

Step A: 3-chloro-α-(4-chlorophenyl)benzenepropanoic acid

To a solution of 6.8 g (0.17 mol) of 60% sodium hydride in 150 ml of dimethylformamide under nitrogen was added 30.0 g (0.162 mol) of methyl 4-chlorophenylacetate dropwise such that hydrogen evolution was moderate and the temperature of the reaction was maintained at less than 50° C. Once hydrogen evolution had ceased, a solution of 3-chlorobenzylbromide in 30 ml of dimethylformamide was added very cautiously such that the reaction temperature was maintained at less than 60° C. The reaction was maintained at 50° to 60° C. with stirring overnight after which time it was partitioned between 5% aqueous $NaHCO_3$ and diethyl ether, the aqueous extracts were washed twice with ether and the combined organic extracts were then washed with water. The ether extracts were dried over $MgSO_4$, filtered and concentrated to afford 48.0 g of a brown oil.

The crude product was combined with 300 ml of methanol, 40 ml of water and 20 ml of 50% aqueous sodium hydroxide and refluxed overnight. After this time the reaction was concentrated and the crude residue partitioned between water and ether. The aqueous extracts were acidified with conc. hydrochloric acid and extracted several times with ether. The ether extracts were dried over $MgSO_4$, filtered and concentrated to 48.8 g of a yellow, oily solid.

¹H NMR (CDCl₃) δ3.0 (dd, 1H), 3.3 (m, 1H), 3.84 (t, 1H), 6.77 (d, 1H), 6.9–7.4 (m).

Step B: 5-chloro-2-(4-chlorophenyl)-2,3-dihydro-1H-inden-1-one

The crude product from Step A was combined with 50 ml of thionyl chloride and then heated at reflux for 2 hours. Thionyl chloride was removed by concentration at reduced pressure and then the mixture was concentrated several times from carbon tetrachloride. The residue was combined with 200 ml of dichloroethane, cooled under nitrogen to 0° C., and 24.5 g of aluminum trichloride was then added. After stirring overnight the reaction was poured onto a mixture of ice in 1N hydrochloric acid, extracted three times with ether and chromatographed on silica gel (10% ethyl acetate/hexane) to afford 18.6 g of a yellow oily solid.

¹H NMR (CDCl₃) δ 3.20 (dd, 1H), 3.68 (dd, 1H), 3.90 (dd, 1H), 6.9–7.6 (m), 7.75 (d, 1H).

Step C: 2-[5-chloro-2-(4-chlorophenyl)-2,3-dihydro 1H-inden-1-ylidene]-N-[4-(trifluoromethyl) phenyl]hydrazinecarboxamide A mixture of 1.5 g of the indanone from Step B and 0.75 ml of hydrazine hydrate in 10 ml of ethanol was refluxed under N₂ overnight. The mixture was then partitioned between 5% NaHCO₃ and ether, the aqueous extracts were washed with chloroform and the combined chloroform/ether extracts were washed with water. The organic extracts were dried over magnesium sulfate and concentrated to 1.54 g of a yellow oil. To 0.45 g of this oil was added 10 ml of THF and 0.29 g of 4-trifluoromethylphenyl isocyanate. The mixture was then stirred under nitrogen overnight. Concentration at reduced pressure and then trituration with ether provided 0.27 g of the title compound as a yellow solid, m.p. 214° to 216° C.

¹H NMR (CDCl₃) δ2.95 (dd, 1H), 3.74 (dd, 1H), 4.30 (dd, 1H), 7.1–7.8 (m), 8.33 (s, 1H); IR (nujol) 1680, 3190, 3360 cm⁻¹.

EXAMPLE 2

Step A: ethyl 2[5-fluoro-2-(4-fluorophenyl)-2,3-dihydro-1H-inden-1-ylidene]hydrazine carboxylate To a mixture of 1.5 g of 5-fluoro-2-(4-fluorophenyl)-2,3-dihydro-1H-inden-1-one (prepared by a procedure analogous to Example 1, Step B) and 0.63 g of ethyl carbazate in 20 ml of methanol was added 1 drop of conc. H₂SO₄ and the reaction was refluxed under nitrogen overnight. The reaction was then partitioned between ethyl acetate and 5% aqueous NaHCO₃, the aqueous extracts were washed with ethyl acetate and the combined organic extracts were dried over MgSO₄. Concentration of the organic extract afforded 1.9 g of a yellow oil, which was triturated with ether to afford 1.27 g of a white solid, m.p. 139°–141° C.

¹H NMR (CDCl₃) δ1.26 (t, 3H), 2.91 (dd, 1H), 3.70 (dd, 1H), 4.2 (m, 3H), 6.9–7.3 (m, 6H), 7.52 (bs, 1H), 7.93 (dd, 1H).

Step B: ethyl 2-[5-fluoro-2-(4-fluorophenyl)-2,3-dihydro-1H-inden-1-ylidene]-1-[[[4-(trifluoromethyl)phenyl]amino]carbonyl]hydrazine carboxylate To a solution of 1.02 g of the ethyl carboxylate from Step A and 0.62 g of 4-trifluoromethylphenylisocyanate in 10 ml of THF was added 0.26 ml of triethylamine and the mixture was stirred under nitrogen overnight. The reaction was then partitioned between ethyl acetate and 5% aqueous NaHCO₃ and the aqueous extracts were washed twice with ethyl acetate. The organic extracts were dried over MgSO₄ and concentrated to 1.67 g of a yellow oil. Chromatography on silica gel afforded 0.37 g of a yellow solid m.p. 144–146.

¹H NMR (CDCl₃) δ1.16 (t, 3H), 3.00 (dd, 1H), 3.65 (dd, 1H), 3.8–3.9 (m, 1H), 4.0–4.1 (m, 1H), 4.32 (dd, 1H), 6.85–7.2 (m, 6H), 7.60 (s, 4H), 8.05 (dd, 1H), 10.66 (s, 1H).

EXAMPLE 3

Step A: N-[4-trifluoromethyl)phenyl]hydrazine carboxamide

To a 0° C. solution of 10 ml of hydrazine hydrate and 75 ml of THF was added dropwise a solution of 6 g of 4-trifluoromethyl phenyl isocyanate in 20 ml of THF. After 1 hr TLC indicated the reaction was complete. The reaction was partitioned between ether and water, the ether extracts were washed twice with water, dried over MgSO₄, and concentrated to 6.34 g of a white solid, m.p. 168°–172° C.

¹H NMR (CDCl₃) δ3.9 (bm, 2H), 6.1 (bs, 1H), 7.56 (d, 2H), 7.61 (d, 2H), 8.4 (bs, 1H).

Step B: methyl-5-chloro-2,3-dihydro-2-methyl-1-oxo-1H-indene-2-carboxylate

To a mixture of 8.0 g of 5-chloroindanone and 4.2 ml of dimethylcarbonate in 60 ml of THF was added 4.0 g of 60% NaH and the mixture was heated to reflux under N₂ overnight. After this time the reaction was cooled to room temperature and 4.0 ml of methyl iodide was added and the mixture was reheated to reflux overnight. The reaction was then cooled and partitioned between ether and 5% aqueous NaHCO₃ and the aqueous extracts were washed twice with ether. The combined aqueous extracts were dried over MgSO₄ and concentrated to 11.24 g of a brown oil. Chromatogrpahy on silica gel (10% ethyl acetate/hexane) afforded 4.25 g of the title compound as a brown oil.

1H NMR (CDCl₃) δ1.52 (s, 3H), 2.96 (d, 1H), 3.68 (s, 3H), 3.69 (d, 1H), 7.40 (d, 1H), 7.47 (s, 1H), 7.71 (d, 1H).

Step C: methyl 5-chloro-2,3-dihydro-2-methyl-1-[[[[4-(trifluoromethyl)phenyl]amino]carbonyl]hydrazine]-1H-indene-2-carboxylate To a mixture of 0.92 g of the compound from Step A and 1.0 g of the compound from Step B in 10 ml of methanol was added 1 drop of conc. H₂SO₄ and the mixture was heated to reflux under N₂ overnight. The reaction was then cooled to 0° C. and the precipitate filtered, rinsed with cold methanol and dried to 0.39 g of a brown solid, m.p. 192°–194° C.

1H NMR (CDCl₃) δ 1.70 (s, 3H), 3.00 (d, 1H), 3.82 (s, 3H), 3.87 (d, 1H), 7.3 (m, 2H), 7.6–7.8 (m, 5H), 8.38 (s, 1H), 8.98 (s, 1H).

EXAMPLE 4

Step A: 3-(4-fluorophenyl)-1-phenyl-2-propen-1-one

To a mechanically stirred solution of 5.0 g NaOH in 35 ml H₂O and 25 ml EtOH at 15° C. was added 12.0 g (0.100 mole) of acetophenone and 12.4 g (0.100 mole) of 4-fluorobenzaldehyde. After a brief exotherm to 25° C., the temperature returned to 15° C., and the cooling bath was removed. The reaction mixture was stirred at room temperature for 1.5 hour, and the thick slurry was transferred to a beaker to cool overnight at 10° C. This mixture was filtered, and the solids were washed with distilled H$_2$O until the washings were neutral to litmus. Upon drying in vacuo, 20.8 g of a pale yellow solid was obtained, m.p. 86°-87° C.

IR (Nujol): 1660, 1605, 1590, 1580 cm$^{-1}$.

1H NMR (200 MHz, CDCl$_3$): δ7.12 (d, J=16 Hz, 1H), 7.42-7.68 (m, 7H), 7.78 (d, J=16 Hz, 1H), 8.02 (m, 2H).

Step B:
3-(4-fluorophenyl)-2,3-dihydro-1H-indene-1-one

The title compound of Step A, Example 4, 11.3 g (0.50 mole), was added to 250 ml of mechanically-stirred polyphosphoric acid at 135° C., under a nitrogen atmosphere. This mixture was heated at 135° C. for 2 hours and then allowed to cool to 90° C. Ice water was added at such a rate as to maintain a temperature below 125° C. Once the material had become fluid, it was poured over ice and extracted with ether. The ether extracts were washed twice with saturated aqueous NaHCO$_3$ and once with brine. The ethereal solution was dried over MgSO$_4$ and concentrated at reduced pressure. The resultant residue was recrystallized from hexane/chlorobutane to afford 5.90 g of the title compound as a brown powder, m.p. 117°-120° C.

IR (Nujol): 1705 (s), 1600 (br, m).

1H NMR (200 MHz, CDCl$_3$): δ 2.64 (dd, 1H), 3.22 (dd, 1H), 4.57 (dd, 1H), 6.96-7.15 (m, 4H), 7.25 (m, 1H), 7.44 (m, 1H), 7.58 (m, 1H), 7.81 (m, 1H).

Step C:
2-[3-(4-fluorophenyl)-2,3-dihydro-1H-inden-1-ylidene]-N-[4-(trifluoromethyl)phenyl]hydrazine carboxamide The title compound of Step B, Example 4, 2.26 g (0.010 mole), was combined with 0.60 ml of hydrazine monohydrate (0.012 mole) in 30 ml of methanol and heated at reflux for 2 to 2.5 hours. The reaction mixture was concentrated at reduced pressure, and the resultant residue was dissolved in ethyl acetate and washed with saturated aqueous NaHCO$_3$, H$_2$O, and brine. The organic phase was dried over MgSO$_4$ and concentrated in vacuo to afford 2.37 g of crude material. This material was dissolved in 30 ml of dry THF, and a 10 ml aliquot of this solution was added to a solution of 0.62 g (0.0033 mole) of 4-(trifluoromethyl)phenyl isocyanate in 20 ml of dry THF. After this mixture was stirred overnight under a nitrogen atmosphere, it was concentrated in vacuo. The resultant residue was triturated with hexanes and filtered to obtain 1.23 g of an off-white product, m.p. 253°-255° C.

1H), 4.65 (dd, 1H), 7.0-7.16 (m, 5H), 7.33-7.37 (m, 2H), 7.63-7.67 (m, 2H), 7.91-7.95 (m, 2H), 8.08 (m, 1H), 9.30 (s, NH), 10.00 (s, NH).

EXAMPLE 5

Step A: ethyl 4-fluoro-α-methylenebenzeneacetate

Sodium ethoxide solution was prepared by portionwise addition of sodium pieces (1.5 g, 0.065 mol) to ethanol (50 ml). To this solution was added first, 8.9 ml (0.065 mol) of diethyloxalate in one portion and second, 10 g (0.059 mol) of methyl 4-fluorobenzeneacetate dropwise at such a rate as to keep the reaction mixture at 25° C. After stirring at room temperature for 2 hrs, the ethanol was concentrated and the residue taken up in toluene. The toluene solution was concentrated and the solid residue was taken up in ether and 10% aqueous acetic acid. After stirring at room temperature for 1 hr the mixture was separated and the aqueous phase extracted twice with ether. The combined ether phases were washed once with saturated aqueous NaHCO$_3$ solution, dried (MgSO$_4$), and concentrated. The NMR of the crude product was complicated by a mixture of methyl and ethyl esters.

The crude diester was combined with 25 ml of water and 8 ml of 37% formalin solution. To this somewhat heterogeneous mixture was added a solution of 6.5 g of K$_2$CO$_3$ in 36 ml of water, dropwise as such a rate as to maintain a temperature of about 25° C. The reaction was stirred vigorously for three hours to mix the fine emulsion. Ether was added and the aqueous phase was separated and extracted three times with ether. The combined ether phases were dried (MgSO$_4$) and concentrated to a colorless oil (11 g, 96% yield).

$^1$H NMR (CDCl$_3$) δ: 7.41 (2H, m), 7.03 (2H, m), 6.34 (1H, s), 5.85 (1H, s), 4.28 (2H, q, J=7 Hz), 1.32 (3H, t, J=7 Hz).

Step B: ethyl 4-fluoro-α-[[(2-fluorophenyl)thiolmethyl]]benzeneacetate

The crude product from Step A (3.9 g, 20 mmole) was taken up in 20 ml of ethanol. To this solution, being stirred at room temperature, was added 2-fluorothiophenol (2.5 g, 20 mmole) and 50 mg of solid sodium ethoxide. After stirring for eight hours the ethanol was concentrated and the residue taken up in ether. The ether mixture was washed twice with 15% NaOH solution, dried (MgSO$_4$) and concentrated to a colorless oil (5.3 g, 82% yield). 1H NMR (CDCl$_3$) δ: 7.28 (4H, m), 7.06 (4H, m), 4.13 (2H, m), 3.72 (1H, m), 3.55 (1H, m), 3.20 (1H, dd, J=6, 12 Hz), 1.21 (3H, t, J=6 Hz).

Step C:
4-fluoro-α-[[(2-fluorophenyl)thio]methyl]benzeneacetic acid

The crude ester from Step B (5.3 g, 16 mmole) was combined with 20 ml of 88% formic acid and 2.1 ml (33 mmole) of methane sulfonic acid. The emulsion was refluxed for five hours during which time it gradually became homogeneous. After cooling, water and methylene chloride were added and the aqueous phase was separated and extracted twice with methylene chloride. The organic phases were combined, dried (MgSO$_4$) and concentrated. The crude residue was taken up in 4% ethyl acetate/hexane and filtered through a plug of silica gel to remove nonpolar impurities. The product acid was then rinsed from the silica gel with ethyl acetate and the solvent concentrated. The acid was a colorless solid (4.5 g, 95% yield).

1H NMR (CDCl$_3$) δ: 10.05 (1H, br s), 7.20 (5H, m), 7.03 (3H, m), 3.81 (1H, dd, J=6, 8 Hz), 3.57 (1H, m), 3.23 (1H, dd, J=6, 12 Hz).

Step D:
8-fluoro-3-(4-fluorophenyl)-2.3-dihydro-4H-1-benzothiopyran-4-one The acid from Step C (4.5 g, 15 mmole) was dissolved in 30 ml of thionyl chloride and refluxed for four hours. After cooling the thionyl chloride was concentrated and the residue taken up in carbon tetrachloride. The carbon tetrachloride was concentrated and the residue was taken up in 30 ml of dichloroethane. To the dichloroethane solution being cooled in an ice bath, was added aluminum trichloride (total of 2.1 g, 16 mmole) in three portions every 15 min. After stirring the black solution for an additional 30 min at 0° C., a 5% aqueous HCl solution was added. The aqueous phase was separated and extracted twice with methylene chloride. The organic phases were combined, dried (MgSO$_4$), and concentrated to give the crude product as a yellow oil (3.4 g, 82% yield).

1H NMR (CDCl$_3$) δ: 7.97 (1H, dd, J=3, 9 Hz), 7.19 (6H, m), 4.12 (1H, dd, J=4, 12 Hz), 3.58 (1H, m), 3.32 (1H, ddm J=4, 12 Hz).

Step E:
2-[8-fluoro-3-(4-fluorophenyl)-3,4-dihydro-2H-1-benzothiopyran-4-ylidene]-N-[4-(trifluoromethyl)phenyl]-hydrazinecarboxamide The thiochromanone from Step D (1.1 g, 4.0 mmole) was treated according to the procedure in Example 1 Step C to give the desired product as a white powder (0.32 g, 17% yield). m.p.=217°-219° C. 1H NMR (CDCl$_3$) δ: 8.33 (1H, s), 7.98 (1H, d, J=9 Hz), 7.69 (1H, s) 7.60 (4H, AB, J$_{AB}$=8 Hz), 7.15 (6H, m), 4.42 (1H, t, J=4 Hz), 3.44 (1H, dd, J=4, 12 Hz), 2.99 (1H, dd, J=4, 12 Hz).

EXAMPLE 6

Step A: methyl 6-fluoro-1,2,3,4-tetrahydro-1-oxo-2-naphthalenecarboxylate

Hexane washed sodium hydride (3.5 g of 60%, 88 mmole) was covered with 75 ml of tetrahydrofuran and 5.4 ml (64 mmole) of dimethylcarbonate was added in one portion. The solution was heated to reflux and 6-fluoro-3,4-dihydro-1(2H)-naphthlenone (7.2 g, 44 mmole) in 25 ml of tetrahydrofuran was added dropwise while maintaining reflux. After the addition was complete, the reaction was refluxed for 1.5 hours. The reaction was then cooled in an ice bath and 10% aqueous HCl solution was carefully added. The solution was diluted with ether and the aqueous phase was separated and extracted twice with ether. The combined organic phases were dried (MgSO$_4$) and concentrated. The crude product was a pale yellow solid (9.6 g, 98% yield).

1H NMR (CDCl$_3$) δ: 7.99 (1H, dd, J=6,8 Hz), 6.95 (2H, m) 3.83 (3H, s), 3.82 (1H, m), 2.81 (2H, m), 2.58 (2H, m). NMR complicated by signals from enol tautomer.

Step B: methyl 6-fluoro-1,2,3,4-tetrahydro-1-oxo-2-phenyl-2-naphthalenecarboxylate The tetralone from Step A (2.4 g, 10.8 mmole) and triphenylbismuth dichloride (5.8 g, 11.3 mmmole) were dissolved in 50 ml of benzene. 1,8-Diazabicyclo[5.4.0]-undec-7-ene (1.8 ml, 11.8 mmole) was added and the pale yellow solution was heated at reflux for 12 hours. The benzene solution was decanted from the gray sludge. The sludge was in turn triturated twice with ether and twice with acetone. The combined benzene, ether, and acetone phases were washed once with water, dried (MgSO$_4$), and concentrated. The resulting residue was flash chromatographed on silica gel eluting with 10% acetone/hexane. Purified product was obtained in 90% yield (2.9 g) as a viscous oil which solidified on standing.

1H NMR (CDCl$_3$) δ: 8.17 (1H, dd, J=8,10 Hz), 7.31 (5H, m) 7.02 (1H, dt, J=3,8 Hz), 6.85 (1H, dd, J=3,9 Hz), 3.75 (3H, s), 2.94 (2H, m), 2.89 (2H, m).

Step C:
6-fluoro-3,4-dihydro-2-phenyl-1(2H)-naphthalenone

The tetralone from Step B (2.8 g, 9.4 mmole) was dissolved in 45 ml of dimethylformamide. To this solution was added lithium chloride (2.0 g, 47 mmole) and water (0.42 ml, 23 mmole). The reaction mixture was heated to 150° C. for 2.5 hrs and then cooled and partitioned between ether and water. The aqueous phase was separated and extracted three times with ether. The combined organic phases were washed once with water, dried (MgSO$_4$), and concentrated (1.96 g, 87% yield).

1H NMR (CDCl$_3$) δ: 8.13 (1H, dd, J=6,10 Hz), 7.31 (5H, m) 6.99 (2H, m), 3.80 (1H, m), 3.07 (2H, m), 2.43 (2H, m).

Step D:
2-(6-fluoro-1,2,3,4-tetrahydro-2-phenyl-1-naphthalenylidene)-N-[4-(trifluoromethyl)phenyl]hydrazinecarboxamide The crude product from Step C (0.65 g, 2.7 mmole) was treated according to the procedure in Example 1, Step C. The product was obtained as a white powder (0.26 g, 22% yield). m.p.=158°-160° C.

1H NMR (CDCl$_3$) δ: 8.45 (1H, s), 8.15 (1H, d, J=9 Hz), 7.98 (1H, s), 7.61 (5H, m), 7.29 (2H, m), 7.18 (2H, m), 6.92 (1H, dd, J=3,9 Hz), 6.75 (1H, d, J=3 Hz), 4.18 (1H, m), 2.64 (2H, m), 2.31 (1H, m), 2.10 (1H, m).

EXAMPLE 7

Step A:
4-Chloro-2-(2-methoxy-1-methyl-2-oxoethoxy)benzoic acid, methyl ester A solution of methyl 4-chlorosalicylate (5.0 g) in dimethylformamide (10 ml) was treated sequentially with methyl 3-bromopropionate (4.0 g) and potassium carbonate (6.0 g). The mixture was stirred at room temperature for 18 hrs and diluted with water. The mixture was extracted with ether and the organics were washed with water. The organic layer was dried and evaporated to give the desired material (6.7 g) as a low melting solid.

NMR: 7.8 (d, 1H), 7.2 (m 1H), 6.9 (m, 1H), 4.8 (q, 1H), 3.9 (s, 3H), 3.8 (s, 3H), 1.7 (d, 3H).

Step B: 6-chloro-2-methyl-3(2H)-benzofuranone

A mixture of the compound of Example 7, Step A, (6.7 g) and sodium hydride (60% in oil, 1.5 g) was heated to reflux in tetrahydrofuran (50 ml). It was then allowed to cool to room temperature over 1.5 hrs. The cooled mixture was treated with aqueous ammonium chloride solution and ether. The ether solution was dried over magnesium sulfate and then evaporated. The oil was subjected to chromatography on silica gel with hexanes/ethyl acetate (25:1) as the eluent. The desired product (1.99 g) was obtained as a low melting solid.

NMR: 7.6 (d, 1H), 7.1 (m 2H), 4.7 (q, 1H), 1.55 (d, 3H).

Step C:
(Z)-2-(6-chloro-2-methyl-3(2H)-benzofuranylidene)-N-[4-(trifluoromethyl)phenyl]hydrazinecarboxamide The compound of Example 7, Step B, (1.9 g) was dissolved in ethanol (15 ml) and degassed with nitrogen. Then hydrazine hydrate (1.2 ml) was added and the mixture was heated at reflux for 1.5 hrs and evaporated to dryness. The residue was chromatographed on silica in hexanes/ethyl acetate (2:1). The first product eluted was the hydrazone syn to the methyl group (0.5 g). The next fraction (0.9 g) was mixed syn and anti. Pure anti hydrazone was eluted last (0.5 g). The syn hydrazone was treated with p-trifluoromethylphenylisocyanate (0.4 ml) in ether (10 ml). The desired material began to crystallize soon after mixing. The mixture was filtered and washed with ether to provide a solid (0.8 g). m.p.: 196°–198° C. NMR: 10.0 (br, 1H), 9.4 (br, 1H), 8.2–7.0 (m, 7H), 5.35 (m, 1H), 1.6 (d, 3H).

Step D:
(E)-2-(6-chloro-2-methyl-3(2H)-benzofuranylidene)-N-[4-(trifluoromethyl)phenyl)hydrazinecarboxamide Treating the anti hydrazone (0.5 g) obtained in Step C with p-trifluoromethylphenylisocyanate (0.4 ml) in the same manner as in Step C resulted in the isolation of the desired product as a solid (0.8 g). m.p.=205°–207° C. NMR: (10.4 (br, NH), 9.4 (br, 1H), 8.2–7.0 (m, 7H), 5.8 (m, 1H), 1.47 (d, 3H).

By the general procedures described herein and obvious modifications known to one skilled in the art, one can prepare the compounds of Tables 1 to 16. The compounds of Tables 1 through 10 are listed along with their melting points.

In Tables 1 through 16 the following notations have been used:

1. 3,4-CF$_2$CF$_2$O is 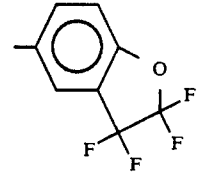

2. 3,4-OCF$_2$CF$_2$ is 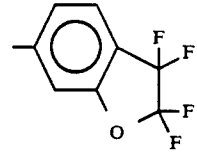

3. 3,4-CH$_2$C(Me)$_2$O is 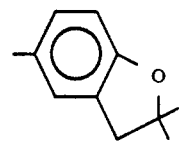

4. 3,4-OC(Me)$_2$CH$_2$ is 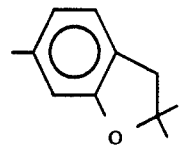

5. When A is OCH$_2$ or SCH$_2$, the compounds of Formula I are, respectively,

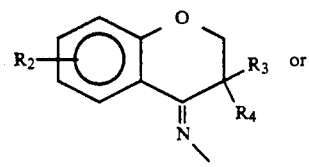

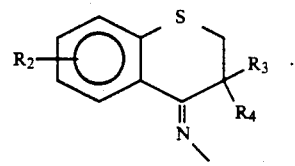

6. When A is CH$_2$O or CH$_2$S, the compounds of Formula I are, respectively,

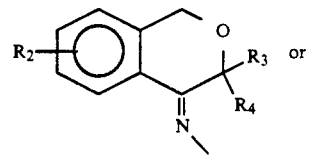

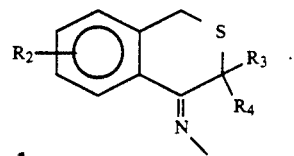

TABLE 1

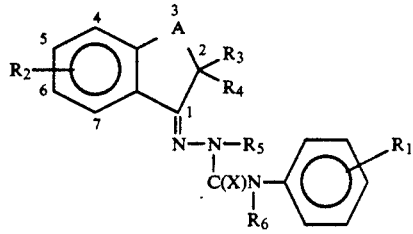

(A = CH$_2$, X = O)

| CMPD | R$_1$ | R$_2$ | R$_3$ | R$_4$ | R$_5$ | R$_6$ | m.p. °C. |
|---|---|---|---|---|---|---|---|
| 1 | 4-CF$_3$ | 5-Cl | 4-Cl—Ph | H | H | H | 214–216 |
| 2 | 4-Br | 5-Cl | 4-Cl—Ph | H | H | H | 230–232 |

TABLE 1-continued

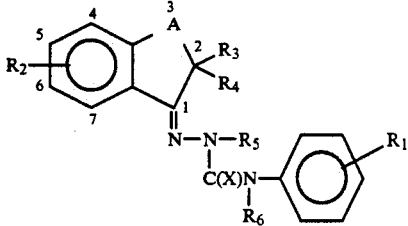

(A = CH₂, X = O)

| CMPD | R₁ | R₂ | R₃ | R₄ | R₅ | R₆ | m.p. °C |
|---|---|---|---|---|---|---|---|
| 3 | 4-OMe | 5-Cl | 4-Cl—Ph | H | H | H | 202-204 |
| 4 | 4-Cl | 5-Cl | 4-Cl—Ph | H | H | H | 231-233 |
| 5 | 4-CF₃ | 5-Cl | Ph | H | H | H | 226-228 |
| 6 | 4-Br | 5-Cl | Ph | H | H | H | 237-238 |
| 7 | 4-OCF₃ | 5-Cl | Ph | H | H | H | 198-200 |
| 8 | 4-CF₃ | 5-Cl | 4-F—Ph | H | H | H | 223-225 |
| 9 | 4-Cl | 5-Cl | 4-F—Ph | H | H | H | 224-226 |
| 10 | 4-Br | 5-Cl | 4-F—Ph | H | H | H | 230-232 |
| 11 | 4-CF₃ | 5-F | 4-Cl—Ph | H | H | H | 214-216 |
| 12 | 4-Cl | 5-F | 4-Cl—Ph | H | H | H | 218-220 |
| 13 | 4-Br | 5-F | 4-Cl—Ph | H | H | H | 223-225 |
| 14 | 4-CF₃ | 5-F | 4-F—Ph | H | H | H | 224-226 |
| 15 | 4-Cl | 5-F | 4-F—Ph | H | H | H | 212-214 |
| 16 | 4-Br | 5-F | 4-F—Ph | H | H | H | 219-221 |
| 17 | 4-OCF₃ | 5-F | 4-F—Ph | H | H | H | 201-203 |
| 18 | 4-CF₃ | 5-F | Ph | H | H | H | 230-232 |
| 19 | 4-Cl | 5-F | Ph | H | H | H | 233-235 |
| 20 | 4-Br | 5-F | Ph | H | H | H | 236-238 |
| 21 | 4-OCF₃ | 5-F | Ph | H | H | H | 187-190 |
| 22 | 4-CF₃ | 5-OMe | Ph | H | H | H | 219-221 |
| 23 | 4-OCF₃ | 5-OMe | Ph | H | H | H | 189-191 |
| 24 | 4-CF₃ | 5-OMe | 4-F—Ph | H | H | H | 197-199 |
| 25 | 4-CF₃ | 5-OCH₂CF₃ | 4-F—Ph | H | H | H | 217-219 |
| 26 | 4-OCF₃ | 4-OCH₂CF₃ | 4-F—Ph | H | H | H | 204-206 |
| 27 | 4-CF₃ | 5-O-i-Pr | 4-F—Ph | H | H | H | 198-201 |
| 28 | 4-CF₃ | 4-OPh | 4-F—Ph | H | H | H | 224-226 |
| 29 | 4-CF₃ | 5-OEt | 4-F—Ph | H | H | H | 206-208 |
| 30 | 4-OCF₃ | 5-OEt | 4-F—Ph | H | H | H | 195-197 |
| 31 | 4-Cl | H | Ph | H | H | H | 220-221 |
| 32 | 4-Br | H | Ph | H | H | H | 231-232 |
| 33 | 4-CF₃ | H | Ph | H | H | H | 223-224 |
| 34 | 4-Cl | H | 4-F—Ph | H | H | H | 197-201 |
| 35 | 4-CF₃ | 5-OH | Ph | H | H | H | 240-242 |
| 36 | 4-CF₃ | 5-Br | 4-F—Ph | H | H | H | 218-220 |
| 37 | 4-Br | 5-Br | 4-F—Ph | H | H | H | 227-229 |
| 38 | 4-CF₃ | 5-F | 3-CF₃—Ph | H | H | H | 225-227 |
| 39 | 4-Br | 5-F | 3-CF₃—Ph | H | H | H | 221-223 |
| 40 | 4-CF₃ | 5-F | 2-F—Ph | H | H | H | 218-220 |
| 41 | 4-Br | 5-F | 2-F—Ph | H | H | H | 231-233 |
| 42 | 4-CF₃ | 5-F | 3-F—Ph | H | H | H | 210-212 |
| 43 | 4-Br | 5-F | 3-F—Ph | H | H | H | 218-220 |
| 44 | 4-CF₃ | 5-F | 2,4-di-F—Ph | H | H | H | 219-221 |
| 45 | 4-Br | 5-F | 2,4-di-F—Ph | H | H | H | 214-216 |
| 46 | 4-CF₃ | 5-F | 4-OEt—Ph | H | H | H | 184-186 |
| 47 | 4-CF₃ | 5-F | 4-Me—Ph | H | H | H | 219-221 |
| 48 | 4-Br | 5-F | 4-Me—Ph | H | H | H | 227-229 |
| 49 | 4-CF₃ | 5-F | 2-naphthyl | H | H | H | 229-230 |
| 50 | 4-Br | 5-F | 2-naphthyl | H | H | H | 230-232 |
| 51 | 4-CF₃ | 5-F | 3,4-di-Cl—Ph | H | H | H | 214-216 |
| 52 | 4-CF₃ | 4-F | Ph | H | H | H | 214-216 |
| 53 | 4-Br | 4-F | Ph | H | H | H | 222-224 |
| 54 | 4-CF₃ | 4-F | 4-Cl—Ph | H | H | H | 236-238 |
| 55 | 4-OCF₃ | 4-F | 4-Cl—Ph | H | H | H | 209-211 |
| 56 | 2,4-di-Cl | 5-Cl | Ph | H | H | H | >250 |
| 57 | H | 5-Cl | Ph | H | H | H | 209-211 |
| 58 | 4-NO₂ | 5-Cl | Ph | H | H | H | >250 |
| 59 | 3,4-di-Cl | 5-F | 4-F—Ph | H | H | H | 132-136 |
| 60 | 2,4-di-F | 5-F | 4-F—Ph | H | H | H | 213-215 |
| 61 | 4-F | 5-F | 4-F—Ph | H | H | H | 216-218 |
| 62 | 4-CF₃ | 6-F | 4-Cl—Ph | H | H | H | 237-239 |
| 63 | 4-Cl | 6-F | 4-Cl—Ph | H | H | H | 236-238 |
| 64 | 4-Br | 6-F | 4-Cl—Ph | H | H | H | 238-240 |
| 65 | 4-CF₃ | 7-Cl | Ph | H | H | H | 124-125 |
| 66 | 4-CF₃ | 4,5-di-F | 4-F—Ph | H | H | H | 233-235 |
| 67 | 4-OCF₃ | 4,5-di-F | 4-F—Ph | H | H | H | 224-226 |
| 68 | 4-Br | 4,5-di-F | 4-F—Ph | H | H | H | 229-231 |
| 69 | 4-CF₃ | 5-Cl | 4-Cl—Ph | Me | H | H | 165-169 |

TABLE 1-continued

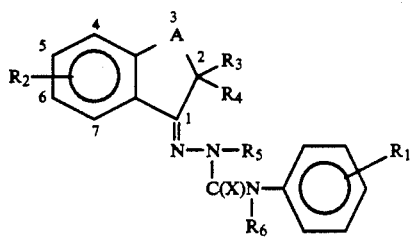

(A = CH$_2$, X = O)

| CMPD | R$_1$ | R$_2$ | R$_3$ | R$_4$ | R$_5$ | R$_6$ | m.p. °C. |
|------|-------|-------|-------|-------|-------|-------|----------|
| 70 | 4-Br | 5-Cl | 4-Cl—Ph | Me | H | H | 149-153 |
| 71 | 4-OMe | 5-Cl | 4-Cl—Ph | Me | H | H | 187-190 |
| 72 | 4-CF$_3$ | 5-F | 4-F—Ph | Me | H | H | 85-89 |
| 73 | 4-Br | 5-F | 4-F—Ph | Me | H | H | 70-74 |
| 74 | 4-CF$_3$ | 5-Cl | H | H | H | H | 240-242 |
| 75 | 4-Br | 5-Cl | H | H | H | H | 244-246 |
| 76 | 4-Cl | 5-Cl | H | H | H | H | 248-249 |
| 77 | 4-CF$_3$ | 5-Cl | Me | H | H | H | 208-210 |
| 78 | 4-Cl | 5-Cl | Me | H | H | H | 221-223 |
| 79 | 4-Br | 5-Cl | Me | H | H | H | 228-230 |
| 80 | 4-CF$_3$ | 7-Cl | Me | H | H | H | >250 |
| 81 | 4-CF$_3$ | 5-F | Me | H | H | H | 218-220 |
| 82 | 4-Cl | 5-F | Me | H | H | H | 219-221 |
| 83 | 4-Br | 5-F | Me | H | H | H | 224-226 |
| 84 | 4-CF$_3$ | 4-OMe | Et | H | H | H | 191-193 |
| 85 | 4-OCF$_3$ | 5-OMe | Et | H | H | H | 178-180 |
| 86 | 4-CF$_3$ | 5-Cl | CO$_2$Me | H | H | H | 242-244 |
| 87 | 4-CF$_3$ | 5-F | CO$_2$Me | H | H | H | 238-240 |
| 88 | 4-CF$_3$ | 5-Cl | CO$_2$Me | Me | H | H | 192-194 |
| 89 | 4-CF$_3$ | 5-F | CO$_2$Me | Me | H | H | 203-205 |
| 90 | 4-CF$_3$ | 5-Cl | i-Pr | H | H | H | 216-218 |
| 91 | 4-OCF$_3$ | 5-Cl | i-Pr | Me | H | H | 204-206 |
| 92 | 4-CF$_3$ | 5-OCH$_2$CF$_3$ | Me | H | H | H | 212-214 |
| 93 | 4-OCF$_3$ | 5-OCH$_2$CF$_3$ | Me | H | H | H | 189-191 |
| 94 | 4-Cl | 4-OCH$_2$CF$_3$ | Me | H | H | H | 220-222 |
| 95 | 4-CF$_3$ | 5-Cl | Me | Me | H | H | 215-217 |
| 96 | 4-Br | 5-Cl | Me | Me | H | H | 214-216 |
| 97 | 4-Cl | 5-Cl | Me | Me | H | H | 203-205 |
| 98 | 5-CF$_3$ | 5-F | i-Pr | H | H | H | 216-220 |
| 99 | 4-Br | 5-F | i-Pr | H | H | H | 217-222 |
| 100 | 4-CF$_3$ | 5-F | H | H | H | H | >245 |
| 101 | 4-Cl | 5-F | H | H | H | H | 240-242 |
| 102 | 4-Br | 5-F | H | H | H | H | >245 |
| 103 | 4-CF$_3$ | 5-F | 4-F—Ph | H | C(O)Me | H | oil |
| 104 | 4-OCF$_3$ | 5-F | 4-F—Ph | H | C(O)Me | H | oil |
| 105 | 4-CF$_3$ | 5-F | 4-F—Ph | H | CO$_2$Me | H | oil |
| 106 | 4-CF$_3$ | 5-F | 2,4-di-Ph | H | CO$_2$Me | H | oily solid |
| 107 | 4-CF$_3$ | 5-F | 4-F—Ph | H | CO$_2$Et | H | 144-146 |
| 108 | 4-Br | H | 4-F—Ph | H | H | H | 204-207 |
| 109 | 4-CF$_3$ | H | 4-F—Ph | H | H | H | 212-213 |
| 110 | 4-Cl | 4-Cl | Ph | H | H | H | 234-239 |
| 111 | 4-Br | 4-Cl | Ph | H | H | H | 283-285 |
| 112 | 4-CF$_3$ | 4-Cl | Ph | H | H | H | 205-209 |
| 113 | 4-CF$_3$ | 5-Me | 4-Cl—Ph | H | H | H | 210-214 |
| 114 | 4-Br | 5-Me | 4-Cl—Ph | H | H | H | 260-262 |
| 115 | 4-Cl | 5-Me | 4-Cl—Ph | H | H | H | 270-272 |
| 116 | 4-CF$_3$ | 4-Cl | 4-F—Ph | H | H | H | wax |
| 117 | 4-Br | 4-Cl | 4-F—Ph | H | H | H | wax |
| 118 | 4-Cl | 4-Cl | 4-F—Ph | H | H | H | wax |
| 119 | 4-CF$_3$ | 5-F | CH$_2$Ph-4-F | CH$_2$Ph-4-F | H | H | 76-81 |
| 120 | 4-Cl | 5-F | CH$_2$Ph-4-F | CH$_2$Ph-4-F | H | H | 84-89 |

TABLE 2

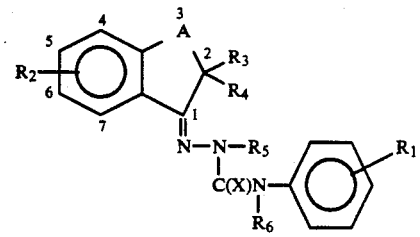

(A = CH₂CH₂, X = O)

| CMPD | R₁ | R₂ | R₃ | R₄ | R₅ | R₆ | m.p. °C. |
|---|---|---|---|---|---|---|---|
| 121 | 4-Br | 5-Cl | Ph | H | H | H | 209–210 |
| 122 | 4-CF₃ | 5-Cl | Ph | H | H | H | 217–218 |
| 123 | 4-Cl | 5-Cl | 4-Br—Ph | H | H | H | 236–238 |
| 124 | 4-Br | 5-Cl | 4-Br—Ph | H | H | H | 248–250 |
| 125 | 4-CF₃ | 5-Cl | 4-Br—Ph | H | H | H | 245–247 |
| 126 | 4-Cl | 5-Cl | 4-OMe—Ph | H | H | H | 209–210 |
| 127 | 4-Br | 5-Cl | 4-OMe—Ph | H | H | H | 216–217 |
| 128 | 4-CF₃ | 5-Cl | 4-OMe—Ph | H | H | H | 226–228 |
| 129 | 4-Cl | 5-Cl | Me | H | H | H | 236–238 |
| 130 | 4-Br | 5-Cl | Me | H | H | H | 230–235 |
| 131 | 4-CF₃ | 5-Cl | Me | H | H | H | 234–235 |
| 132 | 4-CF₃ | 5-Cl | CO₂Me | H | H | H | 220–222 |
| 133 | 4-Br | 5-Cl | 4-F—Ph | H | H | H | 221–222 |
| 134 | 4-CF₃ | 5-Cl | 4-F—Ph | H | H | H | 233–234 |
| 135 | 4-CF₃ | 5-Cl | H | H | Me | H | 114–117 |
| 136 | 4-Cl | 4-F | Me | H | H | H | 233–236 |
| 137 | 4-Br | 4-F | Me | H | H | H | 236–239 |
| 138 | 4-CF₃ | 4-F | Me | H | H | H | 235–237 |
| 139 | 4-Cl | 5-F | Ph | H | H | H | 179–184 |
| 140 | 4-Br | 5-F | Ph | H | H | H | 185–192 |
| 141 | 4-CF₃ | 5-F | Ph | H | H | H | 158–160 |
| 142 | 4-CF₃ | 4-F | CO₂Me | H | H | H | 203–204 |
| 143 | 4-CF₃ | 5-F | 4-F—Ph | H | H | H | 179–180 |
| 144 | 4-CF₃ | 5-F | 4-Cl—Ph | H | H | H | 225–230 |
| 145 | 4-Cl | 5-F | Me | H | H | H | 200–210 |
| 146 | 4-Br | 5-F | Me | H | H | H | 196–198 |
| 147 | 4-CF₃ | 5-F | Me | H | H | H | 195–198 |
| 148 | 4-CF₃ | H | CO₂Me | H | H | H | 207–208 |
| 149 | 4-CF₃ | H | CO₂Me | H | Me | H | oil |
| 150 | 4-CF₃ | H | H | H | H | H | 230–232 |
| 151 | 4-CF₃ | H | 4-Cl—Ph | H | H | H | 228–230 |

TABLE 2-continued

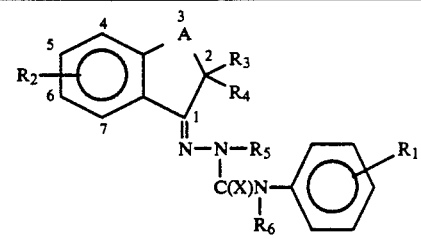

(A = CH₂CH₂, X = O)

| CMPD | R₁ | R₂ | R₃ | R₄ | R₅ | R₆ | m.p. °C. |
|---|---|---|---|---|---|---|---|
| 152 | 4-OMe | H | 4-Cl—Ph | H | H | H | 191–193 |
| 153 | 4-F | H | 4-Cl—Ph | H | H | H | 204–205 |
| 154 | 3-CF₃ | H | 4-Cl—Ph | H | H | H | 199–200 |
| 155 | 3-CO₂Et | H | 4-Cl—Ph | H | H | H | 205–206 |
| 156 | 4-F, 3-Cl | H | 4-Cl—Ph | H | H | H | 210–212 |
| 157 | 4-CF₃ | 5-Br | H | H | H | H | 253–255 |
| 158 | 4-CF₃ | 5-F | H | H | H | H | 257–259 |

TABLE 3

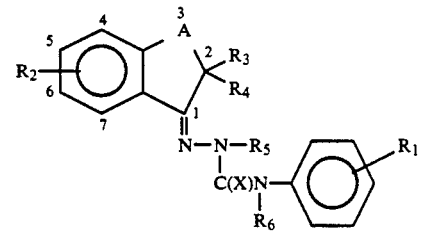

(A = (CH₂)₃, X = O)

| CMPD | R₁ | R₂ | R₃ | R₄ | R₅ | R₆ | m.p. °C. |
|---|---|---|---|---|---|---|---|
| 159 | 4-CF₃ | 5-Cl | H | H | H | H | 224–225 |
| 160 | 4-Cl | 5-Cl | H | H | H | H | 211–213 |
| 161 | 4-Br | 5-Cl | H | H | H | H | 210–213 |
| 162 | 4-CF₃ | 5-Cl | Me | H | H | H | 174–176 |

TABLE 4

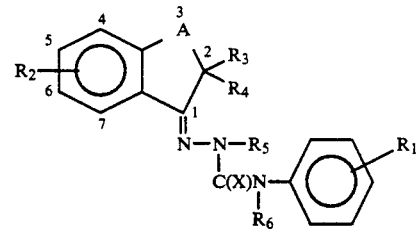

(X = O)

| CMPD | R₁ | R₂ | R₃ | R₄ | R₅ | R₆ | A | m.p. °C. |
|---|---|---|---|---|---|---|---|---|
| 163 | 4-Cl | H | Me | Me | H | H | O | 177–182 |
| 164 | 4-CF₃ | H | Me | Me | H | H | O | 186–188 |
| 165 | 4-CF₃ | 5-Cl | Me | Me | H | H | O | 214–217 |
| 166 | 4-Cl | 5-Cl | Me | Me | H | H | O | 204–207 |
| 167 | 4-Br | 5-Cl | Me | Me | H | H | O | 204–208 |
| 168 | 4-CF₃ | 4-F | Me | Me | H | H | O | 203–206 |
| 169 | 4-Cl | 4-F | Me | Me | H | H | O | 193–196 |
| 170 | 4-Br | 4-F | Me | Me | H | H | O | 194–198 |
| 171 | 4-CF₃ | 5-Cl | Me | 4-F—Ph | H | H | O | 219–220 |
| 172 | 4-Cl | 5-Cl | Me | 4-F—Ph | H | H | O | 209–211 |
| 173 | 4-CF₃ | H | Me | Ph | H | H | O | 174–176 |
| 174 | 4-Cl | H | Me | Ph | H | H | O | 165–167 |
| 175 | 4-Br | H | Me | Ph | H | H | O | 165–166 |
| 176 | 4-CF₃ | 5-Cl | Me | Et | H | H | O | 190–192 |
| 177 | 4-CF₃ | 5-Cl | Me | allyl | H | H | O | 150–152 |
| 178 | 4-Cl | 5-Cl | Me | allyl | H | H | O | 142–145 |
| 179 | 5-CF₃ | 5-CF₃ | Me | Me | H | H | O | 234–236 |

TABLE 4-continued

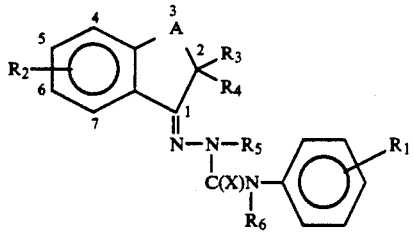

(X = O)

| CMPD | R₁ | R₂ | R₃ | R₄ | R₅ | R₆ | A | m.p. °C. |
|---|---|---|---|---|---|---|---|---|
| 180 | 4-OCF₃ | 5-CF₃ | Me | Me | H | H | O | 196-199 |
| 181 | 4-OCF₃ | 5-Cl | Me | allyl | H | H | O | 128-130 |
| 182 | 4-Cl | H | Me | Me | Me | Me | O | 155-158 |
| 183 | 4-Cl | H | Me | Me | Me | H | O | wax |
| 184 | 4-CF₃ | H | Ph | Me | Me | Me | O | 128-130 |
| 185 | 4-CF₃ | H | Me | Me | H | H | S | 193-197 |
| 186 | 4-Cl | H | Me | Me | Me | Me | S | 192-193 |

TABLE 5

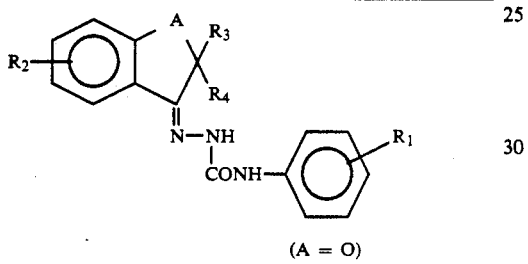

(A = O)

| CMPD | R₁ | R₂ | R₃ | R₄ | syn/anti | m.p. °C. |
|---|---|---|---|---|---|---|
| 187 | 4-CF₃ | H | Me | H | syn | 179-180 |
| 188 | 4-CF₃ | H | Me | H | anti | 212-213 |
| 189 | 4-CF₃ | 5-Cl | Me | H | syn | 196-198 |
| 190 | 4-CF₃ | 5-Cl | Me | H | anti | 205-207 |
| 191 | 4-Br | H | Me | H | mix | 193-196 |
| 192 | 4-Br | 5-Cl | Me | H | mix | 195-200 |
| 193 | 4-CF₃ | H | i-Pr | H | syn | 201-202 |
| 194 | 4-CF₃ | H | i-Pr | H | anti | 181-183 |
| 195 | 4-Cl | H | i-Pr | H | syn | 151-153 |
| 196 | 4-Cl | H | i-Pr | H | mix | 203-205 |
| 197 | 4-Br | H | i-Pr | H | mix | 200-205 |
| 198 | 4-CF₃ | 5-Cl | i-Pr | H | syn | 195-196 |
| 199 | 4-Br | 5-Cl | i-Pr | H | mix | 197-199 |
| 200 | 4-Cl | 5-Cl | i-Pr | H | anti | 192-196 |
| 201 | 4-CF₃ | 5-Cl | i-Pr | H | mix | 196-200 |

TABLE 6

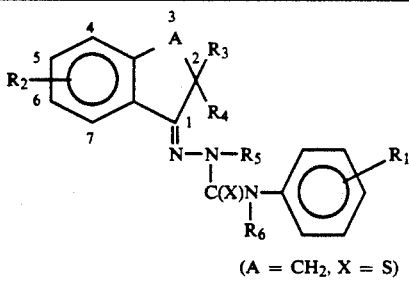

(A = CH₂, X = S)

| CMPD | R₁ | R₂ | R₃ | R₄ | R₅ | R₆ | m.p. °C. |
|---|---|---|---|---|---|---|---|
| 202 | 4-CF₃ | 5-F | 4-F—Ph | H | H | H | 192-194 |
| 203 | 4-CF₃ | 5-F | Ph | H | H | H | 154-156 |
| 204 | 4-Cl | 5-F | 4-F—Ph | H | H | H | 182-184 |
| 205 | 4-Br | 5-Cl | Ph | H | H | H | 192-194 |

TABLE 7

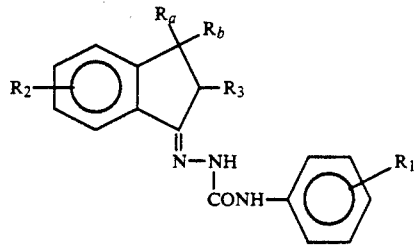

| CMPD | R₁ | R₂ | R₃ | Rₐ | R_b | m.p. °C. |
|---|---|---|---|---|---|---|
| 206 | 4-CF₃ | 5-F | 4-F—Ph | Me | H | 218-220 |
| 207 | 4-CF₃ | 5-Cl | H | i-Pr | H | 238-240 |
| 208 | 4-CF₃ | 5-F | H | Me | H | 241-243 |
| 209 | 4-OCF₃ | 5-F | H | Me | H | 211-213 |
| 210 | 4-CF₃ | H | H | Me | Me | 222-223 |
| 211 | 4-Cl | H | H | Me | Me | 215-216 |
| 212 | 4-CF₃ | 5-F | H | Me | Me | 198-201 |
| 213 | 4-F | 5-F | H | Me | Me | 201.5-205 |
| 214 | 4-CF₃ | H | H | Ph | H | 248.5-250 |
| 215 | 4-Cl | H | H | Ph | H | 253-254 |
| 216 | 4-CF₃ | H | H | Ph | Me | 207-209 |
| 217 | 4-Cl | H | H | Ph | Me | 203-205 |
| 218 | 4-CF₃ | H | H | 4-Cl—Ph | H | 243.5-245 |
| 219 | 4-Cl | H | H | 4-Cl—Ph | H | 242.5-244 |
| 220 | 4-CF₃ | 5-Cl | H | Ph | H | 246-248 |
| 221 | 4-Br | 5-Cl | H | Ph | H | 256-258 |
| 222 | 4-CF₃ | 5-Cl | H | 4-Cl—Ph | H | 235-238 |
| 223 | 4-Br | 5-Cl | H | 4-Cl—Ph | H | 260-262 |
| 224 | 4-CF₃ | H | H | 4-F—Ph | H | 253-255 |
| 225 | 4-Cl | H | H | 4-F—Ph | H | 249-250 |
| 226 | 4-F | H | H | 4-F—Ph | H | 244-246 |
| 227 | 4-CF₃ | 5-F | H | Ph | H | >250 |
| 228 | 4-Cl | 5-F | H | Ph | H | >250 |
| 229 | 4-CF₃ | 4-Cl | H | 4-F—Ph | H | 252.5-253 |
| 230 | 4-Cl | 4-Cl | H | 4-F—Ph | H | 260-261 |
| 231 | 4-CF₃ | 4-Cl | H | 4-F—Ph | Me | 176-179 |
| 232 | 4-CF₃ | 4-F | H | 4-F—Ph | H | 242-244 |
| 233 | 4-Cl | 4-F | H | 4-F—Ph | H | 248-250 |

TABLE 8

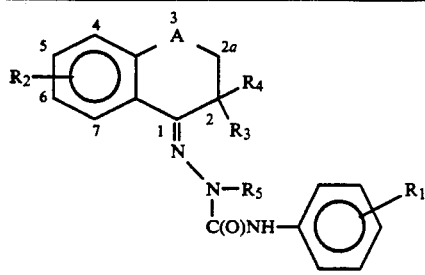

| CMPD | R1 | R2 | R3 | R4 | R5 | A | m.p. °C. |
|---|---|---|---|---|---|---|---|
| 234 | 4-Cl | 5-Cl | Ph | H | H | O | 180–182 |
| 235 | 4-Br | 5-Cl | Ph | H | H | O | 189–191 |
| 236 | 4-CF3 | 5-Cl | Ph | H | H | O | 211–212 |
| 237 | 4-Cl | 5-Cl | 4-F—Ph | H | H | O | 171–173 |
| 238 | 4-Br | 5-Cl | 4-F—Ph | H | H | O | 187–189 |
| 239 | 4-CF3 | 5-Cl | 4-F—Ph | H | H | O | 180–185 |
| 240 | 4-CF3 | 5-F | Ph | H | H | O | 197–200 |
| 241 | 4-Br | 5-F | 4-F—Ph | H | H | O | glass |
| 242 | 4-CF3 | 5-F | 4-F—Ph | H | H | O | glass |
| 243 | 4-Cl | 5-Cl | 4-F—Ph | H | H | S | 216–218 |
| 244 | 4-Br | 5-Cl | 4-F—Ph | H | H | S | 219–221 |
| 245 | 4-CF3 | 5-Cl | 4-F—Ph | H | H | S | >220 |
| 246 | 4-Cl | 5-Cl | Ph | H | H | S | 194–196 |
| 247 | 4-Br | 5-Cl | Ph | H | H | S | 210–212 |
| 248 | 4-CF3 | 5-Cl | Ph | H | H | S | 205–208 |
| 249 | 4-Cl | 5-Cl | 4-Cl—Ph | H | H | S | 184–186 |
| 250 | 4-Br | 5-Cl | 4-Cl—Ph | H | H | S | 199–201 |
| 251 | 4-CF3 | 5-Cl | 4-Cl—Ph | H | H | S | 207–210 |
| 252 | 4-Cl | 4-F | 4-F—Ph | H | H | S | 216–218 |
| 253 | 4-Br | 4-F | 4-F—Ph | H | H | S | 218–220 |
| 254 | 4-CF3 | 4-F | 4-F—Ph | H | H | S | 217–219 |
| 255 | 4-Cl | 4-F | Ph | H | H | S | 195–197 |
| 256 | 4-CF3 | 4-F | Ph | H | H | S | 208–210 |
| 257 | 4-Cl | 5-F | 4-F—Ph | H | H | S | 209–211 |
| 258 | 4-Br | 5-F | 4-F—Ph | H | H | S | 215–217 |
| 259 | 4-CF3 | 5-F | 4-F—Ph | H | H | S | 202–204 |
| 260 | 4-CF3 | H | H | H | H | C(Me)2 | 206–210 |
| 261 | 4-Cl | H | H | H | H | C(Me)2 | 208–212 |
| 262 | 4-OMe | H | H | H | H | C(Me)2 | 177–180 |
| 263 | 4-CF3 | H | H | H | H | S | 230–235 |

TABLE 9

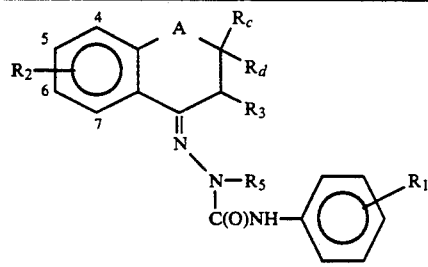

| CMPD | R1 | R2 | R3 | R5 | Rc | Rd | A | m.p. °C. |
|---|---|---|---|---|---|---|---|---|
| 264 | 4-CF3 | 5-Cl | H | H | Me | Me | S | 151–153 |
| 265 | 4-CF3 | 5-Cl | H | Me | Me | H | S | >250 |
| 266 | 4-CF3 | 5-Cl | H | H | H | Me | S | 234–235 |
| 267 | 4-CF3 | 5-Cl | H | H | Me | Me | O | 253–255 |

TABLE 10

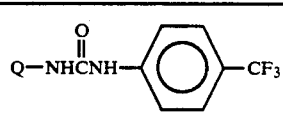

| CMPD | Q | V | A | R2 | R3 | R4 | m.p. °C. |
|---|---|---|---|---|---|---|---|
| 268 | Q-5 | — | CH2CH2 | H | H | H | 173–174 |

TABLE 10-continued

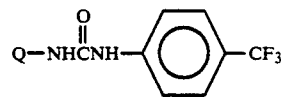

| CMPD | Q | V | A | R2 | R3 | R4 | m.p. °C. |
|---|---|---|---|---|---|---|---|
| 269 | Q-6 | S | CH2CH2 | H | H | H | 248–249 |

TABLE 11

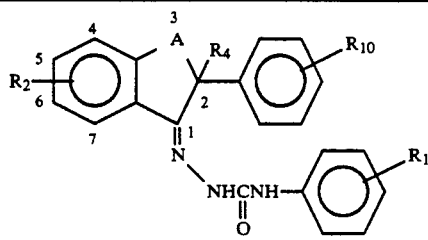

| R1 | R2 | R4 | R10 | A |
|---|---|---|---|---|
| 4-F | 4-F | H | H | CH2 |
| 4-Cl | 4-F | H | H | CH2 |
| 4-OCF3 | 4-F | H | H | CH2 |
| 4-OCF2H | 4-F | H | H | CH2 |
| 3,4-di-Cl | 4-F | H | H | CH2 |
| 4-CN | 4-Cl | H | H | CH2 |
| 4-CO2Me | 4-Cl | H | H | CH2 |
| 4-OCF2H | 4-Cl | H | H | CH2 |
| 4-OCF3 | 4-Cl | H | H | CH2 |
| 4-F | 5-F | H | H | CH2 |
| 4-OCF2H | 5-F | H | H | CH2 |
| 4-OCF2CF2H | 5-F | H | H | CH2 |
| 4-NO2 | 5-F | H | H | CH2 |
| 4-SCF2H | 5-F | H | H | CH2 |
| 4-CN | 5-F | H | H | CH2 |
| 3,4-CF2CF2O | 5-F | H | H | CH2 |
| 3,4-CH2C(Me)2O | 5-F | H | H | CH2 |
| 4-F | 5-Cl | H | H | CH2 |
| 4-Cl | 5-Cl | H | H | CH2 |
| 4-OCF2H | 5-Cl | H | H | CH2 |
| 4-NO2 | 5-Cl | H | H | CH2 |
| 4-SCF2H | 5-Cl | H | H | CH2 |
| 4-CN | 5-Cl | H | H | CH2 |
| 3,4-CF2CF2O | 5-Cl | H | H | CH2 |
| 3,4-CH2C(Me)2O | 5-Cl | H | H | CH2 |
| 4-Cl | 5-Br | H | H | CH2 |
| 4-Br | 5-Br | H | H | CH2 |
| 4-CF3 | 5-Br | H | H | CH2 |
| 4-OCF2H | 5-Br | H | H | CH2 |
| 4-OCF3 | 5-Br | H | H | CH2 |
| 4-Cl | 5-CN | H | H | CH2 |
| 4-Br | 5-CN | H | H | CH2 |
| 4-CF3 | 5-CN | H | H | CH2 |
| 4-OCF2H | 5-CN | H | H | CH2 |
| 4-OCF3 | 5-CN | H | H | CH2 |
| 4-Cl | 5-OMe | H | H | CH2 |
| 4-Br | 5-OMe | H | H | CH2 |
| 4-CF3 | 5-CF3 | H | H | CH2 |
| 4-Cl | 5-CF3 | H | H | CH2 |
| 4-Br | 5-CF3 | H | H | CH2 |
| 4-OCF3 | 5-CF3 | H | H | CH2 |
| 4-OCF2H | 5-CF3 | H | H | CH2 |
| 4-OCF2H | 5-OCF2H | H | H | CH2 |
| 4-OCF3 | 5-OCF2H | H | H | CH2 |
| 4-CF3 | 5-OCF2H | H | H | CH2 |
| 4-Cl | 5-OCF2H | H | H | CH2 |
| 4-Br | 5-OCF2H | H | H | CH2 |
| 4-OCF2H | 5-OCF3 | H | H | CH2 |
| 4-OCF3 | 5-OCF3 | H | H | CH2 |
| 4-CF3 | 5-OCF3 | H | H | CH2 |
| 4-Cl | 5-OCF3 | H | H | CH2 |
| 4-Br | 5-OCF3 | H | H | CH2 |
| 4-OCF2H | 5-OPh | H | H | CH2 |
| 4-OCF3 | 5-OPh | H | H | CH2 |
| 4-CF3 | 5-OPh | H | H | CH2 |
| 4-Cl | 5-OPh | H | H | CH2 |

TABLE 11-continued

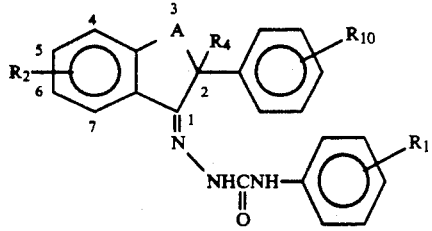
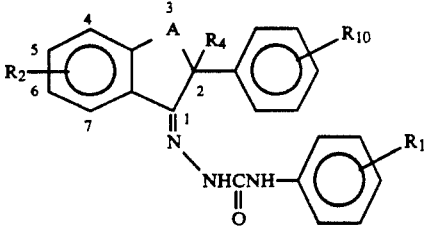

| R₁ | R₂ | R₄ | R₁₀ | A |
|---|---|---|---|---|
| 4-Br | 5-OPh | H | H | CH₂ |
| 4-CF₃ | 5-SMe | H | H | CH₂ |
| 4-Cl | 5-SMe | H | H | CH₂ |
| 4-Br | 5-SMe | H | H | CH₂ |
| 4-CF₃ | 6-F | H | H | CH₂ |
| 4-Cl | 6-F | H | H | CH₂ |
| 4-Br | 6-F | H | H | CH₂ |
| 4-CF₃ | 6-Cl | H | H | CH₂ |
| 4-Cl | 6-Cl | H | H | CH₂ |
| 4-Br | 6-Cl | H | H | CH₂ |
| 4-SCF₂H | 5-F | H | 4-F | CH₂ |
| 4-F | 5-F | H | 4-F | CH₂ |
| 4-CN | 5-F | H | 4-F | CH₂ |
| 4-OCF₂CF₂H | 5-F | H | 4-F | CH₂ |
| 4-OCF₃ | 5-F | H | 4-F | CH₂ |
| 3,4-di-Cl | 5-F | H | 4-F | CH₂ |
| 3,4-CF₂CF₂O | 5-F | H | 4-F | CH₂ |
| 3,4-CH₂C(Me)₂O | 5-F | H | 4-F | CH₂ |
| 4-OCF₂H | 5-F | H | 4-Cl | CH₂ |
| 4-OCF₃ | 5-F | H | 4-Cl | CH₂ |
| 4-Cl | 5-F | H | 4-NO₂ | CH₂ |
| 4-Br | 5-F | H | 4-NO₂ | CH₂ |
| 4-CF₃ | 5-F | H | 4-NO₂ | CH₂ |
| 4-OCF₂H | 5-F | H | 4-NO₂ | CH₂ |
| 4-OCF₃ | 5-F | H | 4-NO₂ | CH₂ |
| 4-Cl | 5-F | H | 4-CN | CH₂ |
| 4-Br | 5-F | H | 4-CN | CH₂ |
| 4-CF₃ | 5-F | H | 4-CN | CH₂ |
| 4-OCF₂H | 5-F | H | 4-CN | CH₂ |
| 4-OCF₃ | 5-F | H | 4-CN | CH₂ |
| 4-Cl | 5-F | H | 4-OMe | CH₂ |
| 4-Br | 5-F | H | 4-OMe | CH₂ |
| 4-CF₃ | 5-F | H | 4-OMe | CH₂ |
| 4-OCF₂H | 5-F | H | 4-OMe | CH₂ |
| 4-OCF₃ | 5-F | H | 4-OMe | CH₂ |
| 4-Cl | 5-F | H | 4-CF₃ | CH₂ |
| 4-Br | 5-F | H | 4-CF₃ | CH₂ |
| 4-CF₃ | 5-F | H | 4-CF₃ | CH₂ |
| 4-OCF₃ | 5-F | H | 4-CF₃ | CH₂ |
| 4-OCF₂H | 5-F | H | 4-CF₃ | CH₂ |
| 4-CF₃ | 5-F | H | 4-OCF₂H | CH₂ |
| 4-Cl | 5-F | H | 4-OCF₂H | CH₂ |
| 4-Br | 5-F | H | 4-OCF₂H | CH₂ |
| 4-OCF₂H | 5-F | H | 4-OCF₂H | CH₂ |
| 4-OCF₃ | 5-F | H | 4-OCF₂H | CH₂ |
| 4-OCF₂CF₂H | 5-Cl | H | 4-F | CH₂ |
| 4-F | 5-Cl | H | 4-F | CH₂ |
| 4-OCF₃ | 5-Cl | H | 4-F | CH₂ |
| 4-OCF₂H | 5-Cl | H | 4-F | CH₂ |
| 4-NO₂ | 5-Cl | H | 4-F | CH₂ |
| 3,4-di-Cl | 5-Cl | H | 4-F | CH₂ |
| 3,4-CH₂C(Me)₂O | 5-Cl | H | 4-F | CH₂ |
| 3,4-CF₂CF₂O | 5-Cl | H | 4-F | CH₂ |
| 4-OCF₃ | 5-Cl | H | 4-Cl | CH₂ |
| 4-OCF₂H | 5-Cl | H | 4-Cl | CH₂ |
| 3,4-CF₂CF₂O | 5-Cl | H | 4-Cl | CH₂ |
| 3,4-CH₂C(Me)₂O | 5-Cl | H | 4-Cl | CH₂ |
| 4-CN | 5-Cl | H | 4-Cl | CH₂ |
| 4-F | 5-Cl | H | 4-Cl | CH₂ |
| 4-NO₂ | 5-Cl | H | 4-Cl | CH₂ |
| H | 5-Cl | H | 4-Cl | CH₂ |
| 4-CF₃ | 5-CF₃ | H | 4-F | CH₂ |
| 4-OCF₃ | 5-CF₃ | H | 4-F | CH₂ |
| 4-Cl | 5-CF₃ | H | 4-F | CH₂ |
| 4-Br | 5-CF₃ | H | 4-F | CH₂ |
| 4-OCF₂H | 5-CF₃ | H | 4-F | CH₂ |
| 4-CF₃ | 5-CF₃ | H | 4-Cl | CH₂ |
| 4-OCF₃ | 5-CF₃ | H | 4-Cl | CH₂ |
| 4-Cl | 5-CF₃ | H | 4-Cl | CH₂ |
| 4-Br | 5-CF₃ | H | 4-Cl | CH₂ |
| 4-OCF₂H | 5-CF₃ | H | 4-Cl | CH₂ |
| 4-CF₃ | 5-OCF₂H | H | 4-F | CH₂ |
| 4-Cl | 5-OCF₂H | H | 4-F | CH₂ |
| 4-Br | 5-OCF₂H | H | 4-F | CH₂ |
| 4-OCF₃ | 5-OCF₂H | H | 4-F | CH₂ |
| 4-CF₃ | 5-OCF₂H | H | 4-Cl | CH₂ |
| 4-Cl | 5-OCF₂H | H | 4-Cl | CH₂ |
| 4-Br | 5-OCF₂H | H | 4-Cl | CH₂ |
| 4-OCF₃ | 5-OCF₂H | H | 4-Cl | CH₂ |
| 4-CF₃ | 4-F | H | 4-F | CH₂ |
| 4-Cl | 4-F | H | 4-F | CH₂ |
| 4-Br | 4-F | H | 4-F | CH₂ |
| 4-OCF₃ | 4-F | H | 4-F | CH₂ |
| 4-CF₃ | 4-F | H | 4-Cl | CH₂ |
| 4-Cl | 4-F | H | 4-Cl | CH₂ |
| 4-Br | 4-F | H | 4-Cl | CH₂ |
| 4-CF₃ | 4-Cl | H | 4-Cl | CH₂ |
| 4-Cl | 4-Cl | H | 4-Cl | CH₂ |
| 4-Br | 4-Cl | H | 4-Cl | CH₂ |
| 4-OCF₃ | 4-Cl | H | 4-Cl | CH₂ |
| 4-CF₃ | 4-Cl | H | 4-F | CH₂ |
| 4-Cl | 4-Cl | H | 4-F | CH₂ |
| 4-Br | 4-Cl | H | 4-F | CH₂ |
| 4-OCF₃ | 4-Cl | H | 4-F | CH₂ |
| 4-CF₃ | 5-Cl | H | 4-CF₃ | CH₂ |
| 4-Cl | 5-Cl | H | 4-CF₃ | CH₂ |
| 4-Br | 5-Cl | H | 4-CF₃ | CH₂ |
| 4-OCF₃ | 5-Cl | H | 4-CF₃ | CH₂ |
| 4-OCF₂H | 5-Cl | H | 4-CF₃ | CH₂ |
| 4-CF₃ | 5-Cl | H | 4-SMe | CH₂ |
| 4-Cl | 5-Cl | H | 4-SMe | CH₂ |
| 4-Br | 5-Cl | H | 4-SMe | CH₂ |
| 4-OCF₃ | 5-Cl | H | 4-SMe | CH₂ |
| 4-CF₃ | 5-Cl | H | 4-NO₂ | CH₂ |
| 4-Cl | 5-Cl | H | 4-NO₂ | CH₂ |
| 4-Br | 5-Cl | H | 4-NO₂ | CH₂ |
| 4-OCF₂H | 5-Cl | H | 4-NO₂ | CH₂ |
| 4-CF₃ | 5-Cl | H | 4-OMe | CH₂ |
| 4-Cl | 5-Cl | H | 4-OMe | CH₂ |
| 4-Br | 5-Cl | H | 4-OMe | CH₂ |
| 4-OCF₂H | 5-Cl | H | 4-OMe | CH₂ |
| 4-CF₃ | 5-Cl | H | 4-OPh | CH₂ |
| 4-Cl | 5-Cl | H | 4-OPh | CH₂ |
| 4-Br | 5-Cl | H | 4-OPh | CH₂ |
| 4-OCF₂H | 5-Cl | H | 4-OPh | CH₂ |
| 4-CF₃ | 5-Cl | H | 4-CN | CH₂ |
| 4-Cl | 5-Cl | H | 4-CN | CH₂ |
| 4-Br | 5-Cl | H | 4-CN | CH₂ |
| 4-OCF₂H | 5-Cl | H | 4-CN | CH₂ |
| 4-CF₃ | 5-Cl | H | 4-CO₂Me | CH₂ |
| 4-Cl | 5-Cl | H | 4-CO₂Me | CH₂ |
| 4-Br | 5-Cl | H | 4-CO₂Me | CH₂ |
| 4-CF₃ | H | Me | H | CH₂ |
| 4-Cl | H | Me | H | CH₂ |
| 4-Br | H | Me | H | CH₂ |
| 4-OCF₂H | H | Me | H | CH₂ |
| 4-OCF₃ | H | Me | H | CH₂ |
| 4-CF₃ | 4-F | Me | H | CH₂ |
| 4-Cl | 4-F | Me | H | CH₂ |
| 4-Br | 4-F | Me | H | CH₂ |
| 4-OCF₂H | 4-F | Me | H | CH₂ |
| 4-OCF₃ | 4-F | Me | H | CH₂ |
| 4-CF₃ | 4-Cl | Me | H | CH₂ |
| 4-Cl | 4-Cl | Me | H | CH₂ |
| 4-Br | 4-Cl | Me | H | CH₂ |
| 4-OCF₂H | 4-Cl | Me | H | CH₂ |
| 4-OCF₂H | 4-Cl | Me | H | CH₂ |
| 4-CF₃ | 5-F | Me | H | CH₂ |

TABLE 11-continued

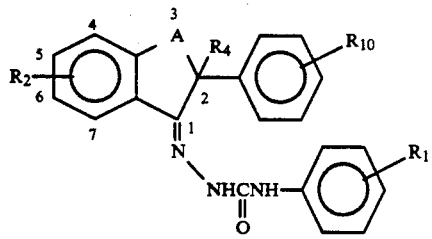

| R₁ | R₂ | R₄ | R₁₀ | A |
|---|---|---|---|---|
| 4-Cl | 5-F | Me | H | CH₂ |
| 4-Br | 5-F | Me | H | CH₂ |
| 4-OCF₂H | 5-F | Me | H | CH₂ |
| 4-CF₃ | 5-Cl | Me | H | CH₂ |
| 4-Cl | 5-Cl | Me | H | CH₂ |
| 4-Br | 5-Cl | Me | H | CH₂ |
| 4-OCF₂H | 5-Cl | Me | H | CH₂ |
| 4-CF₃ | 4-F | Me | 4-F | CH₂ |
| 4-Cl | 4-F | Me | 4-F | CH₂ |
| 4-Br | 4-F | Me | 4-F | CH₂ |
| 4-OCF₂H | 4-F | Me | 4-F | CH₂ |
| 4-CF₃ | 4-Cl | Me | 4-F | CH₂ |
| 4-Cl | 4-Cl | Me | 4-F | CH₂ |
| 4-Br | 4-Cl | Me | 4-F | CH₂ |
| 4-OCF₂H | 4-Cl | Me | 4-F | CH₂ |
| 4-CF₃ | 5-F | Me | 4-F | CH₂ |
| 4-Cl | 5-F | Me | 4-F | CH₂ |
| 4-Br | 5-F | Me | 4-F | CH₂ |
| 4-OCF₂H | 5-F | Me | 4-F | CH₂ |
| 4-CF₃ | 5-Cl | Me | 4-F | CH₂ |
| 4-Cl | 5-Cl | Me | 4-F | CH₂ |
| 4-Br | 5-Cl | Me | 4-F | CH₂ |
| 4-OCF₂H | 5-Cl | Me | 4-F | CH₂ |
| 4-CF₃ | 4-F | Me | 4-Cl | CH₂ |
| 4-Cl | 4-F | Me | 4-Cl | CH₂ |
| 4-Br | 4-F | Me | 4-Cl | CH₂ |
| 4-OCF₂H | 4-F | Me | 4-Cl | CH₂ |
| 4-CF₃ | 4-Cl | Me | 4-Cl | CH₂ |
| 4-Cl | 4-Cl | Me | 4-Cl | CH₂ |
| 4-Br | 4-Cl | Me | 4-Cl | CH₂ |
| 4-OCF₂H | 4-Cl | Me | 4-Cl | CH₂ |
| 4-CF₃ | 5-F | Me | 4-Cl | CH₂ |
| 4-Cl | 5-F | Me | 4-Cl | CH₂ |
| 4-Br | 5-F | Me | 4-Cl | CH₂ |
| 4-OCF₂H | 5-F | Me | 4-Cl | CH₂ |
| 4-CF₃ | 5-Cl | Me | 4-Cl | CH₂ |
| 4-Cl | 5-Cl | Me | 4-Cl | CH₂ |
| 4-Br | 5-Cl | Me | 4-Cl | CH₂ |
| 4-OCF₂H | 5-Cl | Me | 4-Cl | CH₂ |
| 4-CF₃ | 5-Cl | Et | 4-F | CH₂ |
| 4-Cl | 5-Cl | Et | 4-F | CH₂ |
| 4-Br | 5-Cl | Et | 4-F | CH₂ |
| 4-CF₃ | 5-Cl | Et | 4-Cl | CH₂ |
| 4-Cl | 5-Cl | Et | 4-Cl | CH₂ |
| 4-Br | 5-Cl | Et | 4-Cl | CH₂ |
| 4-CF₃ | 5-Cl | allyl | 4-F | CH₂ |
| 4-Cl | 5-Cl | allyl | 4-F | CH₂ |
| 4-Br | 5-Cl | allyl | 4-F | CH₂ |
| 4-CF₃ | 5-Cl | allyl | 4-Cl | CH₂ |
| 4-Cl | 5-Cl | allyl | 4-Cl | CH₂ |
| 4-Br | 5-Cl | allyl | 4-Cl | CH₂ |
| 4-CF₃ | 5-Cl | propargyl | 4-F | CH₂ |
| 4-Cl | 5-Cl | propargyl | 4-F | CH₂ |
| 4-Br | 5-Cl | propargyl | 4-F | CH₂ |
| 4-CF₃ | 5-Cl | propargyl | 4-Cl | CH₂ |
| 4-Cl | 5-Cl | propargyl | 4-Cl | CH₂ |
| 4-Br | 5-Cl | propargyl | 4-Cl | CH₂ |
| 4-CF₃ | 5-F | H | 4-F | O |
| 4-OCF₃ | 5-F | H | 4-F | O |
| 4-CF₃ | 4-F | H | 4-F | O |
| 4-OCF₃ | 4-F | H | 4-F | O |
| 4-OCF₃ | 5-Cl | H | 4-F | O |
| 4-OCF₃ | 5-Cl | H | 4-F | O |
| 4-CF₃ | 5-CF₃ | H | 4-F | O |
| 4-OCF₃ | 5-CF₃ | H | 4-F | O |
| 4-CF₃ | 5-F | H | 4-F | S |
| 4-OCF₃ | 5-F | H | 4-F | S |
| 4-CF₃ | 4-F | H | 4-F | S |
| 4-OCF₃ | 4-F | H | 4-F | S |
| 4-CF₃ | 5-Cl | H | 4-F | S |
| 4-OCF₃ | 5-Cl | H | 4-F | S |
| 4-CF₃ | 5-CF₃ | H | 4-F | S |
| 4-OCF₃ | 5-CF₃ | H | 4-F | S |
| 4-CF₃ | H | Me | H | O |
| 4-Cl | H | Me | H | O |
| 4-Br | H | Me | H | O |
| 4-OCF₂H | H | Me | H | O |
| 4-OCF₃ | H | Me | H | O |
| 4-CF₃ | 4-F | Me | H | O |
| 4-Cl | 4-F | Me | H | O |
| 4-Br | 4-F | Me | H | O |
| 4-OCF₂H | 4-F | Me | H | O |
| 4-OCF₃ | 4-F | Me | H | O |
| 4-CF₃ | 4-Cl | Me | H | O |
| 4-Cl | 4-Cl | Me | H | O |
| 4-Br | 4-Cl | Me | H | O |
| 4-OCF₂H | 4-Cl | Me | H | O |
| 4-OCF₃ | 4-Cl | Me | H | O |
| 4-CF₃ | 5-F | Me | H | O |
| 4-Cl | 5-F | Me | H | O |
| 4-Br | 5-F | Me | H | O |
| 4-OCF₂H | 5-F | Me | H | O |
| 4-CF₃ | 5-Cl | Me | H | O |
| 4-Cl | 5-Cl | Me | H | O |
| 4-Br | 5-Cl | Me | H | O |
| 4-OCF₃ | 5-Cl | Me | H | O |
| 4-OCF₂H | 5-Cl | Me | H | O |
| 4-CF₃ | 4-F | Me | 4-F | O |
| 4-Cl | 4-F | Me | 4-F | O |
| 4-Br | 4-F | Me | 4-F | O |
| 4-OCF₃ | 4-F | Me | 4-F | O |
| 4-OCF₂H | 4-F | Me | 4-F | O |
| 4-CF₃ | 4-Cl | Me | 4-F | O |
| 4-Cl | 4-Cl | Me | 4-F | O |
| 4-Br | 4-Cl | Me | 4-F | O |
| 4-OCF₃ | 4-Cl | Me | 4-F | O |
| 4-OCF₂H | 4-Cl | Me | 4-F | O |
| 4-CF₃ | 5-F | Me | 4-F | O |
| 4-Cl | 5-F | Me | 4-F | O |
| 4-Br | 5-F | Me | 4-F | O |
| 4-OCF₃ | 5-F | Me | 4-F | O |
| 4-OCF₂H | 5-F | Me | 4-F | O |
| 4-CF₃ | 5-Cl | Me | 4-F | O |
| 4-Cl | 5-Cl | Me | 4-F | O |
| 4-Br | 5-Cl | Me | 4-F | O |
| 4-OCF₃ | 5-Cl | Me | 4-F | O |
| 4-OCF₂H | 5-Cl | Me | 4-F | O |
| 4-CF₃ | 4-F | Me | 4-Cl | O |
| 4-Cl | 4-F | Me | 4-Cl | O |
| 4-Br | 4-F | Me | 4-Cl | O |
| 4-OCF₃ | 4-F | Me | 4-Cl | O |
| 4-OCF₂H | 4-F | Me | 4-Cl | O |
| 4-CF₃ | 4-Cl | Me | 4-Cl | O |
| 4-Cl | 4-Cl | Me | 4-Cl | O |
| 4-Br | 4-Cl | Me | 4-Cl | O |
| 4-OCF₃ | 4-Cl | Me | 4-Cl | O |
| 4-OCF₂H | 4-Cl | Me | 4-Cl | O |
| 4-CF₃ | 5-F | Me | 4-Cl | O |
| 4-Cl | 5-F | Me | 4-Cl | O |
| 4-Br | 5-F | Me | 4-Cl | O |
| 4-OCF₃ | 5-F | Me | 4-Cl | O |
| 4-OCF₂H | 5-F | Me | 4-Cl | O |
| 4-CF₃ | 5-Cl | Me | 4-Cl | O |
| 4-Cl | 5-Cl | Me | 4-Cl | O |

TABLE 11-continued

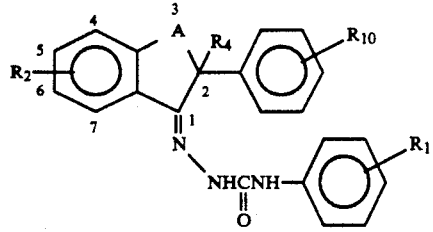

| R₁ | R₂ | R₄ | R₁₀ | A |
|---|---|---|---|---|
| 4-Br | 5-Cl | Me | 4-Cl | O |
| 4-OCF₂H | 5-Cl | Me | 4-Cl | O |
| 4-OCF₃ | 5-Cl | Me | 4-Cl | O |
| 4-CF₃ | 5-Cl | Me | 4-Cl | O |
| 4-Cl | 5-Cl | Me | 4-Cl | O |
| 4-Br | 5-Cl | Me | 4-Cl | O |
| 4-OCF₃ | 5-Cl | Me | 4-Cl | O |
| 4-OCF₂H | 5-Cl | Me | 4-Cl | O |
| 4-CF₃ | 5-Cl | Et | 4-F | O |
| 4-Cl | 5-Cl | Et | 4-F | O |
| 4-Br | 5-Cl | Et | 4-F | O |
| 4-CF₃ | 5-Cl | Et | 4-Cl | O |
| 4-Cl | 5-Cl | Et | 4-Cl | O |
| 4-Br | 5-Cl | Et | 4-Cl | O |
| 4-CF₃ | 5-Cl | allyl | 4-F | O |
| 4-Cl | 5-Cl | allyl | 4-F | O |
| 4-Br | 5-Cl | allyl | 4-F | O |
| 4-CF₃ | 5-Cl | allyl | 4-Cl | O |
| 4-Cl | 5-Cl | allyl | 4-Cl | O |
| 4-Br | 5-Cl | allyl | 4-Cl | O |
| 4-CF₃ | 5-Cl | propargyl | 4-F | O |
| 4-Cl | 5-Cl | propargyl | 4-F | O |
| 4-Br | 5-Cl | propargyl | 4-F | O |
| 4-CF₃ | 5-Cl | propargyl | 4-Cl | O |
| 4-Cl | 5-Cl | propargyl | 4-Cl | O |
| 4-Br | 5-Cl | propargyl | 4-Cl | O |
| 4-CF₃ | H | Me | H | S |
| 4-Cl | H | Me | H | S |
| 4-Br | H | Me | H | S |
| 4-OCF₂H | H | Me | H | S |
| 4-OCF₃ | H | Me | H | S |
| 4-CF₃ | 4-F | Me | H | S |
| 4-Cl | 4-F | Me | H | S |
| 4-Br | 4-F | Me | H | S |
| 4-OCF₂H | 4-F | Me | H | S |
| 4-OCF₃ | 4-F | Me | H | S |
| 4-CF₃ | 4-Cl | Me | H | S |
| 4-Cl | 4-Cl | Me | H | S |
| 4-Br | 4-Cl | Me | H | S |
| 4-OCF₂H | 4-Cl | Me | H | S |
| 4-OCF₃ | 4-Cl | Me | H | S |
| 4-CF₃ | 5-F | Me | H | S |
| 4-Cl | 5-F | Me | H | S |
| 4-Br | 5-F | Me | H | S |
| 4-OCF₂H | 5-F | Me | H | S |
| 4-CF₃ | 5-Cl | Me | H | S |
| 4-Cl | 5-Cl | Me | H | S |
| 4-Br | 5-Cl | Me | H | S |
| 4-OCF₂H | 5-Cl | Me | H | S |
| 4-CF₃ | 4-F | Me | 4-F | S |
| 4-Cl | 4-F | Me | 4-F | S |
| 4-Br | 4-F | Me | 4-F | S |
| 4-OCF₂H | 4-F | Me | 4-F | S |
| 4-CF₃ | 4-Cl | Me | 4-F | S |
| 4-Cl | 4-Cl | Me | 4-F | S |
| 4-Br | 4-Cl | Me | 4-F | S |
| 4-OCF₂H | 4-Cl | Me | 4-F | S |
| 4-CF₃ | 5-F | Me | 4-F | S |
| 4-Cl | 5-F | Me | 4-F | S |
| 4-Br | 5-F | Me | 4-F | S |
| 4-OCF₂H | 5-F | Me | 4-F | S |
| 4-CF₃ | 5-Cl | Me | 4-F | S |
| 4-Cl | 5-Cl | Me | 4-F | S |
| 4-Br | 5-Cl | Me | 4-F | S |
| 4-OCF₂H | 5-Cl | Me | 4-F | S |
| 4-CF₃ | 4-F | Me | 4-Cl | S |
| 4-Cl | 4-F | Me | 4-Cl | S |
| 4-Br | 4-F | Me | 4-Cl | S |
| 4-OCF₂H | 4-F | Me | 4-Cl | S |

TABLE 11-continued

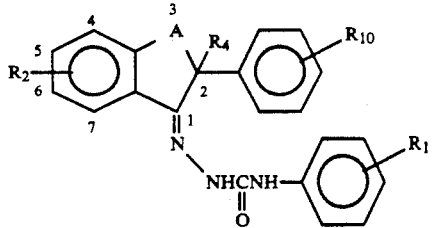

| R₁ | R₂ | R₄ | R₁₀ | A |
|---|---|---|---|---|
| 4-CF₃ | 4-Cl | Me | 4-Cl | S |
| 4-Cl | 4-Cl | Me | 4-Cl | S |
| 4-Br | 4-Cl | Me | 4-Cl | S |
| 4-OCF₂H | 4-Cl | Me | 4-Cl | S |
| 4-CF₃ | 5-F | Me | 4-Cl | S |
| 4-Cl | 5-F | Me | 4-Cl | S |
| 4-Br | 5-F | Me | 4-Cl | S |
| 4-OCF₂H | 5-F | Me | 4-Cl | S |
| 4-CF₃ | 5-Cl | Me | 4-Cl | S |
| 4-Cl | 5-Cl | Me | 4-Cl | S |
| 4-Br | 5-Cl | Me | 4-Cl | S |
| 4-OCF₂H | 5-Cl | Me | 4-Cl | S |
| 4-CF₃ | 5-Cl | Me | 4-Cl | S |
| 4-Cl | 5-Cl | Me | 4-Cl | S |
| 4-Br | 5-Cl | Me | 4-Cl | S |
| 4-OCF₂H | 5-Cl | Me | 4-Cl | S |
| 4-CF₃ | 5-Cl | Et | 4-F | S |
| 4-Cl | 5-Cl | Et | 4-F | S |
| 4-Br | 5-Cl | Et | 4-F | S |
| 4-CF₃ | 5-Cl | Et | 4-Cl | S |
| 4-Cl | 5-Cl | Et | 4-Cl | S |
| 4-Br | 5-Cl | Et | 4-Cl | S |
| 4-CF₃ | 5-Cl | allyl | 4-F | S |
| 4-Cl | 5-Cl | allyl | 4-F | S |
| 4-Br | 5-Cl | allyl | 4-F | S |
| 4-CF₃ | 5-Cl | allyl | 4-Cl | S |
| 4-Cl | 5-Cl | allyl | 4-Cl | S |
| 4-Br | 5-Cl | allyl | 4-Cl | S |
| 4-CF₃ | 5-Cl | propargyl | 4-F | S |
| 4-Cl | 5-Cl | propargyl | 4-F | S |
| 4-Br | 5-Cl | propargyl | 4-F | S |
| 4-CF₃ | 5-Cl | propargyl | 4-Cl | S |
| 4-Cl | 5-Cl | propargyl | 4-Cl | S |
| 4-Br | 5-Cl | propargyl | 4-Cl | S |
| 4-OCF₃ | H | H | H | CH₂CH₂ |
| 4-F | 4-F | H | H | CH₂CH₂ |
| 4-Cl | 4-F | H | H | CH₂CH₂ |
| 4-Br | 4-F | H | H | CH₂CH₂ |
| 4-CF₃ | 4-F | H | H | CH₂CH₂ |
| 4-OCF₃ | 4-F | H | H | CH₂CH₂ |
| 4-OCF₂H | 4-F | H | H | CH₂CH₂ |
| 3,4-di-Cl | 4-F | H | H | CH₂CH₂ |
| 4-CN | 4-Cl | H | H | CH₂CH₂ |
| 4-CO₂Me | 4-Cl | H | H | CH₂CH₂ |
| 4-Cl | 4-Cl | H | H | CH₂CH₂ |
| 4-Br | 4-Cl | H | H | CH₂CH₂ |
| 4-CF₃ | 4-Cl | H | H | CH₂CH₂ |
| 4-OCF₂H | 4-Cl | H | H | CH₂CH₂ |
| 4-OCF₃ | 4-Cl | H | H | CH₂CH₂ |
| 4-OCF₂H | 5-F | H | H | CH₂CH₂ |
| 4-OCF₃ | 5-F | H | H | CH₂CH₂ |
| 4-NO₂ | 5-F | H | H | CH₂CH₂ |
| 4-SCF₂H | 5-F | H | H | CH₂CH₂ |
| 4-CN | 5-F | H | H | CH₂CH₂ |
| 3,4-CF₂CF₂O | 5-F | H | H | CH₂CH₂ |
| 3,4-CH₂C(Me)₂O | 5-F | H | H | CH₂CH₂ |
| 4-F | 5-Cl | H | H | CH₂CH₂ |
| 4-OCF₂H | 5-Cl | H | H | CH₂CH₂ |
| 4-OCF₃ | 5-Cl | H | H | CH₂CH₂ |
| 4-NO₂ | 5-Cl | H | H | CH₂CH₂ |
| 4-SCF₂H | 5-Cl | H | H | CH₂CH₂ |
| 4-CN | 5-Cl | H | H | CH₂CH₂ |
| 3,4-CF₂CF₂O | 5-Cl | H | H | CH₂CH₂ |
| 3,4-CH₂C(Me)₂O | 5-Cl | H | H | CH₂CH₂ |
| 4-Cl | 5-Br | H | H | CH₂CH₂ |
| 4-Br | 5-Br | H | H | CH₂CH₂ |
| 4-CF₃ | 5-Br | H | H | CH₂CH₂ |
| 4-OCF₂H | 5-Br | H | H | CH₂CH₂ |

TABLE 11-continued

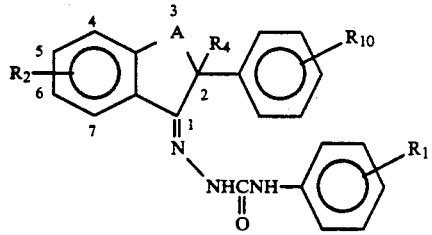

| R₁ | R₂ | R₄ | R₁₀ | A |
|---|---|---|---|---|
| 4-OCF₃ | 5-Br | H | H | CH₂CH₂ |
| 4-Cl | 5-CN | H | H | CH₂CH₂ |
| 4-Br | 5-CN | H | H | CH₂CH₂ |
| 4-CF₃ | 5-CN | H | H | CH₂CH₂ |
| 4-OCF₂H | 5-CN | H | H | CH₂CH₂ |
| 4-OCF₃ | 5-CN | H | H | CH₂CH₂ |
| 4-Cl | 5-OMe | H | H | CH₂CH₂ |
| 4-Br | 5-OMe | H | H | CH₂CH₂ |
| 4-CF₃ | 5-OMe | H | H | CH₂CH₂ |
| 4-OCF₂H | 5-OCF₂H | H | H | CH₂CH₂ |
| 4-OCF₃ | 5-OCF₂H | H | H | CH₂CH₂ |
| 4-CF₃ | 5-OCF₂H | H | H | CH₂CH₂ |
| 4-Cl | 5-OCF₂H | H | H | CH₂CH₂ |
| 4-Br | 5-OCF₂H | H | H | CH₂CH₂ |
| 4-OCF₂H | 5-OCF₃ | H | H | CH₂CH₂ |
| 4-OCF₃ | 5-OCF₃ | H | H | CH₂CH₂ |
| 4-CF₃ | 5-OCF₃ | H | H | CH₂CH₂ |
| 4-Cl | 5-OCF₃ | H | H | CH₂CH₂ |
| 4-Br | 5-OCF₃ | H | H | CH₂CH₂ |
| 4-OCF₂H | 5-OPh | H | H | CH₂CH₂ |
| 4-OCF₃ | 5-OPh | H | H | CH₂CH₂ |
| 4-CF₃ | 5-OPh | H | H | CH₂CH₂ |
| 4-Cl | 5-OPh | H | H | CH₂CH₂ |
| 4-Br | 5-OPh | H | H | CH₂CH₂ |
| 4-CF₃ | 5-SMe | H | H | CH₂CH₂ |
| 4-Cl | 5-SMe | H | H | CH₂CH₂ |
| 4-Br | 5-SMe | H | H | CH₂CH₂ |
| 4-CF₃ | 6-F | H | H | CH₂CH₂ |
| 4-Cl | 6-F | H | H | CH₂CH₂ |
| 4-Br | 6-F | H | H | CH₂CH₂ |
| 4-CF₃ | 6-Cl | H | H | CH₂CH₂ |
| 4-Cl | 6-Cl | H | H | CH₂CH₂ |
| 4-Br | 6-Cl | H | H | CH₂CH₂ |
| 4-Cl | 5-F | H | 4-F | CH₂CH₂ |
| 4-Br | 5-F | H | 4-F | CH₂CH₂ |
| 4-CF₃ | 5-F | H | 4-F | CH₂CH₂ |
| 4-OCF₂H | 5-F | H | 4-F | CH₂CH₂ |
| 4-OCF₃ | 5-F | H | 4-F | CH₂CH₂ |
| 3,4-di-Cl | 5-F | H | 4-F | CH₂CH₂ |
| 3,4-CF₂CF₂O | 5-F | H | 4-F | CH₂CH₂ |
| 3,4-CH₂C(Me)₂O | 5-F | H | 4-F | CH₂CH₂ |
| 4-Cl | 5-F | H | 4-Cl | CH₂CH₂ |
| 4-Br | 5-F | H | 4-Cl | CH₂CH₂ |
| 4-CF₃ | 5-F | H | 4-Cl | CH₂CH₂ |
| 4-OCF₂H | 5-F | H | 4-Cl | CH₂CH₂ |
| 4-OCF₃ | 5-F | H | 4-Cl | CH₂CH₂ |
| 4-Cl | 5-F | H | 4-NO₂ | CH₂CH₂ |
| 4-Br | 5-F | H | 4-NO₂ | CH₂CH₂ |
| 4-CF₃ | 5-F | H | 4-NO₂ | CH₂CH₂ |
| 4-OCF₂H | 5-F | H | 4-NO₂ | CH₂CH₂ |
| 4-OCF₃ | 5-F | H | 4-NO₂ | CH₂CH₂ |
| 4-Cl | 5-F | H | 4-CN | CH₂CH₂ |
| 4-Br | 5-F | H | 4-CN | CH₂CH₂ |
| 4-CF₃ | 5-F | H | 4-CN | CH₂CH₂ |
| 4-OCF₂H | 5-F | H | 4-CN | CH₂CH₂ |
| 4-OCF₃ | 5-F | H | 4-CN | CH₂CH₂ |
| 4-Cl | 5-F | H | 4-CF₃ | CH₂CH₂ |
| 4-Br | 5-F | H | 4-CF₃ | CH₂CH₂ |
| 4-CF₃ | 5-F | H | 4-CF₃ | CH₂CH₂ |
| 4-OCF₂H | 5-F | H | 4-CF₃ | CH₂CH₂ |
| 4-CF₃ | 5-F | H | 4-OCF₂H | CH₂CH₂ |
| 4-Cl | 5-F | H | 4-OCF₂H | CH₂CH₂ |
| 4-Br | 5-F | H | 4-OCF₂H | CH₂CH₂ |
| 4-OCF₂H | 5-F | H | 4-OCF₂H | CH₂CH₂ |
| 4-OCF₃ | 5-F | H | 4-OCF₂H | CH₂CH₂ |
| 4-CF₃ | 5-Cl | H | 4-F | CH₂CH₂ |
| 4-Cl | 5-Cl | H | 4-F | CH₂CH₂ |
| 4-Br | 5-Cl | H | 4-F | CH₂CH₂ |
| 4-F | 5-Cl | H | 4-F | CH₂CH₂ |

TABLE 11-continued

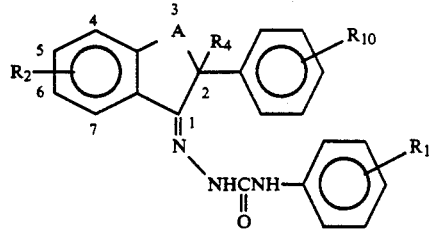

| R₁ | R₂ | R₄ | R₁₀ | A |
|---|---|---|---|---|
| 4-OCF₃ | 5-Cl | H | 4-F | CH₂CH₂ |
| 4-OCF₂H | 5-Cl | H | 4-F | CH₂CH₂ |
| 4-NO₂ | 5-Cl | H | 4-F | CH₂CH₂ |
| 3,4-di-Cl | 5-Cl | H | 4-F | CH₂CH₂ |
| 3,4-CH₂C(Me)₂O | 5-Cl | H | 4-F | CH₂CH₂ |
| 3,4-CF₂CF₂O | 5-Cl | H | 4-F | CH₂CH₂ |
| 4-CF₃ | 5-Cl | H | 4-Cl | CH₂CH₂ |
| 4-Cl | 5-Cl | H | 4-Cl | CH₂CH₂ |
| 4-Br | 5-Cl | H | 4-Cl | CH₂CH₂ |
| 4-OCF₃ | 5-Cl | H | 4-Cl | CH₂CH₂ |
| 4-OCF₂H | 5-Cl | H | 4-Cl | CH₂CH₂ |
| 3,4-CF₂CF₂O | 5-Cl | H | 4-Cl | CH₂CH₂ |
| 3,4-CH₂C(Me)₂O | 5-Cl | H | 4-Cl | CH₂CH₂ |
| 4-CN | 5-Cl | H | 4-Cl | CH₂CH₂ |
| 4-F | 5-Cl | H | 4-Cl | CH₂CH₂ |
| 4-NO₂ | 5-Cl | H | 4-Cl | CH₂CH₂ |
| H | 5-Cl | H | 4-Cl | CH₂CH₂ |
| 4-CF₃ | 5-CF₃ | H | 4-F | CH₂CH₂ |
| 4-OCF₃ | 5-CF₃ | H | 4-F | CH₂CH₂ |
| 4-Cl | 5-CF₃ | H | 4-F | CH₂CH₂ |
| 4-Br | 5-CF₃ | H | 4-F | CH₂CH₂ |
| 4-CF₃ | 5-OCF₂H | H | 4-F | CH₂CH₂ |
| 4-Cl | 5-OCF₂H | H | 4-F | CH₂CH₂ |
| 4-Br | 5-OCF₂H | H | 4-F | CH₂CH₂ |
| 4-CF₃ | 5-OCF₂H | H | 4-Cl | CH₂CH₂ |
| 4-Cl | 5-OCF₂H | H | 4-Cl | CH₂CH₂ |
| 4-Br | 5-OCF₂H | H | 4-Cl | CH₂CH₂ |
| 4-CF₃ | 4-F | H | 4-F | CH₂CH₂ |
| 4-Cl | 4-F | H | 4-F | CH₂CH₂ |
| 4-Br | 4-F | H | 4-F | CH₂CH₂ |
| 4-CF₃ | 4-F | H | 4-Cl | CH₂CH₂ |
| 4-Cl | 4-F | H | 4-Cl | CH₂CH₂ |
| 4-Br | 4-F | H | 4-Cl | CH₂CH₂ |
| 4-CF₃ | 4-Cl | H | 4-Cl | CH₂CH₂ |
| 4-Cl | 4-Cl | H | 4-Cl | CH₂CH₂ |
| 4-Br | 4-Cl | H | 4-Cl | CH₂CH₂ |
| 4-CF₃ | 4-Cl | H | 4-F | CH₂CH₂ |
| 4-Cl | 4-Cl | H | 4-F | CH₂CH₂ |
| 4-Br | 4-Cl | H | 4-F | CH₂CH₂ |
| 4-CF₃ | 5-Cl | H | 4-CF₃ | CH₂CH₂ |
| 4-Cl | 5-Cl | H | 4-CF₃ | CH₂CH₂ |
| 4-Br | 5-Cl | H | 4-CF₃ | CH₂CH₂ |
| 4-OCF₂H | 5-Cl | H | 4-CF₃ | CH₂CH₂ |
| 4-CF₃ | 5-Cl | H | 4-Me | CH₂CH₂ |
| 4-Cl | 5-Cl | H | 4-Me | CH₂CH₂ |
| 4-Br | 5-Cl | H | 4-Me | CH₂CH₂ |
| 4-OCF₂H | 5-Cl | H | 4-Me | CH₂CH₂ |
| 4-CF₃ | 5-Cl | H | 4-SMe | CH₂CH₂ |
| 4-Cl | 5-Cl | H | 4-SMe | CH₂CH₂ |
| 4-Br | 5-Cl | H | 4-SMe | CH₂CH₂ |
| 4-OCF₃ | 5-Cl | H | 4-SMe | CH₂CH₂ |
| 4-CF₃ | 5-Cl | H | 4-NO₂ | CH₂CH₂ |
| 4-Cl | 5-Cl | H | 4-NO₂ | CH₂CH₂ |
| 4-Br | 5-Cl | H | 4-NO₂ | CH₂CH₂ |
| 4-OCF₂H | 5-Cl | H | 4-NO₂ | CH₂CH₂ |
| 4-CF₃ | 5-Cl | H | 4-OPh | CH₂CH₂ |
| 4-Cl | 5-Cl | H | 4-OPh | CH₂CH₂ |
| 4-Br | 5-Cl | H | 4-OPh | CH₂CH₂ |
| 4-OCF₂H | 5-Cl | H | 4-OPh | CH₂CH₂ |
| 4-CF₃ | H | Me | H | CH₂CH₂ |
| 4-Cl | H | Me | H | CH₂CH₂ |
| 4-Br | H | Me | H | CH₂CH₂ |
| 4-OCF₂H | H | Me | H | CH₂CH₂ |
| 4-OCF₃ | H | Me | H | CH₂CH₂ |
| 4-CF₃ | 4-F | Me | H | CH₂CH₂ |
| 4-Cl | 4-F | Me | H | CH₂CH₂ |
| 4-Br | 4-F | Me | H | CH₂CH₂ |
| 4-OCF₂H | 4-F | Me | H | CH₂CH₂ |
| 4-OCF₃ | 4-F | Me | H | CH₂CH₂ |

TABLE 11-continued

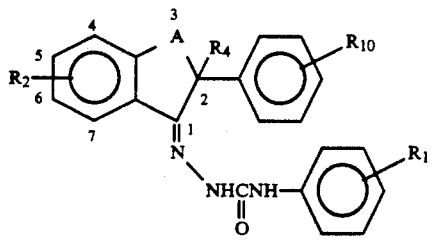

| R₁ | R₂ | R₄ | R₁₀ | A |
|---|---|---|---|---|
| 4-CF₃ | 4-Cl | Me | H | CH₂CH₂ |
| 4-Cl | 4-Cl | Me | H | CH₂CH₂ |
| 4-Br | 4-Cl | Me | H | CH₂CH₂ |
| 4-OCF₂H | 4-Cl | Me | H | CH₂CH₂ |
| 4-OCF₃ | 4-Cl | Me | H | CH₂CH₂ |
| 4-CF₃ | 5-F | Me | H | CH₂CH₂ |
| 4-Cl | 5-F | Me | H | CH₂CH₂ |
| 4-Br | 5-F | Me | H | CH₂CH₂ |
| 4-OCF₂H | 5-F | Me | H | CH₂CH₂ |
| 4-CF₃ | 5-Cl | Me | H | CH₂CH₂ |
| 4-Cl | 5-Cl | Me | H | CH₂CH₂ |
| 4-Br | 5-Cl | Me | H | CH₂CH₂ |
| 4-OCF₂H | 5-Cl | Me | H | CH₂CH₂ |
| 4-CF₃ | 4-F | Me | 4-F | CH₂CH₂ |
| 4-Cl | 4-F | Me | 4-F | CH₂CH₂ |
| 4-Br | 4-F | Me | 4-F | CH₂CH₂ |
| 4-OCF₂H | 4-F | Me | 4-F | CH₂CH₂ |
| 4-CF₃ | 4-Cl | Me | 4-F | CH₂CH₂ |
| 4-Cl | 4-Cl | Me | 4-F | CH₂CH₂ |
| 4-Br | 4-Cl | Me | 4-F | CH₂CH₂ |
| 4-OCF₂H | 4-Cl | Me | 4-F | CH₂CH₂ |
| 4-CF₃ | 5-F | Me | 4-F | CH₂CH₂ |
| 4-Cl | 5-F | Me | 4-F | CH₂CH₂ |
| 4-Br | 5-F | Me | 4-F | CH₂CH₂ |
| 4-OCF₂H | 5-F | Me | 4-F | CH₂CH₂ |
| 4-CF₃ | 5-Cl | Me | 4-F | CH₂CH₂ |
| 4-Cl | 5-Cl | Me | 4-F | CH₂CH₂ |
| 4-Br | 5-Cl | Me | 4-F | CH₂CH₂ |
| 4-OCF₂H | 5-Cl | Me | 4-F | CH₂CH₂ |
| 4-CF₃ | 4-F | Me | 4-Cl | CH₂CH₂ |
| 4-Cl | 4-F | Me | 4-Cl | CH₂CH₂ |
| 4-Br | 4-F | Me | 4-Cl | CH₂CH₂ |
| 4-OCF₂H | 4-F | Me | 4-Cl | CH₂CH₂ |
| 4-CF₃ | 4-Cl | Me | 4-Cl | CH₂CH₂ |
| 4-Cl | 4-Cl | Me | 4-Cl | CH₂CH₂ |
| 4-Br | 4-Cl | Me | 4-Cl | CH₂CH₂ |
| 4-OCF₂H | 4-Cl | Me | 4-Cl | CH₂CH₂ |
| 4-CF₃ | 5-F | Me | 4-Cl | CH₂CH₂ |
| 4-Cl | 5-F | Me | 4-Cl | CH₂CH₂ |
| 4-Br | 5-F | Me | 4-Cl | CH₂CH₂ |
| 4-OCF₂H | 5-F | Me | 4-Cl | CH₂CH₂ |
| 4-CF₃ | 5-Cl | Me | 4-Cl | CH₂CH₂ |
| 4-Cl | 5-Cl | Me | 4-Cl | CH₂CH₂ |
| 4-Br | 5-Cl | Me | 4-Cl | CH₂CH₂ |
| 4-OCF₂H | 5-Cl | Me | 4-Cl | CH₂CH₂ |
| 4-CF₃ | 5-Cl | Et | 4-F | CH₂CH₂ |
| 4-Cl | 5-Cl | Et | 4-F | CH₂CH₂ |
| 4-Br | 5-Cl | Et | 4-F | CH₂CH₂ |
| 4-CF₃ | 5-Cl | Et | 4-Cl | CH₂CH₂ |
| 4-Cl | 5-Cl | Et | 4-Cl | CH₂CH₂ |
| 4-Br | 5-Cl | Et | 4-Cl | CH₂CH₂ |
| 4-CF₃ | 5-Cl | allyl | 4-F | CH₂CH₂ |
| 4-Cl | 5-Cl | allyl | 4-F | CH₂CH₂ |
| 4-Br | 5-Cl | allyl | 4-F | CH₂CH₂ |
| 4-CF₃ | 5-Cl | allyl | 4-Cl | CH₂CH₂ |
| 4-Cl | 5-Cl | allyl | 4-Cl | CH₂CH₂ |
| 4-Br | 5-Cl | allyl | 4-Cl | CH₂CH₂ |
| 4-CF₃ | 5-Cl | propargyl | 4-F | CH₂CH₂ |
| 4-Cl | 5-Cl | propargyl | 4-F | CH₂CH₂ |
| 4-Br | 5-Cl | propargyl | 4-F | CH₂CH₂ |
| 4-CF₃ | 5-Cl | propargyl | 4-Cl | CH₂CH₂ |
| 4-Cl | 5-Cl | propargyl | 4-Cl | CH₂CH₂ |
| 4-Br | 5-Cl | propargyl | 4-Cl | CH₂CH₂ |
| 4-CF₃ | 5-F | H | 4-F | NMe |
| 4-OCF₃ | 5-F | H | 4-F | NMe |

TABLE 11-continued

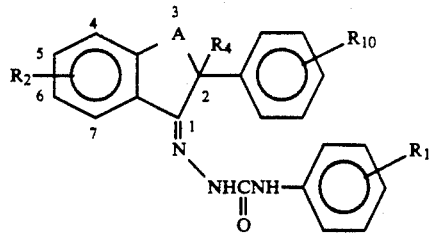

| R₁ | R₂ | R₄ | R₁₀ | A |
|---|---|---|---|---|
| 4-CF₃ | 5-Cl | H | 4-F | NMe |
| 4-OCF₃ | 5-Cl | H | 4-F | NMe |
| 4-CF₃ | 4-F | Me | 4-Cl | NMe |
| 4-Cl | 4-F | Me | 4-Cl | NMe |
| 4-Br | 4-F | Me | 4-Cl | NMe |
| 4-OCF₂H | 4-F | Me | 4-Cl | NMe |
| 4-CF₃ | 4-Cl | Me | 4-Cl | NMe |
| 4-Cl | 4-Cl | Me | 4-Cl | NMe |
| 4-Br | 4-Cl | Me | 4-Cl | NMe |
| 4-OCF₂H | 4-Cl | Me | 4-Cl | NMe |
| 4-CF₃ | 5-F | Me | 4-Cl | NMe |
| 4-Cl | 5-F | Me | 4-Cl | NMe |
| 4-Br | 5-F | Me | 4-Cl | NMe |
| 4-OCF₂H | 5-F | Me | 4-Cl | NMe |
| 4-CF₃ | 5-Cl | Me | 4-Cl | NMe |
| 4-Cl | 5-Cl | Me | 4-Cl | NMe |
| 4-Br | 5-Cl | Me | 4-Cl | NMe |
| 4-OCF₂H | 5-Cl | Me | 4-Cl | NMe |
| 4-F | 5-F | H | H | CHMe |
| 4-Cl | 5-F | H | H | CHMe |
| 4-Br | 5-F | H | H | CHMe |
| 4-CF₃ | 5-F | H | H | CHMe |
| 4-OCF₂H | 5-F | H | H | CHMe |
| 4-OCF₃ | 5-F | H | H | CHMe |
| 4-NO₂ | 5-F | H | H | CHMe |
| 4-SCF₂H | 5-F | H | H | CHMe |
| 4-CN | 5-F | H | H | CHMe |
| 3,4-CF₂CF₂O | 5-F | H | H | CHMe |
| 3,4-CH₂C(Me)₂O | 5-F | H | H | CHMe |
| 4-F | 5-Cl | H | H | CHMe |
| 4-Cl | 5-Cl | H | H | CHMe |
| 4-Br | 5-Cl | H | H | CHMe |
| 4-CF₃ | 5-Cl | H | H | CHMe |
| 4-OCF₂H | 5-Cl | H | H | CHMe |
| 4-OCF₃ | 5-Cl | H | H | CHMe |
| 4-NO₂ | 5-Cl | H | H | CHMe |
| 4-CF₃ | 4-Cl | H | 4-Cl | CHMe |
| 4-Cl | 4-Cl | H | 4-Cl | CHMe |
| 4-Br | 4-Cl | H | 4-Cl | CHMe |
| 4-CF₃ | 4-Cl | H | 4-F | CHMe |
| 4-Cl | 4-Cl | H | 4-F | CHMe |
| 4-Br | 4-Cl | H | 4-F | CHMe |
| 4-CF₃ | 5-Cl | H | 4-CF₃ | CHMe |
| 4-Cl | 5-Cl | H | 4-CF₃ | CHMe |
| 4-Br | 5-Cl | H | 4-CF₃ | CHMe |
| 4-OCF₂H | 5-Cl | H | 4-CF₃ | CHMe |
| 4-CF₃ | 5-Cl | H | 4-Me | CHMe |
| 4-Cl | 5-Cl | H | 4-Me | CHMe |
| 4-Br | 5-Cl | H | 4-Me | CHMe |
| 4-OCF₂H | 5-Cl | H | 4-Me | CHMe |
| 4-CF₃ | 5-Cl | H | 4-SMe | CHMe |
| 4-Cl | 5-Cl | H | 4-SMe | CHMe |
| 4-Br | 5-Cl | H | 4-SMe | CHMe |
| 4-OCF₂H | 5-Cl | H | 4-SMe | CHMe |
| 4-CF₃ | 4-F | Me | 4-Cl | CHMe |
| 4-Cl | 4-F | Me | 4-Cl | CHMe |
| 4-Br | 4-F | Me | 4-Cl | CHMe |
| 4-OCF₂H | 4-F | Me | 4-Cl | CHMe |
| 4-CF₃ | 4-Cl | Me | 4-Cl | CHMe |
| 4-Cl | 4-Cl | Me | 4-Cl | CHMe |
| 4-Br | 4-Cl | Me | 4-Cl | CHMe |
| 4-OCF₂H | 4-Cl | Me | 4-Cl | CHMe |
| 4-CF₃ | 5-F | Me | 4-Cl | CHMe |
| 4-Cl | 5-F | Me | 4-Cl | CHMe |
| 4-Br | 5-F | Me | 4-Cl | CHMe |

TABLE 11-continued

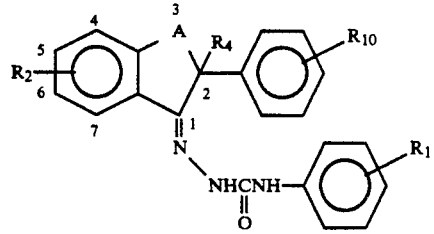

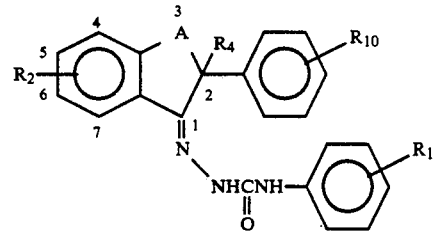

| R1 | R2 | R4 | R10 | A |
|---|---|---|---|---|
| 4-OCF2H | 5-F | Me | 4-Cl | CHMe |
| 4-CF3 | 5-Cl | Me | 4-Cl | CHMe |
| 4-Cl | 5-Cl | Me | 4-Cl | CHMe |
| 4-Br | 5-Cl | Me | 4-Cl | CHMe |
| 4-OCF2H | 5-Cl | Me | 4-Cl | CHMe |
| 4-CF3 | 5-Cl | Me | 4-Cl | CHMe |
| 4-Cl | 5-Cl | Me | 4-Cl | CHMe |
| 4-Br | 5-Cl | Me | 4-Cl | CHMe |
| 4-OCF2H | 5-Cl | Me | 4-Cl | CHMe |
| 4-CF3 | 4-F | Me | 4-Cl | SO2 |
| 4-Cl | 4-F | Me | 4-Cl | SO2 |
| 4-Br | 4-F | Me | 4-Cl | SO2 |
| 4-OCF2H | 4-F | Me | 4-Cl | SO2 |
| 4-CF3 | 4-Cl | Me | 4-Cl | SO2 |
| 4-Cl | 4-Cl | Me | 4-Cl | SO2 |
| 4-Br | 4-Cl | Me | 4-Cl | SO2 |
| 4-OCF2H | 4-Cl | Me | 4-Cl | SO2 |
| 4-CF3 | 5-F | Me | 4-Cl | SO2 |
| 4-Cl | 5-F | Me | 4-Cl | SO2 |
| 4-Br | 5-F | Me | 4-Cl | SO2 |
| 4-OCF2H | 5-F | Me | 4-Cl | SO2 |
| 4-CF3 | 5-Cl | Me | 4-Cl | SO2 |
| 4-Cl | 5-Cl | Me | 4-Cl | SO2 |
| 4-Br | 5-Cl | Me | 4-Cl | SO2 |
| 4-OCF2H | 5-Cl | Me | 4-Cl | SO2 |
| 4-CF3 | 5-Cl | Me | 4-Cl | SO2 |
| 4-Cl | 5-Cl | Me | 4-Cl | SO2 |
| 4-Br | 5-Cl | Me | 4-Cl | SO2 |
| 4-OCF2H | 5-Cl | Me | 4-Cl | SO2 |
| 4-F | 5-F | H | H | C(Me)2 |
| 4-Cl | 5-F | H | H | C(Me)2 |
| 4-Br | 5-F | H | H | C(Me)2 |
| 4-CF3 | 5-F | H | H | C(Me)2 |
| 4-OCF2H | 5-F | H | H | C(Me)2 |
| 4-OCF3 | 5-F | H | H | C(Me)2 |
| 4-NO2 | 5-F | H | H | C(Me)2 |
| 4-SCF2H | 5-F | H | H | C(Me)2 |
| 4-CN | 5-F | H | H | C(Me)2 |
| 3,4-CF2CF2O | 5-F | H | H | C(Me)2 |
| 3,4-CH2C(Me)2O | 5-F | H | H | C(Me)2 |
| 4-F | 5-Cl | H | H | C(Me)2 |
| 4-Cl | 5-Cl | H | H | C(Me)2 |
| 4-Br | 5-Cl | H | H | C(Me)2 |
| 4-CF3 | 5-Cl | H | H | C(Me)2 |
| 4-OCF2H | 5-Cl | H | H | C(Me)2 |
| 4-OCF3 | 5-Cl | H | H | C(Me)2 |
| 4-NO2 | 5-Cl | H | H | C(Me)2 |
| 4-CF3 | 4-Cl | H | 4-Cl | C(Me)2 |
| 4-Cl | 4-Cl | H | 4-Cl | C(Me)2 |
| 4-Br | 4-Cl | H | 4-Cl | C(Me)2 |
| 4-CF3 | 4-Cl | H | 4-F | C(Me)2 |
| 4-Cl | 4-Cl | H | 4-F | C(Me)2 |
| 4-Br | 4-Cl | H | 4-F | C(Me)2 |
| 4-OCF3 | 4-Cl | H | 4-F | C(Me)2 |
| 4-CF3 | 5-Cl | H | 4-CF3 | C(Me)2 |
| 4-Cl | 5-Cl | H | 4-CF3 | C(Me)2 |
| 4-Br | 5-Cl | H | 4-CF3 | C(Me)2 |
| 4-OCF2H | 5-Cl | H | 4-CF3 | C(Me)2 |
| 4-OCF3 | 5-Cl | H | 4-CF3 | C(Me)2 |
| 4-CF3 | 5-Cl | H | 4-Me | C(Me)2 |
| 4-Cl | 5-Cl | H | 4-Me | C(Me)2 |
| 4-Br | 5-Cl | H | 4-Me | C(Me)2 |
| 4-OCF2H | 5-Cl | H | 4-Me | C(Me)2 |
| 4-CF3 | 5-F | Me | 4-F | C(Me)2 |
| 4-Cl | 5-F | Me | 4-F | C(Me)2 |
| 4-Br | 5-F | Me | 4-F | C(Me)2 |
| 4-OCF3 | 5-F | Me | 4-F | C(Me)2 |
| 4-OCF2H | 5-F | Me | 4-F | C(Me)2 |
| 4-CF3 | 5-Cl | H | 4-SMe | C(Me)2 |
| 4-Cl | 5-Cl | H | 4-SMe | C(Me)2 |
| 4-Br | 5-Cl | H | 4-SMe | C(Me)2 |
| 4-OCF2H | 5-Cl | H | 4-SMe | C(Me)2 |
| 4-CF3 | 4-F | Me | 4-Cl | C(Me)2 |
| 4-Cl | 4-F | Me | 4-Cl | C(Me)2 |
| 4-Br | 4-F | Me | 4-Cl | C(Me)2 |
| 4-OCF2H | 4-F | Me | 4-Cl | C(Me)2 |
| 4-CF3 | 4-Cl | Me | 4-Cl | C(Me)2 |
| 4-Cl | 4-Cl | Me | 4-Cl | C(Me)2 |
| 4-Br | 4-Cl | Me | 4-Cl | C(Me)2 |
| 4-OCF2H | 4-Cl | Me | 4-Cl | C(Me)2 |
| 4-CF3 | 5-F | Me | 4-Cl | C(Me)2 |
| 4-Cl | 5-F | Me | 4-Cl | C(Me)2 |
| 4-Br | 5-F | Me | 4-Cl | C(Me)2 |
| 4-OCF2H | 5-F | Me | 4-Cl | C(Me)2 |
| 4-CF3 | 5-Cl | Me | 4-Cl | C(Me)2 |
| 4-Cl | 5-Cl | Me | 4-Cl | C(Me)2 |
| 4-Br | 5-Cl | Me | 4-Cl | C(Me)2 |
| 4-OCF2H | 5-Cl | Me | 4-Cl | C(Me)2 |
| 4-CF3 | 5-Cl | Me | 4-Cl | C(Me)2 |
| 4-Cl | 5-Cl | Me | 4-Cl | C(Me)2 |
| 4-Br | 5-Cl | Me | 4-Cl | C(Me)2 |
| 4-OCF2H | 5-Cl | Me | 4-Cl | C(Me)2 |
| 4-CF3 | 5-F | Me | 4-F | C(Me)2 |
| 4-OCF3 | 5-F | Me | 4-F | C(Me)2 |
| 4-CF3 | 4-Cl | Me | 4-Cl | S(O) |
| 4-Cl | 4-Cl | Me | 4-Cl | S(O) |
| 4-Br | 4-Cl | Me | 4-Cl | S(O) |
| 4-OCF2H | 4-Cl | Me | 4-Cl | S(O) |
| 4-CF3 | 5-F | Me | 4-Cl | S(O) |
| 4-Cl | 5-F | Me | 4-Cl | S(O) |
| 4-Br | 5-F | Me | 4-Cl | S(O) |
| 4-OCF2H | 5-F | Me | 4-Cl | S(O) |
| 4-CF3 | 5-Cl | Me | 4-Cl | S(O) |
| 4-Cl | 5-Cl | Me | 4-Cl | S(O) |
| 4-Br | 5-Cl | Me | 4-Cl | S(O) |
| 4-OCF2H | 5-Cl | Me | 4-Cl | S(O) |
| 4-CF3 | 5-Cl | Me | 4-Cl | S(O) |
| 4-Cl | 5-Cl | Me | 4-Cl | S(O) |
| 4-Br | 5-Cl | Me | 4-Cl | S(O) |
| 4-OCF2H | 5-Cl | Me | 4-Cl | S(O) |
| 4-F | 5-F | H | H | OCH2 |
| 4-Cl | 5-F | H | H | OCH2 |
| 4-Br | 5-F | H | H | OCH2 |
| 4-CF3 | 5-F | H | H | OCH2 |
| 4-OCF2H | 5-F | H | H | OCH2 |
| 4-OCF3 | 5-F | H | H | OCH2 |
| 4-CF3 | 4-Cl | H | 4-Cl | OCH2 |
| 4-Cl | 4-Cl | H | 4-Cl | OCH2 |
| 4-Br | 4-Cl | H | 4-Cl | OCH2 |
| 4-CF3 | 4-Cl | H | 4-F | OCH2 |
| 4-Cl | 4-Cl | H | 4-F | OCH2 |
| 4-Br | 4-Cl | H | 4-F | OCH2 |
| 4-CF3 | 5-Cl | H | 4-CF3 | OCH2 |
| 4-Cl | 5-Cl | H | 4-CF3 | OCH2 |
| 4-Br | 5-Cl | H | 4-CF3 | OCH2 |
| 4-OCF2H | 5-Cl | H | 4-CF3 | OCH2 |
| 4-CF3 | 4-F | Me | 4-Cl | OCH2 |
| 4-Cl | 4-F | Me | 4-Cl | OCH2 |
| 4-Br | 4-F | Me | 4-Cl | OCH2 |
| 4-OCF2H | 4-F | Me | 4-Cl | OCH2 |
| 4-CF3 | 4-Cl | Me | 4-Cl | OCH2 |
| 4-Cl | 4-Cl | Me | 4-Cl | OCH2 |
| 4-Br | 4-Cl | Me | 4-Cl | OCH2 |
| 4-OCF2H | 4-Cl | Me | 4-Cl | OCH2 |
| 4-CF3 | 5-F | Me | 4-Cl | OCH2 |
| 4-Cl | 5-F | Me | 4-Cl | OCH2 |
| 4-Br | 5-F | Me | 4-Cl | OCH2 |
| 4-OCF2H | 5-F | Me | 4-Cl | OCH2 |

TABLE 11-continued

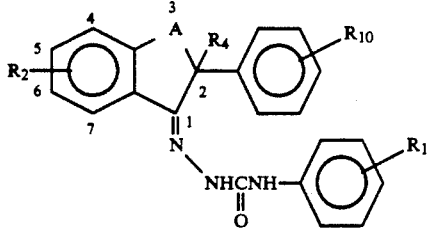

| R₁ | R₂ | R₄ | R₁₀ | A |
|---|---|---|---|---|
| 4-CF₃ | 5-Cl | Me | 4-Cl | OCH₂ |
| 4-Cl | 5-Cl | Me | 4-Cl | OCH₂ |
| 4-Br | 5-Cl | Me | 4-Cl | OCH₂ |
| 4-OCF₂H | 5-Cl | Me | 4-Cl | OCH₂ |
| 4-CF₃ | 5-Cl | Me | 4-Cl | OCH₂ |
| 4-Cl | 5-Cl | Me | 4-Cl | OCH₂ |
| 4-Br | 5-Cl | Me | 4-Cl | OCH₂ |
| 4-OCF₂H | 5-Cl | Me | 4-Cl | OCH₂ |
| 4-F | 5-F | H | H | CH₂O |
| 4-Cl | 5-F | H | H | CH₂O |
| 4-Br | 5-F | H | H | CH₂O |
| 4-CF₃ | 5-F | H | H | CH₂O |
| 4-OCF₂H | 5-F | H | H | CH₂O |
| 4-OCF₃ | 5-F | H | H | CH₂O |
| 4-NO₂ | 5-F | H | H | CH₂O |
| 4-SCF₂H | 5-F | H | H | CH₂O |
| 4-CN | 5-F | H | H | CH₂O |
| 3,4-CF₂CF₂O | 5-F | H | H | CH₂O |
| 3,4-CH₂C(Me)₂O | 5-F | H | H | CH₂O |
| 4-CF₃ | 4-Cl | H | 4-Cl | CH₂O |
| 4-Cl | 4-Cl | H | 4-Cl | CH₂O |
| 4-Br | 4-Cl | H | 4-Cl | CH₂O |
| 4-CF₃ | 4-Cl | H | 4-F | CH₂O |
| 4-Cl | 4-Cl | H | 4-F | CH₂O |
| 4-Br | 4-Cl | H | 4-F | CH₂O |
| 4-CF₃ | 5-Cl | H | 4-CF₃ | CH₂O |
| 4-Cl | 5-Cl | H | 4-CF₃ | CH₂O |
| 4-Br | 5-Cl | H | 4-CF₃ | CH₂O |
| 4-OCF₂H | 5-Cl | H | 4-CF₃ | CH₂O |
| 4-CF₃ | 4-F | Me | 4-Cl | CH₂O |
| 4-Cl | 4-F | Me | 4-Cl | CH₂O |
| 4-Br | 4-F | Me | 4-Cl | CH₂O |
| 4-OCF₂H | 4-F | Me | 4-Cl | CH₂O |
| 4-CF₃ | 4-Cl | Me | 4-Cl | CH₂O |
| 4-Cl | 4-Cl | Me | 4-Cl | CH₂O |
| 4-Br | 4-Cl | Me | 4-Cl | CH₂O |
| 4-OCF₂H | 4-Cl | Me | 4-Cl | CH₂O |
| 4-CF₃ | 5-F | Me | 4-Cl | CH₂O |
| 4-Cl | 5-F | Me | 4-Cl | CH₂O |
| 4-Br | 5-F | Me | 4-Cl | CH₂O |
| 4-OCF₂H | 5-F | Me | 4-Cl | CH₂O |
| 4-CF₃ | 5-Cl | Me | 4-Cl | CH₂O |
| 4-Cl | 5-Cl | Me | 4-Cl | CH₂O |
| 4-Br | 5-Cl | Me | 4-Cl | CH₂O |
| 4-OCF₂H | 5-Cl | Me | 4-Cl | CH₂O |
| 4-CF₃ | 5-Cl | Me | 4-Cl | CH₂O |
| 4-Cl | 5-Cl | Me | 4-Cl | CH₂O |
| 4-Br | 5-Cl | Me | 4-Cl | CH₂O |
| 4-OCF₂H | 5-Cl | Me | 4-Cl | CH₂O |
| 4-F | 5-F | H | H | SCH₂ |
| 4-Cl | 5-F | H | H | SCH₂ |
| 4-Br | 5-F | H | H | SCH₂ |
| 4-CF₃ | 5-F | H | H | SCH₂ |
| 4-OCF₂H | 5-F | H | H | SCH₂ |
| 4-OCF₃ | 5-F | H | H | SCH₂ |
| 4-Cl | 5-Cl | H | H | SCH₂ |
| 4-Br | 5-Cl | H | H | SCH₂ |
| 4-CF₃ | 5-Cl | H | H | SCH₂ |
| 4-OCF₂H | 5-Cl | H | H | SCH₂ |
| 4-OCF₃ | 5-Cl | H | H | SCH₂ |
| 4-CF₃ | 4-Cl | H | 4-Cl | SCH₂ |
| 4-Cl | 4-Cl | H | 4-Cl | SCH₂ |
| 4-Br | 4-Cl | H | 4-Cl | SCH₂ |
| 4-CF₃ | 4-Cl | H | 4-F | SCH₂ |
| 4-Cl | 4-Cl | H | 4-F | SCH₂ |
| 4-Br | 4-Cl | H | 4-F | SCH₂ |
| 4-CF₃ | 5-Cl | H | 4-CF₃ | SCH₂ |
| 4-Cl | 5-Cl | H | 4-CF₃ | SCH₂ |
| 4-Br | 5-Cl | H | 4-CF₃ | SCH₂ |

TABLE 11-continued

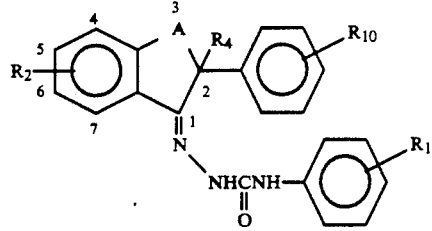

| R₁ | R₂ | R₄ | R₁₀ | A |
|---|---|---|---|---|
| 4-OCF₂H | 5-Cl | H | 4-CF₃ | SCH₂ |
| 4-CF₃ | 4-F | Me | 4-Cl | SCH₂ |
| 4-Cl | 4-F | Me | 4-Cl | SCH₂ |
| 4-Br | 4-F | Me | 4-Cl | SCH₂ |
| 4-OCF₂H | 4-F | Me | 4-Cl | SCH₂ |
| 4-CF₃ | 4-Cl | Me | 4-Cl | SCH₂ |
| 4-Cl | 4-Cl | Me | 4-Cl | SCH₂ |
| 4-Br | 4-Cl | Me | 4-Cl | SCH₂ |
| 4-OCF₂H | 4-Cl | Me | 4-Cl | SCH₂ |
| 4-CF₃ | 5-F | Me | 4-F | SCH₂ |
| 4-Cl | 5-F | Me | 4-F | SCH₂ |
| 4-Br | 5-F | Me | 4-F | SCH₂ |
| 4-OCF₂H | 5-F | Me | 4-F | SCH₂ |
| 4-CF₃ | 5-Cl | Me | 4-Cl | SCH₂ |
| 4-Cl | 5-Cl | Me | 4-Cl | SCH₂ |
| 4-Br | 5-Cl | Me | 4-Cl | SCH₂ |
| 4-OCF₂H | 5-Cl | Me | 4-Cl | SCH₂ |
| 4-CF₃ | 5-Cl | Me | 4-Cl | SCH₂ |
| 4-Cl | 5-Cl | Me | 4-Cl | SCH₂ |
| 4-Br | 5-Cl | Me | 4-Cl | SCH₂ |
| 4-OCF₂H | 5-Cl | Me | 4-Cl | SCH₂ |
| 4-F | 5-F | H | H | CH₂S |
| 4-Cl | 5-F | H | H | CH₂S |
| 4-Br | 5-F | H | H | CH₂S |
| 4-CF₃ | 5-F | H | H | CH₂S |
| 4-OCF₂H | 5-F | H | H | CH₂S |
| 4-OCF₃ | 5-F | H | H | CH₂S |
| 4-CF₃ | 4-F | H | 4-Cl | CH₂S |
| 4-Cl | 4-F | H | 4-Cl | CH₂S |
| 4-Br | 4-F | H | 4-Cl | CH₂S |
| 4-CF₃ | 5-F | H | 4-F | CH₂S |
| 4-Cl | 5-F | H | 4-F | CH₂S |
| 4-Br | 5-F | H | 4-F | CH₂S |

TABLE 12

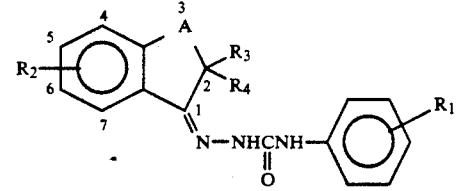

| R₁ | R₂ | R₃ | R₄ | A |
|---|---|---|---|---|
| 4-CF₃ | H | H | H | CH₂ |
| 4-Cl | H | H | H | CH₂ |
| 4-Br | H | H | H | CH₂ |
| 4-OCF₂H | H | H | H | CH₂ |
| 4-OCF₃ | H | H | H | CH₂ |
| 4-CF₃ | 4-F | H | H | CH₂ |
| 4-Cl | 4-F | H | H | CH₂ |
| 4-Br | 4-F | H | H | CH₂ |
| 4-OCF₂H | 4-F | H | H | CH₂ |
| 4-OCF₃ | 4-F | H | H | CH₂ |
| 4-CF₃ | 4-Cl | H | H | CH₂ |
| 4-Cl | 4-Cl | H | H | CH₂ |
| 4-Br | 4-Cl | H | H | CH₂ |
| 4-OCF₂H | 4-Cl | H | H | CH₂ |
| 4-OCF₃ | 4-Cl | H | H | CH₂ |
| 4-OCF₂H | 5-F | H | H | CH₂ |
| 4-OCF₃ | 5-F | H | H | CH₂ |
| 4-CF₃ | 4-F | Me | H | CH₂ |
| 4-Cl | 4-F | Me | H | CH₂ |
| 4-Br | 4-F | Me | H | CH₂ |

TABLE 12-continued

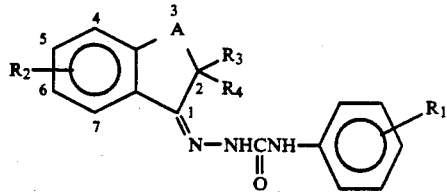

| R₁ | R₂ | R₃ | R₄ | A |
|---|---|---|---|---|
| 4-OCF₃ | 4-F | Me | H | CH₂ |
| 4-OCF₂H | 4-F | Me | H | CH₂ |
| 4-OCF₃ | 5-Cl | Me | H | CH₂ |
| 4-OCF₂H | 5-Cl | Me | H | CH₂ |
| 4-CF₃ | 5-CF₃ | Me | H | CH₂ |
| 4-OCF₃ | 5-CF₃ | Me | H | CH₂ |
| 4-Cl | 5-CF₃ | Me | H | CH₂ |
| 4-Br | 5-CF₃ | Me | H | CH₂ |
| 4-OCF₂H | 5-CF₃ | Me | H | CH₂ |
| 4-CF₃ | 5-OCF₂H | Me | H | CH₂ |
| 4-Cl | 5-OCF₂H | Me | H | CH₂ |
| 4-Br | 5-OCF₂H | Me | H | CH₂ |
| 4-OCF₃ | 5-OCF₂H | Me | H | CH₂ |
| 4-OCF₂H | 5-OCF₂H | Me | H | CH₂ |
| 4-OCF₃ | 5-F | Me | H | CH₂ |
| 4-CF₃ | 5-Cl | Et | H | CH₂ |
| 4-Cl | 5-Cl | Et | H | CH₂ |
| 4-Br | 5-Cl | Et | H | CH₂ |
| 4-OCF₃ | 5-Cl | Et | H | CH₂ |
| 4-CF₃ | 5-OCF₂H | Et | H | CH₂ |
| 4-Cl | 5-OCF₂H | Et | H | CH₂ |
| 4-Br | 5-OCF₂H | Et | H | CH₂ |
| 4-OCF₃ | 5-OCF₂H | Et | H | CH₂ |
| 4-CF₃ | 5-F | n-Bu | H | CH₂ |
| 4-Cl | 5-F | n-Bu | H | CH₂ |
| 4-Br | 5-F | n-Bu | H | CH₂ |
| 4-OCF₃ | 5-F | n-Bu | H | CH₂ |
| 4-CF₃ | 4-F | n-Bu | H | CH₂ |
| 4-Cl | 4-F | n-Bu | H | CH₂ |
| 4-Br | 4-F | n-Bu | H | CH₂ |
| 4-OCF₃ | 4-F | n-Bu | H | CH₂ |
| 4-CF₃ | 5-Cl | allyl | H | CH₂ |
| 4-Cl | 5-Cl | allyl | H | CH₂ |
| 4-Br | 5-Cl | allyl | H | CH₂ |
| 4-OCF₃ | 5-F | i-Pr | H | CH₂ |
| 4-CF₃ | 4-F | i-Pr | H | CH₂ |
| 4-OCF₃ | 4-F | i-Pr | H | CH₂ |
| 4-CF₃ | 4-CF₃ | i-Pr | H | CH₂ |
| 4-OCF₃ | 4-CF₃ | i-Pr | H | CH₂ |
| 4-CF₃ | 5-OCF₂H | i-Pr | H | CH₂ |
| 4-OCF₃ | 5-OCF₂H | i-Pr | H | CH₂ |
| 4-CF₃ | 5-CF₃ | i-Pr | H | CH₂ |
| 4-OCF₃ | 5-CF₃ | i-Pr | H | CH₂ |
| 4-CF₃ | 5-Cl | Me | Me | CH₂ |
| 4-Cl | 5-Cl | Me | Me | CH₂ |
| 4-Br | 5-Cl | Me | Me | CH₂ |
| 4-CF₃ | 5-F | Me | Me | CH₂ |
| 4-Cl | 5-F | Me | Me | CH₂ |
| 4-Br | 5-F | Me | Me | CH₂ |
| 4-CF₃ | 5-OCF₂H | Me | Me | CH₂ |
| 4-Cl | 5-OCF₂H | Me | Me | CH₂ |
| 4-Br | 5-OCF₂H | Me | Me | CH₂ |
| 4-CF₃ | 5-OCF₃ | Me | Me | CH₂ |
| 4-Cl | 5-OCF₃ | Me | Me | CH₂ |
| 4-Br | 5-OCF₃ | Me | Me | CH₂ |
| 4-CF₃ | 4-F | Me | Me | CH₂ |
| 4-Cl | 4-F | Me | Me | CH₂ |
| 4-Br | 4-F | Me | Me | CH₂ |
| 4-CF₃ | 5-Br | Me | Me | CH₂ |
| 4-Cl | 5-Br | Me | Me | CH₂ |
| 4-Br | 5-Br | Me | Me | CH₂ |
| 4-CF₃ | 5-Cl | CH₂Ph | H | CH₂ |
| 4-Cl | 5-Cl | CH₂Ph | H | CH₂ |
| 4-Br | 5-Cl | CH₂Ph | H | CH₂ |
| 4-OCF₃ | 5-Cl | CH₂Ph | H | CH₂ |
| 4-OCF₂H | 5-Cl | CH₂Ph | H | CH₂ |
| 4-CF₃ | 5-F | CH₂Ph-4-F | H | CH₂ |
| 4-Cl | 5-F | CH₂Ph-4-F | H | CH₂ |
| 4-Br | 5-F | CH₂Ph-4-F | H | CH₂ |
| 4-OCF₂H | 5-F | CH₂Ph-4-F | H | CH₂ |
| 4-OCF₃ | 5-F | CH₂Ph-4-F | H | CH₂ |

TABLE 12-continued

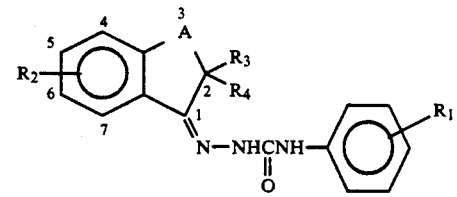

| R₁ | R₂ | R₃ | R₄ | A |
|---|---|---|---|---|
| 4-CF₃ | 5-OCF₂H | CH₂Ph-4-F | H | CH₂ |
| 4-Cl | 5-OCF₂H | CH₂Ph-4-F | H | CH₂ |
| 4-Br | 5-OCF₂H | CH₂Ph-4-F | H | CH₂ |
| 4-OCF₃ | 5-OCF₂H | CH₂Ph-4-F | H | CH₂ |
| 4-OCF₂H | 5-OCF₂H | CH₂Ph-4-F | H | CH₂ |
| 4-CF₃ | 5-Cl | CH₂Ph-4-Cl | H | CH₂ |
| 4-Cl | 5-Cl | CH₂Ph-4-Cl | H | CH₂ |
| 4-Br | 5-Cl | CH₂Ph-4-Cl | H | CH₂ |
| 4-OCF₂H | 5-Cl | CH₂Ph-4-Cl | H | CH₂ |
| 4-OCF₂H | 5-Cl | CH₂Ph-4-Cl | H | CH₂ |
| 4-CF₃ | 5-Cl | CO₂Me | H | CH₂ |
| 4-Cl | 5-Cl | CO₂Me | H | CH₂ |
| 4-Br | 5-Cl | CO₂Me | H | CH₂ |
| 4-OCF₂H | 5-Cl | CO₂Me | H | CH₂ |
| 4-OCF₃ | 5-Cl | CO₂Me | H | CH₂ |
| 4-CF₃ | 5-F | CO₂Me | H | CH₂ |
| 4-Cl | 5-F | CO₂Me | H | CH₂ |
| 4-Br | 5-F | CO₂Me | H | CH₂ |
| 4-OCF₂H | 5-F | CO₂Me | H | CH₂ |
| 4-OCF₃ | 5-F | CO₂Me | H | CH₂ |
| 4-CF₃ | 4-F | CO₂Me | H | CH₂ |
| 4-Cl | 4-F | CO₂Me | H | CH₂ |
| 4-Br | 4-F | CO₂Me | H | CH₂ |
| 4-CF₃ | 4-Cl | CO₂Me | H | CH₂ |
| 4-Cl | 4-Cl | CO₂Me | H | CH₂ |
| 4-Br | 4-Cl | CO₂Me | H | CH₂ |
| 4-CF₃ | 5-CF₃ | CO₂Me | H | CH₂ |
| 4-OCF₃ | 5-CF₃ | CO₂Me | H | CH₂ |
| 4-CF₃ | 5-OCF₃ | CO₂Me | H | CH₂ |
| 4-OCF₃ | 5-OCF₃ | CO₂Me | H | CH₂ |
| 4-CF₃ | H | CO₂Me | Me | CH₂ |
| 4-Cl | H | CO₂Me | Me | CH₂ |
| 4-Br | H | CO₂Me | Me | CH₂ |
| 4-OCF₂H | H | CO₂Me | Me | CH₂ |
| 4-OCF₃ | H | CO₂Me | Me | CH₂ |
| 3,4-CF₂CF₂O | H | CO₂Me | Me | CH₂ |
| 3,4-CH₂C(Me)₂O | H | CO₂Me | Me | CH₂ |
| 4-CF₃ | 5-Cl | CO₂Me | Me | CH₂ |
| 4-Cl | 5-Cl | CO₂Me | Me | CH₂ |
| 4-Br | 5-Cl | CO₂Me | Me | CH₂ |
| 4-OCF₂H | 5-Cl | CO₂Me | Me | CH₂ |
| 4-OCF₃ | 5-Cl | CO₂Me | Me | CH₂ |
| 3,4-CF₂CF₂O | 5-Cl | CO₂Me | Me | CH₂ |
| 3,4-CF₂C(Me)₂O | 5-Cl | CO₂Me | Me | CH₂ |
| 4-CF₃ | 5-F | CO₂Me | Me | CH₂ |
| 4-Cl | 5-F | CO₂Me | Me | CH₂ |
| 4-Br | 5-F | CO₂Me | Me | CH₂ |
| 4-OCF₂H | 5-F | CO₂Me | Me | CH₂ |
| 4-OCF₃ | 5-F | CO₂Me | Me | CH₂ |
| 3,4-CF₂CF₂O | 5-F | CO₂Me | Me | CH₂ |
| 3,4-CH₂C(Me)₂O | 5-F | CO₂Me | Me | CH₂ |
| 4-CF₃ | 4-F | CO₂Me | Me | CH₂ |
| 4-Cl | 4-F | CO₂Me | Me | CH₂ |
| 4-Br | 4-F | CO₂Me | Me | CH₂ |
| 4-OCF₃ | 4-F | CO₂Me | Me | CH₂ |
| 4-OCF₂H | 4-F | CO₂Me | Me | CH₂ |
| 3,4-CF₂CF₂O | 4-F | CO₂Me | Me | CH₂ |
| 3,4-CH₂C(Me)₂O | 4-F | CO₂Me | Me | CH₂ |
| 4-CF₃ | 5-Me | CO₂Me | Me | CH₂ |
| 4-Cl | 5-Me | CO₂Me | Me | CH₂ |
| 4-Br | 5-Me | CO₂Me | Me | CH₂ |
| 4-OCF₃ | 5-Me | CO₂Me | Me | CH₂ |
| 4-OCF₂H | 5-Me | CO₂Me | Me | CH₂ |
| 3,4-CF₂CF₂O | 5-Me | CO₂Me | Me | CH₂ |
| 3,4-CH₂C(Me)₂O | 5-Me | CO₂Me | Me | CH₂ |
| 4-CF₃ | 5-Br | CO₂Me | Me | CH₂ |
| 4-Cl | 5-Br | CO₂Me | Me | CH₂ |
| 4-Br | 5-Br | CO₂Me | Me | CH₂ |
| 4-OCF₃ | 5-Br | CO₂Me | Me | CH₂ |
| 4-OCF₂H | 5-Br | CO₂Me | Me | CH₂ |
| 3,4-CF₂CF₂O | 5-Br | CO₂Me | Me | CH₂ |

TABLE 12-continued

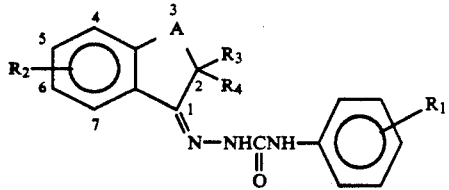

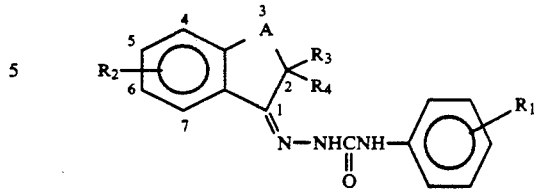

| R₁ | R₂ | R₃ | R₄ | A |
|---|---|---|---|---|
| 3,4-CH₂C(Me)₂O | 5-Br | CO₂Me | Me | CH₂ |
| 4-CF₃ | 5-OCF₂H | CO₂Me | Me | CH₂ |
| 4-Cl | 5-OCF₂H | CO₂Me | Me | CH₂ |
| 4-Br | 5-OCF₂H | CO₂Me | Me | CH₂ |
| 4-OCF₃ | 5-OCF₂H | CO₂Me | Me | CH₂ |
| 4-OCF₂H | 5-OCF₂H | CO₂Me | Me | CH₂ |
| 3,4-CF₂CF₂O | 5-OCF₂H | CO₂Me | Me | CH₂ |
| 3,4-CH₂C(Me)₂O | 5-OCF₂H | CO₂Me | Me | CH₂ |
| 4-CF₃ | 5-OCF₃ | CO₂Me | Me | CH₂ |
| 4-Cl | 5-OCF₃ | CO₂Me | Me | CH₂ |
| 4-Br | 5-OCF₃ | CO₂Me | Me | CH₂ |
| 4-OCF₂H | 5-OCF₃ | CO₂Me | Me | CH₂ |
| 4-OCF₃ | 5-OCF₃ | CO₂Me | Me | CH₂ |
| 3,4-CF₂CF₂O | 5-OCF₃ | CO₂Me | Me | CH₂ |
| 3,4-CH₂C(Me)₂O | 5-OCF₃ | CO₂Me | Me | CH₂ |
| 4-CF₃ | 5-CN | CO₂Me | Me | CH₂ |
| 4-Cl | 5-CN | CO₂Me | Me | CH₂ |
| 4-Br | 5-CN | CO₂Me | Me | CH₂ |
| 4-OCF₂H | 5-CN | CO₂Me | Me | CH₂ |
| 4-OCF₃ | 5-CN | CO₂Me | Me | CH₂ |
| 4-CF₃ | 5-CF₃ | CO₂Me | Me | CH₂ |
| 4-OCF₃ | 5-CF₃ | CO₂Me | Me | CH₂ |
| 4-CF₃ | 6-F | CO₂Me | Me | CH₂ |
| 4-Cl | 6-F | CO₂Me | Me | CH₂ |
| 4-Br | 6-F | CO₂Me | Me | CH₂ |
| 4-OCF₂H | 6-F | CO₂Me | Me | CH₂ |
| 4-OCF₃ | 6-F | CO₂Me | Me | CH₂ |
| 4-CF₃ | 5-Cl | CO₂Me | Et | CH₂ |
| 4-Cl | 5-Cl | CO₂Me | Et | CH₂ |
| 4-Br | 5-Cl | CO₂Me | Et | CH₂ |
| 4-CF₃ | 5-Cl | CO₂Me | CH₂Ph | CH₂ |
| 4-Cl | 5-Cl | CO₂Me | CH₂Ph | CH₂ |
| 4-Br | 5-Cl | CO₂Me | CH₂Ph | CH₂ |
| 4-CF₃ | 5-Cl | CO₂Me | allyl | CH₂ |
| 4-Cl | 5-Cl | CO₂Me | allyl | CH₂ |
| 4-Br | 5-Cl | CO₂Me | allyl | CH₂ |
| 4-CF₃ | 5-F | CO₂Et | Me | CH₂ |
| 4-Cl | 5-F | CO₂Et | Me | CH₂ |
| 4-Br | 5-F | CO₂Et | Me | CH₂ |
| 4-CF₃ | 5-F | CO₂CH₂CF₃ | Me | CH₂ |
| 4-Cl | 5-F | CO₂CH₂CF₃ | Me | CH₂ |
| 4-Br | 5-F | CO₂CH₂CF₃ | Me | CH₂ |
| 4-CF₃ | 5-F | CO₂Ph | Me | CH₂ |
| 4-Cl | 5-F | CO₂Ph | Me | CH₂ |
| 4-Br | 5-F | CO₂Ph | Me | CH₂ |
| 4-CF₃ | 5-Cl | CO₂H | H | CH₂ |
| 4-CF₃ | 5-Cl | CONHMe | H | CH₂ |
| 4-CF₃ | 5-Cl | CONMe | H | CH₂ |
| 4-CF₃ | 5-Cl | CONHPh | H | CH₂ |
| 4-CF₃ | 5-Cl | CSNMe₂ | H | CH₂ |
| 4-CF₃ | 5-Cl | propargyl | Me | CH₂ |
| 4-CF₃ | 5-Cl | CH₂CH₂CN | Me | CH₂ |
| 4-CF₃ | 5-Cl | CH₂CO₂Me | Me | CH₂ |
| 4-CF₃ | 5-Cl | CH₂OMe | Me | CH₂ |
| 4-CF₃ | 5-Cl | OMe | H | CH₂ |
| 4-CF₃ | 5-Cl | SMe | H | CH₂ |
| 4-CF₃ | 5-Cl | SO₂Me | H | CH₂ |
| 4-CF₃ | 5-Cl | C(O)Me | Me | CH₂ |
| 4-CF₃ | 5-Cl | C(O)Et | Me | CH₂ |
| 4-CF₃ | 5-Cl | C(O)Me | H | CH₂ |
| 4-CF₃ | 5-Cl | C(O)Et | H | CH₂ |
| 4-CF₃ | 5-Cl | CN | Me | CH₂ |
| 4-CF₃ | 5-Cl | CN | Et | CH₂ |
| 4-CF₃ | 5-Cl | CN | CH₂Ph | CH₂ |
| 4-CF₃ | 5-Cl | CN | H | CH₂ |
| 4-CF₃ | H | H | H | CH₂CH₂ |
| 4-Cl | H | H | H | CH₂CH₂ |
| 4-Br | H | H | H | CH₂CH₂ |
| 4-OCF₂H | H | H | H | CH₂CH₂ |
| 4-CF₃ | 4-F | H | H | CH₂CH₂ |
| 4-Cl | 4-F | H | H | CH₂CH₂ |
| 4-Br | 4-F | H | H | CH₂CH₂ |
| 4-OCF₂H | 4-F | H | H | CH₂CH₂ |
| 4-CF₃ | 4-Cl | H | H | CH₂CH₂ |
| 4-Cl | 4-Cl | H | H | CH₂CH₂ |
| 4-Br | 4-Cl | H | H | CH₂CH₂ |
| 4-OCF₂H | 4-Cl | H | H | CH₂CH₂ |
| 4-CF₃ | 5-F | H | H | CH₂CH₂ |
| 4-Cl | 5-F | H | H | CH₂CH₂ |
| 4-Br | 5-F | H | H | CH₂CH₂ |
| 4-OCF₂H | 5-F | H | H | CH₂CH₂ |
| 4-CF₃ | 6-F | H | H | CH₂CH₂ |
| 4-Cl | 6-F | H | H | CH₂CH₂ |
| 4-Br | 6-F | H | H | CH₂CH₂ |
| 4-OCF₂H | 6-F | H | H | CH₂CH₂ |
| 4-CF₃ | 6-Cl | H | H | CH₂CH₂ |
| 4-Cl | 6-Cl | H | H | CH₂CH₂ |
| 4-Br | 6-Cl | H | H | CH₂CH₂ |
| 4-OCF₂H | 6-Cl | H | H | CH₂CH₂ |
| 4-CF₃ | 4-F | Me | H | CH₂CH₂ |
| 4-Cl | 4-F | Me | H | CH₂CH₂ |
| 4-Br | 4-F | Me | H | CH₂CH₂ |
| 4-OCF₂H | 4-F | Me | H | CH₂CH₂ |
| 4-CF₃ | 5-Cl | Me | H | CH₂CH₂ |
| 4-Cl | 5-Cl | Me | H | CH₂CH₂ |
| 4-Br | 5-Cl | Me | H | CH₂CH₂ |
| 4-OCF₂H | 5-Cl | Me | H | CH₂CH₂ |
| 4-CF₃ | 5-OCF₂H | Me | H | CH₂CH₂ |
| 4-Cl | 5-OCF₂H | Me | H | CH₂CH₂ |
| 4-Br | 5-OCF₂H | Me | H | CH₂CH₂ |
| 4-OCF₂H | 5-OCF₂H | Me | H | CH₂CH₂ |
| 4-CF₃ | 5-F | Me | H | CH₂CH₂ |
| 4-Cl | 5-F | Me | H | CH₂CH₂ |
| 4-Br | 5-F | Me | H | CH₂CH₂ |
| 4-CF₃ | 5-Cl | Et | H | CH₂CH₂ |
| 4-Cl | 5-Cl | Et | H | CH₂CH₂ |
| 4-Br | 5-Cl | Et | H | CH₂CH₂ |
| 4-CF₃ | 5-OCF₂H | Et | H | CH₂CH₂ |
| 4-Cl | 5-OCF₂H | Et | H | CH₂CH₂ |
| 4-Br | 5-OCF₂H | Et | H | CH₂CH₂ |
| 4-CF₃ | 5-F | n-Bu | H | CH₂CH₂ |
| 4-Cl | 5-F | n-Bu | H | CH₂CH₂ |
| 4-Br | 5-F | n-Bu | H | CH₂CH₂ |
| 4-CF₃ | 4-F | n-Bu | H | CH₂CH₂ |
| 4-Cl | 4-F | n-Bu | H | CH₂CH₂ |
| 4-Br | 4-F | n-Bu | H | CH₂CH₂ |
| 4-CF₃ | 5-Cl | allyl | H | CH₂CH₂ |
| 4-Cl | 5-Cl | allyl | H | CH₂CH₂ |
| 4-Br | 5-Cl | allyl | H | CH₂CH₂ |
| 4-CF₃ | 5-Cl | Me | Me | CH₂CH₂ |
| 4-Cl | 5-Cl | Me | Me | CH₂CH₂ |
| 4-Br | 5-Cl | Me | Me | CH₂CH₂ |
| 4-CF₃ | 5-F | Me | Me | CH₂CH₂ |
| 4-Cl | 5-F | Me | Me | CH₂CH₂ |
| 4-Br | 5-F | Me | Me | CH₂CH₂ |
| 4-CF₃ | 5-OCF₂H | Me | Me | CH₂CH₂ |
| 4-Cl | 5-OCF₂H | Me | Me | CH₂CH₂ |
| 4-Br | 5-OCF₂H | Me | Me | CH₂CH₂ |
| 4-CF₃ | 5-OCF₃ | Me | Me | CH₂CH₂ |
| 4-Cl | 5-OCF₃ | Me | Me | CH₂CH₂ |
| 4-Br | 5-OCF₃ | Me | Me | CH₂CH₂ |
| 4-CF₃ | 4-F | Me | Me | CH₂CH₂ |
| 4-Cl | 4-F | Me | Me | CH₂CH₂ |
| 4-Br | 4-F | Me | Me | CH₂CH₂ |
| 4-CF₃ | 5-Br | Me | Me | CH₂CH₂ |
| 4-Cl | 5-Br | Me | Me | CH₂CH₂ |
| 4-Br | 5-Br | Me | Me | CH₂CH₂ |
| 4-CF₃ | 5-Cl | CH₂Ph | H | CH₂CH₂ |
| 4-Cl | 5-Cl | CH₂Ph | H | CH₂CH₂ |
| 4-Br | 5-Cl | CH₂Ph | H | CH₂CH₂ |
| 4-OCF₃ | 5-Cl | CH₂Ph | H | CH₂CH₂ |
| 4-OCF₂H | 5-Cl | CH₂Ph | H | CH₂CH₂ |

TABLE 12-continued

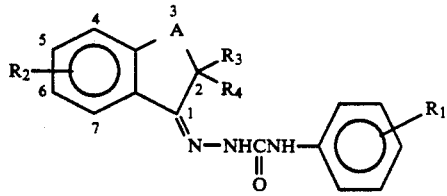 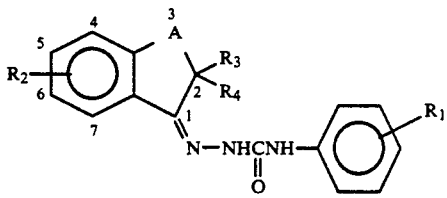

| R₁ | R₂ | R₃ | R₄ | A |
|---|---|---|---|---|
| 4-CF₃ | 5-F | CH₂Ph-4-F | H | CH₂CH₂ |
| 4-Cl | 5-F | CH₂Ph-4-F | H | CH₂CH₂ |
| 4-Br | 5-F | CH₂Ph-4-F | H | CH₂CH₂ |
| 4-OCF₂H | 5-F | CH₂Ph-4-F | H | CH₂CH₂ |
| 4-OCF₃ | 5-F | CH₂Ph-4-F | H | CH₂CH₂ |
| 4-CF₃ | 5-OCF₂H | CH₂Ph-4-F | H | CH₂CH₂ |
| 4-Cl | 5-OCF₂H | CH₂Ph-4-F | H | CH₂CH₂ |
| 4-Br | 5-OCF₂H | CH₂Ph-4-F | H | CH₂CH₂ |
| 4-OCF₃ | 5-OCF₂H | CH₂Ph-4-F | H | CH₂CH₂ |
| 4-OCF₂H | 5-OCF₂H | CH₂Ph-4-F | H | CH₂CH₂ |
| 4-CF₃ | 5-Cl | CH₂Ph-4-Cl | H | CH₂CH₂ |
| 4-Cl | 5-Cl | CH₂Ph-4-Cl | H | CH₂CH₂ |
| 4-Br | 5-Cl | CH₂Ph-4-Cl | H | CH₂CH₂ |
| 4-OCF₃ | 5-Cl | CH₂Ph-4-Cl | H | CH₂CH₂ |
| 4-OCF₂H | 5-Cl | CH₂Ph-4-Cl | H | CH₂CH₂ |
| 4-CF₃ | H | CO₂Me | H | CH₂CH₂ |
| 4-Cl | H | CO₂Me | H | CH₂CH₂ |
| 4-Br | H | CO₂Me | H | CH₂CH₂ |
| 4-OCF₂H | H | CO₂Me | H | CH₂CH₂ |
| 4-F | H | CO₂Me | H | CH₂CH₂ |
| 4-CF₃ | 5-Cl | CO₂Me | H | CH₂CH₂ |
| 4-Cl | 5-Cl | CO₂Me | H | CH₂CH₂ |
| 4-Br | 5-Cl | CO₂Me | H | CH₂CH₂ |
| 4-OCF₂H | 5-Cl | CO₂Me | H | CH₂CH₂ |
| 4-OCF₃ | 5-Cl | CO₂Me | H | CH₂CH₂ |
| 4-NO₂ | 5-Cl | CO₂Me | H | CH₂CH₂ |
| 4-CF₃ | 5-F | CO₂Me | H | CH₂CH₂ |
| 4-Cl | 5-F | CO₂Me | H | CH₂CH₂ |
| 4-Br | 5-F | CO₂Me | H | CH₂CH₂ |
| 4-OCF₂H | 5-F | CO₂Me | H | CH₂CH₂ |
| 4-OCF₃ | 5-F | CO₂Me | H | CH₂CH₂ |
| 4-CN | 5-F | CO₂Me | H | CH₂CH₂ |
| 4-CF₃ | 4-F | CO₂Me | H | CH₂CH₂ |
| 4-Cl | 4-F | CO₂Me | H | CH₂CH₂ |
| 4-Br | 4-F | CO₂Me | H | CH₂CH₂ |
| 4-CF₃ | 4-Cl | CO₂Me | H | CH₂CH₂ |
| 4-Cl | 4-Cl | CO₂Me | H | CH₂CH₂ |
| 4-Br | 4-Cl | CO₂Me | H | CH₂CH₂ |
| 4-CF₃ | 5-Cl | CO₂Me | Me | CH₂CH₂ |
| 4-Cl | 5-Cl | CO₂Me | Me | CH₂CH₂ |
| 4-Br | 5-Cl | CO₂Me | Me | CH₂CH₂ |
| 4-OCF₂H | 5-Cl | CO₂Me | Me | CH₂CH₂ |
| 4-OCF₃ | 5-Cl | CO₂Me | Me | CH₂CH₂ |
| 3,4-CF₂CF₂O | 5-Cl | CO₂Me | Me | CH₂CH₂ |
| 3,4-CF₂C(Me)₂O | 5-Cl | CO₂Me | Me | CH₂CH₂ |
| 4-CF₃ | 5-F | CO₂Me | Me | CH₂CH₂ |
| 4-Cl | 5-F | CO₂Me | Me | CH₂CH₂ |
| 4-Br | 5-F | CO₂Me | Me | CH₂CH₂ |
| 4-OCF₂H | 5-F | CO₂Me | Me | CH₂CH₂ |
| 4-OCF₃ | 5-F | CO₂Me | Me | CH₂CH₂ |
| 3,4-CF₂CF₂O | 5-F | CO₂Me | Me | CH₂CH₂ |
| 3,4-CH₂C(Me)₂O | 5-F | CO₂Me | Me | CH₂CH₂ |
| 4-CF₃ | H | H | H | O |
| 4-Cl | H | H | H | O |
| 4-Br | H | H | H | O |
| 4-OCF₃ | H | H | H | O |
| 4-OCF₂H | H | H | H | O |
| 4-CF₃ | 4-F | H | H | O |
| 4-Cl | 4-F | H | H | O |
| 4-Br | 4-F | H | H | O |
| 4-OCF₃ | 4-F | H | H | O |
| 4-OCF₂H | 4-F | H | H | O |
| 4-CF₃ | 4-Cl | H | H | O |
| 4-Cl | 4-Cl | H | H | O |
| 4-Br | 4-Cl | H | H | O |
| 4-OCF₃ | 4-Cl | H | H | O |
| 4-OCF₂H | 4-Cl | H | H | O |
| 4-CF₃ | 5-F | H | H | O |
| 4-Cl | 5-F | H | H | O |
| 4-Br | 5-F | H | H | O |
| 4-OCF₃ | 5-F | H | H | O |
| 4-OCF₂H | 5-F | H | H | O |
| 4-CF₃ | 6-F | H | H | O |
| 4-CF₃ | 4-F | Me | H | O |
| 4-Cl | 4-F | Me | H | O |
| 4-Br | 4-F | Me | H | O |
| 4-OCF₃ | 4-F | Me | H | O |
| 4-OCF₂H | 4-F | Me | H | O |
| 4-CF₃ | 5-Cl | Me | H | O |
| 4-Cl | 5-Cl | Me | H | O |
| 4-Br | 5-Cl | Me | H | O |
| 4-OCF₃ | 5-Cl | Me | H | O |
| 4-OCF₂H | 5-Cl | Me | H | O |
| 4-CF₃ | 5-OCF₂H | Me | H | O |
| 4-Cl | 5-OCF₂H | Me | H | O |
| 4-Br | 5-OCF₂H | Me | H | O |
| 4-OCF₃ | 5-OCF₂H | Me | H | O |
| 4-OCF₂H | 5-OCF₂H | Me | H | O |
| 4-CF₃ | 5-CF₃ | Me | H | O |
| 4-Cl | 5-CF₃ | Me | H | O |
| 4-Br | 5-CF₃ | Me | H | O |
| 4-OCF₃ | 5-CF₃ | Me | H | O |
| 4-OCF₂H | 5-CF₃ | Me | H | O |
| 4-CF₃ | 5-F | Me | H | O |
| 4-Cl | 5-F | Me | H | O |
| 4-Br | 5-F | Me | H | O |
| 4-OCF₃ | 5-F | Me | H | O |
| 4-CF₃ | 5-Cl | Et | H | O |
| 4-Cl | 5-Cl | Et | H | O |
| 4-Br | 5-Cl | Et | H | O |
| 4-CF₃ | 5-OCF₂H | Et | H | O |
| 4-Cl | 5-OCF₂H | Et | H | O |
| 4-Br | 5-OCF₂H | Et | H | O |
| 4-CF₃ | 5-F | n-Bu | H | O |
| 4-Cl | 5-F | n-Bu | H | O |
| 4-Br | 5-F | n-Bu | H | O |
| 4-CF₃ | 4-F | n-Bu | H | O |
| 4-Cl | 4-F | n-Bu | H | O |
| 4-Br | 4-F | n-Bu | H | O |
| 4-CF₃ | 5-Cl | allyl | H | O |
| 4-Cl | 5-Cl | allyl | H | O |
| 4-Br | 5-Cl | allyl | H | O |
| 4-CF₃ | 5-Cl | Me | Me | O |
| 4-Cl | 5-Cl | Me | Me | O |
| 4-Br | 5-Cl | Me | Me | O |
| 4-CF₃ | 5-F | Me | Me | O |
| 4-Cl | 5-F | Me | Me | O |
| 4-Br | 5-F | Me | Me | O |
| 4-CF₃ | 5-OCF₂H | Me | Me | O |
| 4-Cl | 5-OCF₂H | Me | Me | O |
| 4-Br | 5-OCF₂H | Me | Me | O |
| 4-CF₃ | 5-OCF₃ | Me | Me | O |
| 4-Cl | 5-OCF₃ | Me | Me | O |
| 4-Br | 5-OCF₃ | Me | Me | O |
| 4-CF₃ | 4-F | Me | Me | O |
| 4-Cl | 4-F | Me | Me | O |
| 4-Br | 4-F | Me | Me | O |
| 4-CF₃ | 5-Br | Me | Me | O |
| 4-Cl | 5-Br | Me | Me | O |
| 4-Br | 5-Br | Me | Me | O |
| 4-OCF₃ | 5-Cl | allyl | Me | O |
| 4-CF₃ | 5-F | allyl | Me | O |
| 4-OCF₃ | 5-F | allyl | Me | O |
| 4-CF₃ | 5-F | Et | Me | O |
| 4-OCF₃ | 5-F | Et | Me | O |
| 4-CF₃ | 5-Cl | Et | Me | O |
| 4-OCF₃ | 5-Cl | Et | Me | O |
| 4-CF₃ | 5-CF₃ | Et | Me | O |
| 4-CF₃ | 5-CF₃ | allyl | Me | O |
| 4-OCF₃ | 5-CF₃ | allyl | Me | O |
| 4-CF₃ | 5-F | CH₂Ph | Me | O |
| 4-OCF₃ | 5-F | CH₂Ph | Me | O |

TABLE 12-continued

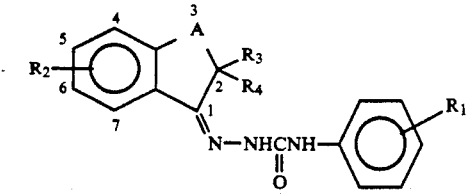

| R1 | R2 | R3 | R4 | A |
|---|---|---|---|---|
| 4-CF$_3$ | 5-Cl | CH$_2$Ph | Me | O |
| 4-OCF$_3$ | 5-Cl | CH$_2$Ph | Me | O |
| 4-CF$_3$ | 5-Cl | CH$_2$Ph | H | O |
| 4-Cl | 5-Cl | CH$_2$Ph | H | O |
| 4-Br | 5-Cl | CH$_2$Ph | H | O |
| 4-OCF$_3$ | 5-Cl | CH$_2$Ph | H | O |
| 4-OCF$_2$H | 5-Cl | CH$_2$Ph | H | O |
| 4-CF$_3$ | 5-F | CH$_2$Ph-4-F | H | O |
| 4-Cl | 5-F | CH$_2$Ph-4-F | H | O |
| 4-Br | 5-F | CH$_2$Ph-4-F | H | O |
| 4-OCF$_2$H | 5-F | CH$_2$Ph-4-F | H | O |
| 4-OCF$_3$ | 5-F | CH$_2$Ph-4-F | H | O |
| 4-CF$_3$ | 5-OCF$_2$H | CH$_2$Ph-4-F | H | O |
| 4-Cl | 5-OCF$_2$H | CH$_2$Ph-4-F | H | O |
| 4-Br | 5-OCF$_2$H | CH$_2$Ph-4-F | H | O |
| 4-OCF$_3$ | 5-OCF$_2$H | CH$_2$Ph-4-F | H | O |
| 4-OCF$_2$H | 5-OCF$_2$H | CH$_2$Ph-4-F | H | O |
| 4-CF$_3$ | 5-Cl | CH$_2$Ph-4-Cl | H | O |
| 4-Cl | 5-Cl | CH$_2$Ph-4-Cl | H | O |
| 4-Br | 5-Cl | CH$_2$Ph-4-Cl | H | O |
| 4-OCF$_3$ | 5-Cl | CH$_2$Ph-4-Cl | H | O |
| 4-OCF$_2$H | 5-Cl | CH$_2$Ph-4-Cl | H | O |
| 4-CF$_3$ | H | CO$_2$Me | H | O |
| 4-Cl | H | CO$_2$Me | H | O |
| 4-Br | H | CO$_2$Me | H | O |
| 4-OCF$_2$H | H | CO$_2$Me | H | O |
| 4-F | H | CO$_2$Me | H | O |
| 4-CF$_3$ | 5-Cl | CO$_2$Me | H | O |
| 4-Cl | 5-Cl | CO$_2$Me | H | O |
| 4-Br | 5-Cl | CO$_2$Me | H | O |
| 4-OCF$_2$H | 5-Cl | CO$_2$Me | H | O |
| 4-OCF$_3$ | 5-Cl | CO$_2$Me | H | O |
| 4-NO$_2$ | 5-Cl | CO$_2$Me | H | O |
| 4-CF$_3$ | 5-F | CO$_2$Me | H | O |
| 4-Cl | 5-F | CO$_2$Me | H | O |
| 4-Br | 5-F | CO$_2$Me | H | O |
| 4-OCF$_2$H | 5-F | CO$_2$Me | H | O |
| 4-OCF$_3$ | 5-F | CO$_2$Me | H | O |
| 4-CN | 5-F | CO$_2$Me | H | O |
| 4-CF$_3$ | 4-F | CO$_2$Me | H | O |
| 4-Cl | 4-F | CO$_2$Me | H | O |
| 4-Br | 4-F | CO$_2$Me | H | O |
| 4-CF$_3$ | 4-Cl | CO$_2$Me | H | O |
| 4-Cl | 4-Cl | CO$_2$Me | H | O |
| 4-Br | 4-Cl | CO$_2$Me | H | O |
| 4-CF$_3$ | H | CO$_2$Me | Me | O |
| 4-Cl | H | CO$_2$Me | Me | O |
| 4-Br | H | CO$_2$Me | Me | O |
| 4-OCF$_2$H | H | CO$_2$Me | Me | O |
| 4-OCF$_3$ | H | CO$_2$Me | Me | O |
| 4-CF$_3$ | 5-Cl | CO$_2$Me | Me | O |
| 4-Cl | 5-Cl | CO$_2$Me | Me | O |
| 4-Br | 5-Cl | CO$_2$Me | Me | O |
| 4-OCF$_2$H | 5-Cl | CO$_2$Me | Me | O |
| 4-OCF$_3$ | 5-Cl | CO$_2$Me | Me | O |
| 4-CF$_3$ | 5-F | CO$_2$Me | Me | O |
| 4-Cl | 5-F | CO$_2$Me | Me | O |
| 4-Br | 5-F | CO$_2$Me | Me | O |
| 4-OCF$_2$H | 5-F | CO$_2$Me | Me | O |
| 4-OCF$_3$ | 5-F | CO$_2$Me | Me | O |
| 4-CF$_3$ | 4-F | CO$_2$Me | Me | O |
| 4-Cl | 4-F | CO$_2$Me | Me | O |
| 4-Br | 4-F | CO$_2$Me | Me | O |
| 4-OCF$_3$ | 4-F | CO$_2$Me | Me | O |
| 4-OCF$_2$H | 4-F | CO$_2$Me | Me | O |
| 3,4-CF$_2$CF$_2$O | 4-F | CO$_2$Me | Me | O |
| 3,4-CH$_2$C(Me)$_2$O | 4-F | CO$_2$Me | Me | O |
| 4-CF$_3$ | 5-CF$_3$ | CO$_2$Me | Me | O |
| 4-Cl | 5-CF$_3$ | CO$_2$Me | Me | O |
| 4-Br | 5-CF$_3$ | CO$_2$Me | Me | O |
| 4-OCF$_3$ | 5-CF$_3$ | CO$_2$Me | Me | O |
| 4-OCF$_2$H | 5-CF$_3$ | CO$_2$Me | Me | O |
| 4-CF$_3$ | 5-Br | CO$_2$Me | Me | O |
| 4-Cl | 5-Br | CO$_2$Me | Me | O |
| 4-Br | 5-Br | CO$_2$Me | Me | O |
| 4-OCF$_3$ | 5-Br | CO$_2$Me | Me | O |
| 4-OCF$_2$H | 5-Br | CO$_2$Me | Me | O |
| 3,4-CF$_2$CF$_2$O | 5-Br | CO$_2$Me | Me | O |
| 3,4-CH$_2$C(Me)$_2$O | 5-Br | CO$_2$Me | Me | O |
| 4-CF$_3$ | 5-OCF$_2$H | CO$_2$Me | Me | O |
| 4-Cl | 5-OCF$_2$H | CO$_2$Me | Me | O |
| 4-Br | 5-OCF$_2$H | CO$_2$Me | Me | O |
| 4-OCF$_3$ | 5-OCF$_2$H | CO$_2$Me | Me | O |
| 4-OCF$_2$H | 5-OCF$_2$H | CO$_2$Me | Me | O |
| 4-CF$_3$ | 5-Cl | CO$_2$Me | Et | O |
| 4-Cl | 5-Cl | CO$_2$Me | Et | O |
| 4-Br | 5-Cl | CO$_2$Me | Et | O |
| 4-CF$_3$ | 5-Cl | CO$_2$Me | CH$_2$Ph | O |
| 4-Cl | 5-Cl | CO$_2$Me | CH$_2$Ph | O |
| 4-Br | 5-Cl | CO$_2$Me | CH$_2$Ph | O |
| 4-CF$_3$ | 5-Cl | CO$_2$Me | allyl | O |
| 4-Cl | 5-Cl | CO$_2$Me | allyl | O |
| 4-Br | 5-Cl | CO$_2$Me | allyl | O |
| 4-CF$_3$ | 5-F | CO$_2$Et | Me | O |
| 4-Cl | 5-F | CO$_2$Et | Me | O |
| 4-Br | 5-F | CO$_2$Et | Me | O |
| 4-CF$_3$ | 5-F | CO$_2$CH$_2$CF$_3$ | Me | O |
| 4-Cl | 5-F | CO$_2$CH$_2$CF$_3$ | Me | O |
| 4-Br | 5-F | CO$_2$CH$_2$CF$_3$ | Me | O |
| 4-CF$_3$ | 5-F | CO$_2$Ph | Me | O |
| 4-Cl | 5-F | CO$_2$Ph | Me | O |
| 4-Br | 5-F | CO$_2$Ph | Me | O |
| 4-CF$_3$ | 5-Cl | CO$_2$H | H | O |
| 4-CF$_3$ | 5-Cl | CONHMe | H | O |
| 4-CF$_3$ | 5-Cl | CONMe | H | O |
| 4-CF$_3$ | 5-Cl | CONHPh | H | O |
| 4-CF$_3$ | 5-Cl | CSNMe$_2$ | H | O |
| 4-CF$_3$ | 5-Cl | propargyl | Me | O |
| 4-CF$_3$ | 5-Cl | CH$_2$CH$_2$CN | Me | O |
| 4-CF$_3$ | 5-Cl | CH$_2$CO$_2$Me | Me | O |
| 4-CF$_3$ | 5-Cl | CH$_2$OMe | Me | O |
| 4-CF$_3$ | 5-Cl | OMe | H | O |
| 4-CF$_3$ | 5-Cl | SMe | H | O |
| 4-CF$_3$ | 5-Cl | SO$_2$Me | H | O |
| 4-CF$_3$ | 5-Cl | C(O)Me | Me | O |
| 4-CF$_3$ | 5-Cl | C(O)Et | Me | O |
| 4-CF$_3$ | 5-Cl | C(O)Me | H | O |
| 4-CF$_3$ | 5-Cl | C(O)Et | H | O |
| 4-CF$_3$ | 5-Cl | CN | Me | O |
| 4-CF$_3$ | 5-Cl | CN | Et | O |
| 4-CF$_3$ | 5-Cl | CN | CH$_2$Ph | O |
| 4-CF$_3$ | 5-Cl | CN | H | O |
| 4-CF$_3$ | H | H | H | S |
| 4-Cl | H | H | H | S |
| 4-Br | H | H | H | S |
| 4-OCF$_2$H | H | H | H | S |
| 4-CF$_3$ | 4-F | H | H | S |
| 4-Cl | 4-F | H | H | S |
| 4-Br | 4-F | H | H | S |
| 4-OCF$_2$H | 4-F | H | H | S |
| 4-CF$_3$ | 4-Cl | H | H | S |
| 4-Cl | 4-Cl | H | H | S |
| 4-Br | 4-Cl | H | H | S |
| 4-OCF$_2$H | 4-Cl | H | H | S |
| 4-CF$_3$ | 5-F | H | H | S |
| 4-Cl | 5-F | H | H | S |
| 4-Br | 5-F | H | H | S |
| 4-OCF$_2$H | 5-F | H | H | S |
| 4-CF$_3$ | 4-F | Me | H | S |
| 4-Cl | 4-F | Me | H | S |
| 4-Br | 4-F | Me | H | S |
| 4-OCF$_2$H | 4-F | Me | H | S |

TABLE 12-continued

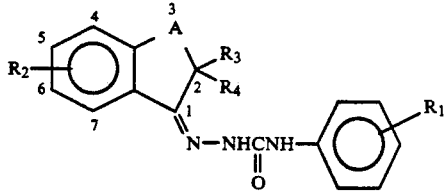

| R₁ | R₂ | R₃ | R₄ | A |
|---|---|---|---|---|
| 4-CF₃ | 5-Cl | Me | H | S |
| 4-Cl | 5-Cl | Me | H | S |
| 4-Br | 5-Cl | Me | H | S |
| 4-OCF₂H | 5-Cl | Me | H | S |
| 4-CF₃ | 5-OCF₂H | Me | H | S |
| 4-Cl | 5-OCF₂H | Me | H | S |
| 4-Br | 5-OCF₂H | Me | H | S |
| 4-OCF₂H | 5-OCF₂H | Me | H | S |
| 4-CF₃ | 5-F | Me | H | S |
| 4-Cl | 5-F | Me | H | S |
| 4-Br | 5-F | Me | H | S |
| 4-CF₃ | 5-Cl | Et | H | S |
| 4-Cl | 5-Cl | Et | H | S |
| 4-Br | 5-Cl | Et | H | S |
| 4-CF₃ | 5-OCF₂H | Et | H | S |
| 4-Cl | 5-OCF₂H | Et | H | S |
| 4-Br | 5-OCF₂H | Et | H | S |
| 4-CF₃ | 5-F | n-Bu | H | S |
| 4-Cl | 5-F | n-Bu | H | S |
| 4-Br | 5-F | n-Bu | H | S |
| 4-CF₃ | 4-F | n-Bu | H | S |
| 4-Cl | 4-F | n-Bu | H | S |
| 4-Br | 4-F | n-Bu | H | S |
| 4-CF₃ | 5-Cl | allyl | H | S |
| 4-Cl | 5-Cl | allyl | H | S |
| 4-Br | 5-Cl | allyl | H | S |
| 4-CF₃ | 5-Cl | Me | Me | S |
| 4-Cl | 5-Cl | Me | Me | S |
| 4-Br | 5-Cl | Me | Me | S |
| 4-CF₃ | 5-F | Me | Me | S |
| 4-Cl | 5-F | Me | Me | S |
| 4-Br | 5-F | Me | Me | S |
| 4-CF₃ | 5-OCF₂H | Me | Me | S |
| 4-Cl | 5-OCF₂H | Me | Me | S |
| 4-Br | 5-OCF₂H | Me | Me | S |
| 4-CF₃ | 5-OCF₃ | Me | Me | S |
| 4-Cl | 5-OCF₃ | Me | Me | S |
| 4-Br | 5-OCF₃ | Me | Me | S |
| 4-CF₃ | 4-F | Me | Me | S |
| 4-Cl | 4-F | Me | Me | S |
| 4-Br | 4-F | Me | Me | S |
| 4-CF₃ | 5-Br | Me | Me | S |
| 4-Cl | 5-Br | Me | Me | S |
| 4-Br | 5-Br | Me | Me | S |
| 4-CF₃ | 5-Cl | CH₂Ph | H | S |
| 4-Cl | 5-Cl | CH₂Ph | H | S |
| 4-Br | 5-Cl | CH₂Ph | H | S |
| 4-OCF₃ | 5-Cl | CH₂Ph | H | S |
| 4-OCF₂H | 5-Cl | CH₂Ph | H | S |
| 4-CF₃ | 5-F | CH₂Ph-4-F | H | S |
| 4-Cl | 5-F | CH₂Ph-4-F | H | S |
| 4-Br | 5-F | CH₂Ph-4-F | H | S |
| 4-OCF₂H | 5-F | CH₂Ph-4-F | H | S |
| 4-OCF₃ | 5-F | CH₂Ph-4-F | H | S |
| 4-CF₃ | 5-OCF₂H | CH₂Ph-4-F | H | S |
| 4-Cl | 5-OCF₂H | CH₂Ph-4-F | H | S |
| 4-Br | 5-OCF₂H | CH₂Ph-4-F | H | S |
| 4-OCF₃ | 5-OCF₂H | CH₂Ph-4-F | H | S |
| 4-OCF₂H | 5-OCF₂H | CH₂Ph-4-F | H | S |
| 4-CF₃ | 5-Cl | CH₂Ph-4-Cl | H | S |
| 4-Cl | 5-Cl | CH₂Ph-4-Cl | H | S |
| 4-Br | 5-Cl | CH₂Ph-4-Cl | H | S |
| 4-OCF₃ | 5-Cl | CH₂Ph-4-Cl | H | S |
| 4-OCF₂H | 5-Cl | CH₂Ph-4-Cl | H | S |
| 4-CF₃ | H | CO₂Me | H | S |
| 4-Cl | H | CO₂Me | H | S |
| 4-Br | H | CO₂Me | H | S |
| 4-OCF₂H | H | CO₂Me | H | S |
| 4-F | H | CO₂Me | H | S |
| 4-CF₃ | 5-Cl | CO₂Me | H | S |
| 4-Cl | 5-Cl | CO₂Me | H | S |

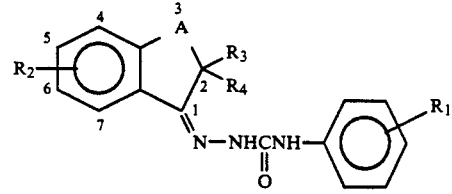

| R₁ | R₂ | R₃ | R₄ | A |
|---|---|---|---|---|
| 4-Br | 5-Cl | CO₂Me | H | S |
| 4-OCF₂H | 5-Cl | CO₂Me | H | S |
| 4-OCF₃ | 5-Cl | CO₂Me | H | S |
| 4-NO₂ | 5-Cl | CO₂Me | H | S |
| 4-CF₃ | 5-F | CO₂Me | H | S |
| 4-Cl | 5-F | CO₂Me | H | S |
| 4-Br | 5-F | CO₂Me | H | S |
| 4-OCF₂H | 5-F | CO₂Me | H | S |
| 4-OCF₃ | 5-F | CO₂Me | H | S |
| 4-CN | 5-F | CO₂Me | H | S |
| 4-CF₃ | 4-F | CO₂Me | H | S |
| 4-Cl | 4-F | CO₂Me | H | S |
| 4-Br | 4-F | CO₂Me | H | S |
| 4-CF₃ | 4-Cl | CO₂Me | H | S |
| 4-Cl | 4-Cl | CO₂Me | H | S |
| 4-Br | 4-Cl | CO₂Me | H | S |
| 4-CF₃ | H | CO₂Me | Me | S |
| 4-Cl | H | CO₂Me | Me | S |
| 4-Br | H | CO₂Me | Me | S |
| 4-OCF₂H | H | CO₂Me | Me | S |
| 4-OCF₃ | H | CO₂Me | Me | S |
| 3,4-CF₂CF₂O | H | CO₂Me | Me | S |
| 3,4-CH₂C(Me)₂O | H | CO₂Me | Me | S |
| 4-CF₃ | 5-Cl | CO₂Me | Me | S |
| 4-Cl | 5-Cl | CO₂Me | Me | S |
| 4-Br | 5-Cl | CO₂Me | Me | S |
| 4-OCF₂H | 5-Cl | CO₂Me | Me | S |
| 4-OCF₃ | 5-Cl | CO₂Me | Me | S |
| 3,4-CF₂CF₂O | 5-Cl | CO₂Me | Me | S |
| 3,4-CF₂C(Me)₂O | 5-Cl | CO₂Me | Me | S |
| 4-CF₃ | 5-F | CO₂Me | Me | S |
| 4-Cl | 5-F | CO₂Me | Me | S |
| 4-Br | 5-F | CO₂Me | Me | S |
| 4-OCF₂H | 5-F | CO₂Me | Me | S |
| 4-OCF₃ | 5-F | CO₂Me | Me | S |
| 3,4-CF₂CF₂O | 5-F | CO₂Me | Me | S |
| 3,4-CH₂C(Me)₂O | 5-F | CO₂Me | Me | S |
| 4-CF₃ | 4-F | CO₂Me | Me | S |
| 4-Cl | 4-F | CO₂Me | Me | S |
| 4-Br | 4-F | CO₂Me | Me | S |
| 4-OCF₃ | 4-F | CO₂Me | Me | S |
| 4-OCF₂H | 4-F | CO₂Me | Me | S |
| 3,4-CF₂CF₂O | 4-F | CO₂Me | Me | S |
| 3,4-CH₂C(Me)₂O | 4-F | CO₂Me | Me | S |
| 4-CF₃ | 5-OCF₂H | CO₂Me | Me | S |
| 4-Cl | 5-OCF₂H | CO₂Me | Me | S |
| 4-Br | 5-OCF₂H | CO₂Me | Me | S |
| 4-OCF₃ | 5-OCF₂H | CO₂Me | Me | S |
| 4-OCF₂H | 5-OCF₂H | CO₂Me | Me | S |
| 3,4-CF₂CF₂O | 5-OCF₂H | CO₂Me | Me | S |
| 3,4-CH₂C(Me)₂O | 5-OCF₂H | CO₂Me | Me | S |
| 4-OCF₂H | 6-F | CO₂Me | Me | S |
| 4-OCF₃ | 6-F | CO₂Me | Me | S |
| 4-CF₃ | 5-Cl | CO₂Me | Et | S |
| 4-Cl | 5-Cl | CO₂Me | Et | S |
| 4-Br | 5-Cl | CO₂Me | Et | S |
| 4-CF₃ | 5-Cl | CO₂Me | CH₂Ph | S |
| 4-Cl | 5-Cl | CO₂Me | CH₂Ph | S |
| 4-Br | 5-Cl | CO₂Me | CH₂Ph | S |
| 4-CF₃ | 5-Cl | CO₂Me | allyl | S |
| 4-Cl | 5-Cl | CO₂Me | allyl | S |
| 4-Br | 5-Cl | CO₂Me | allyl | S |
| 4-CF₃ | 5-F | CO₂Et | Me | S |
| 4-Cl | 5-F | CO₂Et | Me | S |
| 4-Br | 5-F | CO₂Et | Me | S |
| 4-CF₃ | 5-F | CO₂CH₂CF₃ | Me | S |
| 4-Cl | 5-F | CO₂CH₂CF₃ | Me | S |
| 4-Br | 5-F | CO₂CH₂CF₃ | Me | S |
| 4-CF₃ | 5-F | CO₂Ph | Me | S |
| 4-Cl | 5-F | CO₂Ph | Me | S |
| 4-Br | 5-F | CO₂Ph | Me | S |

TABLE 12-continued

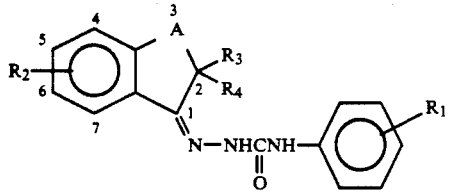

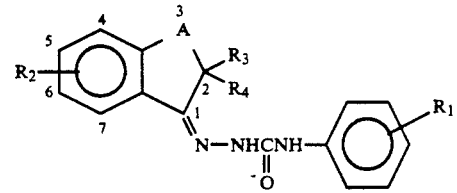

| R₁ | R₂ | R₃ | R₄ | A |
|---|---|---|---|---|
| 4-CF₃ | 5-Cl | CO₂H | H | S |
| 4-CF₃ | 5-Cl | CONHMe | H | S |
| 4-CF₃ | 5-Cl | CONMe | H | S |
| 4-CF₃ | 5-Cl | CONHPh | H | S |
| 4-CF₃ | 5-Cl | CSNMe₂ | H | S |
| 4-CF₃ | 5-Cl | propargyl | Me | S |
| 4-CF₃ | 5-Cl | CH₂CH₂CN | Me | S |
| 4-CF₃ | 5-Cl | CH₂CO₂Me | Me | S |
| 4-CF₃ | 5-Cl | CH₂OMe | H | S |
| 4-CF₃ | 5-Cl | OMe | H | S |
| 4-CF₃ | 5-Cl | SMe | H | S |
| 4-CF₃ | 5-Cl | SO₂Me | H | S |
| 4-CF₃ | 5-Cl | C(O)Me | Me | S |
| 4-CF₃ | 5-Cl | C(O)Et | Me | S |
| 4-CF₃ | 5-Cl | C(O)Me | H | S |
| 4-CF₃ | 5-Cl | C(O)Et | H | S |
| 4-CF₃ | 5-Cl | CN | Me | S |
| 4-CF₃ | 5-Cl | CN | Et | S |
| 4-CF₃ | 5-Cl | CN | CH₂Ph | S |
| 4-CF₃ | 5-Cl | CN | H | S |
| 4-CF₃ | 4-F | allyl | H | OCH₂ |
| 4-Cl | 4-F | allyl | H | OCH₂ |
| 4-Br | 4-F | allyl | H | OCH₂ |
| 4-OCF₂H | 4-F | allyl | H | OCH₂ |
| 4-OCF₃ | 4-F | allyl | H | OCH₂ |
| 4-CF₃ | 4-Cl | allyl | H | OCH₂ |
| 4-Cl | 4-Cl | allyl | H | OCH₂ |
| 4-Br | 4-Cl | allyl | H | OCH₂ |
| 4-OCF₂H | 4-Cl | allyl | H | OCH₂ |
| 4-OCF₃ | 4-Cl | allyl | H | OCH₂ |
| 4-CF₃ | 5-F | propargyl | H | OCH₂ |
| 4-Cl | 5-F | propargyl | H | OCH₂ |
| 4-Br | 5-F | propargyl | H | OCH₂ |
| 4-OCF₂H | 5-F | propargyl | H | OCH₂ |
| 4-OCF₃ | 5-F | propargyl | H | OCH₂ |
| 4-CF₃ | 5-Cl | Me | H | OCH₂ |
| 4-Cl | 5-Cl | Me | H | OCH₂ |
| 4-Br | 5-Cl | Me | H | OCH₂ |
| 4-OCF₂H | 5-Cl | Me | H | OCH₂ |
| 4-OCF₃ | 5-Cl | Me | H | OCH₂ |
| 4-CF₃ | 5-CF₃ | Me | H | OCH₂ |
| 4-Cl | 5-CF₃ | Me | H | OCH₂ |
| 4-Br | 5-CF₃ | Me | H | OCH₂ |
| 4-OCF₂H | 5-CF₃ | Me | H | OCH₂ |
| 4-OCF₃ | 5-CF₃ | Me | H | OCH₂ |
| 4-CF₃ | 5-OCF₂H | Me | H | OCH₂ |
| 4-Cl | 5-OCF₂H | Me | H | OCH₂ |
| 4-Br | 5-OCF₂H | Me | H | OCH₂ |
| 4-OCF₂H | 5-OCF₂H | Me | H | OCH₂ |
| 4-OCF₃ | 5-OCF₂H | Me | H | OCH₂ |
| 4-CF₃ | 4-F | CH₂Ph | H | OCH₂ |
| 4-Cl | 4-F | CH₂Ph | H | OCH₂ |
| 4-Br | 4-F | CH₂Ph | H | OCH₂ |
| 4-OCF₂H | 4-F | CH₂Ph | H | OCH₂ |
| 4-OCF₃ | 4-F | CH₂Ph | H | OCH₂ |
| 4-CF₃ | 4-Cl | CH₂Ph | H | OCH₂ |
| 4-Cl | 4-Cl | CH₂Ph | H | OCH₂ |
| 4-Br | 4-Cl | CH₂Ph | H | OCH₂ |
| 4-OCF₂H | 4-Cl | CH₂Ph | H | OCH₂ |
| 4-OCF₃ | 4-Cl | CH₂Ph | H | OCH₂ |
| 4-CF₃ | 5-F | CH₂Ph | H | OCH₂ |
| 4-Cl | 5-F | CH₂Ph | H | OCH₂ |
| 4-Br | 5-F | CH₂Ph | H | OCH₂ |
| 4-OCF₂H | 5-F | CH₂Ph | H | OCH₂ |
| 4-OCF₃ | 5-F | CH₂Ph | H | OCH₂ |
| 4-CF₃ | 5-Cl | CH₂Ph-4-Cl | H | OCH₂ |
| 4-Cl | 5-Cl | CH₂Ph-4-Cl | H | OCH₂ |
| 4-Br | 5-Cl | CH₂Ph-4-Cl | H | OCH₂ |
| 4-OCF₂H | 5-Cl | CH₂Ph-4-Cl | H | OCH₂ |
| 4-OCF₃ | 5-Cl | CH₂Ph-4-Cl | H | OCH₂ |
| 4-CF₃ | 5-CF₃ | CH₂Ph-4-Cl | H | OCH₂ |
| 4-Cl | 5-CF₃ | CH₂Ph-4-Cl | H | OCH₂ |
| 4-Br | 5-CF₃ | CH₂Ph-4-Cl | H | OCH₂ |
| 4-OCF₂H | 5-CF₃ | CH₂Ph-4-Cl | H | OCH₂ |
| 4-OCF₃ | 5-CF₃ | CH₂Ph-4-Cl | H | OCH₂ |
| 4-CF₃ | 5-OCF₂H | CH₂Ph-4-Cl | H | OCH₂ |
| 4-Cl | 5-OCF₂H | CH₂Ph-4-Cl | H | OCH₂ |
| 4-Br | 5-OCF₂H | CH₂Ph-4-Cl | H | OCH₂ |
| 4-OCF₂H | 5-OCF₂H | CH₂Ph-4-Cl | H | OCH₂ |
| 4-OCF₃ | 5-OCF₂H | CH₂Ph-4-Cl | H | OCH₂ |
| 4-CF₃ | 4-F | CO₂Me | H | OCH₂ |
| 4-Cl | 4-F | CO₂Me | H | OCH₂ |
| 4-Br | 4-F | CO₂Me | H | OCH₂ |
| 4-OCF₂H | 4-F | CO₂Me | H | OCH₂ |
| 4-OCF₃ | 4-F | CO₂Me | H | OCH₂ |
| 4-CF₃ | 4-Cl | CO₂Me | H | OCH₂ |
| 4-Cl | 4-Cl | CO₂Me | H | OCH₂ |
| 4-Br | 4-Cl | CO₂Me | H | OCH₂ |
| 4-OCF₂H | 4-Cl | CO₂Me | H | OCH₂ |
| 4-OCF₃ | 4-Cl | CO₂Me | H | OCH₂ |
| 4-CF₃ | 5-F | CO₂Me | H | OCH₂ |
| 4-Cl | 5-F | CO₂Me | H | OCH₂ |
| 4-Br | 5-F | CO₂Me | H | OCH₂ |
| 4-OCF₂H | 5-F | CO₂Me | H | OCH₂ |
| 4-OCF₃ | 5-F | CO₂Me | H | OCH₂ |
| 4-CF₃ | 5-Cl | CO₂Me | H | OCH₂ |
| 4-Cl | 5-Cl | CO₂Me | H | OCH₂ |
| 4-Br | 5-Cl | CO₂Me | H | OCH₂ |
| 4-OCF₂H | 5-Cl | CO₂Me | H | OCH₂ |
| 4-OCF₃ | 5-Cl | CO₂Me | H | OCH₂ |
| 4-CF₃ | 5-CF₃ | CO₂Me | H | OCH₂ |
| 4-Cl | 5-CF₃ | CO₂Me | H | OCH₂ |
| 4-Br | 5-CF₃ | CO₂Me | H | OCH₂ |
| 4-OCF₂H | 5-CF₃ | CO₂Me | H | OCH₂ |
| 4-OCF₃ | 5-CF₃ | CO₂Me | H | OCH₂ |
| 4-CF₃ | 5-OCF₂H | CO₂Me | H | OCH₂ |
| 4-Cl | 5-OCF₂H | CO₂Me | H | OCH₂ |
| 4-Br | 5-OCF₂H | CO₂Me | H | OCH₂ |
| 4-OCF₂H | 5-OCF₂H | CO₂Me | H | OCH₂ |
| 4-OCF₃ | 5-OCF₂H | CO₂Me | H | OCH₂ |
| 4-CF₃ | 4-F | CO₂Me | Me | OCH₂ |
| 4-Cl | 4-F | CO₂Me | Me | OCH₂ |
| 4-Br | 4-F | CO₂Me | Me | OCH₂ |
| 4-OCF₂H | 4-F | CO₂Me | Me | OCH₂ |
| 4-OCF₃ | 4-F | CO₂Me | Me | OCH₂ |
| 4-CF₃ | 4-Cl | CO₂Me | Me | OCH₂ |
| 4-Cl | 4-Cl | CO₂Me | Me | OCH₂ |
| 4-Br | 4-Cl | CO₂Me | Me | OCH₂ |
| 4-OCF₂H | 4-Cl | CO₂Me | Me | OCH₂ |
| 4-OCF₃ | 4-Cl | CO₂Me | Me | OCH₂ |
| 4-CF₃ | 5-F | CO₂Me | Me | OCH₂ |
| 4-Cl | 5-F | CO₂Me | Me | OCH₂ |
| 4-Br | 5-F | CO₂Me | Me | OCH₂ |
| 4-OCF₂H | 5-F | CO₂Me | Me | OCH₂ |
| 4-OCF₃ | 5-F | CO₂Me | Me | OCH₂ |
| 4-CF₃ | 5-Cl | CO₂Me | Me | OCH₂ |
| 4-Cl | 5-Cl | CO₂Me | Me | OCH₂ |
| 4-Br | 5-Cl | CO₂Me | Me | OCH₂ |
| 4-OCF₂H | 5-Cl | CO₂Me | Me | OCH₂ |
| 4-OCF₃ | 5-Cl | CO₂Me | Me | OCH₂ |
| 4-CF₃ | 5-CF₃ | CO₂Me | Me | OCH₂ |
| 4-Cl | 5-CF₃ | CO₂Me | Me | OCH₂ |
| 4-Br | 5-CF₃ | CO₂Me | Me | OCH₂ |
| 4-OCF₂H | 5-CF₃ | CO₂Me | Me | OCH₂ |
| 4-OCF₃ | 5-CF₃ | CO₂Me | Me | OCH₂ |
| 4-CF₃ | 5-OCF₂H | CO₂Me | Me | OCH₂ |
| 4-Cl | 5-OCF₂H | CO₂Me | Me | OCH₂ |
| 4-Br | 5-OCF₂H | CO₂Me | Me | OCH₂ |
| 4-OCF₂H | 5-OCF₂H | CO₂Me | Me | OCH₂ |
| 4-OCF₃ | 5-OCF₂H | CO₂Me | Me | OCH₂ |
| 4-CF₃ | 4-F | Me | H | SCH₂ |
| 4-Cl | 4-F | Me | H | SCH₂ |

TABLE 12-continued

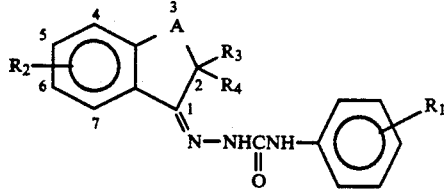

| R₁ | R₂ | R₃ | R₄ | A |
|---|---|---|---|---|
| 4-Br | 4-F | Me | H | SCH₂ |
| 4-OCF₂H | 4-F | Me | H | SCH₂ |
| 4-OCF₃ | 4-F | Me | H | SCH₂ |
| 4-CF₃ | 4-Cl | Me | H | SCH₂ |
| 4-Cl | 4-Cl | Me | H | SCH₂ |
| 4-Br | 4-Cl | Me | H | SCH₂ |
| 4-OCF₂H | 4-Cl | Me | H | SCH₂ |
| 4-OCF₃ | 4-Cl | Me | H | SCH₂ |
| 4-CF₃ | 5-F | allyl | H | SCH₂ |
| 4-Cl | 5-F | allyl | H | SCH₂ |
| 4-Br | 5-F | allyl | H | SCH₂ |
| 4-OCF₂H | 5-F | allyl | H | SCH₂ |
| 4-OCF₃ | 5-F | allyl | H | SCH₂ |
| 4-CF₃ | 5-Cl | CH₂Ph | H | SCH₂ |
| 4-Cl | 5-Cl | CH₂Ph | H | SCH₂ |
| 4-Br | 5-Cl | CH₂Ph | H | SCH₂ |
| 4-OCF₂H | 5-Cl | CH₂Ph | H | SCH₂ |
| 4-OCF₃ | 5-Cl | CH₂Ph | H | SCH₂ |
| 4-CF₃ | 5-CF₃ | CH₂Ph-4-Cl | H | SCH₂ |
| 4-Cl | 5-CF₃ | CH₂Ph-4-Cl | H | SCH₂ |
| 4-Br | 5-CF₃ | CH₂Ph-4-Cl | H | SCH₂ |
| 4-OCF₂H | 5-CF₃ | CH₂Ph-4-Cl | H | SCH₂ |
| 4-OCF₃ | 5-CF₃ | CH₂Ph-4-Cl | H | SCH₂ |
| 4-CF₃ | 5-OCF₂H | CH₂Ph-4-Cl | H | SCH₂ |
| 4-Cl | 5-OCF₂H | CH₂Ph-4-Cl | H | SCH₂ |
| 4-Br | 5-OCF₂H | CH₂Ph-4-Cl | H | SCH₂ |
| 4-OCF₂H | 5-OCF₂H | CH₂Ph-4-Cl | H | SCH₂ |
| 4-OCF₃ | 5-OCF₂H | CH₂Ph-4-Cl | H | SCH₂ |
| 4-CF₃ | 4-F | CO₂Me | H | SCH₂ |
| 4-Cl | 4-F | CO₂Me | H | SCH₂ |
| 4-Br | 4-F | CO₂Me | H | SCH₂ |
| 4-OCF₂H | 4-F | CO₂Me | H | SCH₂ |
| 4-OCF₃ | 4-F | CO₂Me | H | SCH₂ |
| 4-CF₃ | 4-Cl | CO₂Me | H | SCH₂ |
| 4-Cl | 4-Cl | CO₂Me | H | SCH₂ |
| 4-Br | 4-Cl | CO₂Me | H | SCH₂ |
| 4-OCF₂H | 4-Cl | CO₂Me | H | SCH₂ |
| 4-OCF₃ | 4-Cl | CO₂Me | H | SCH₂ |
| 4-CF₃ | 5-F | CO₂Me | H | SCH₂ |
| 4-Cl | 5-F | CO₂Me | H | SCH₂ |
| 4-Br | 5-F | CO₂Me | H | SCH₂ |
| 4-OCF₂H | 5-F | CO₂Me | H | SCH₂ |
| 4-OCF₃ | 5-F | CO₂Me | H | SCH₂ |
| 4-CF₃ | 5-Cl | CO₂Me | H | SCH₂ |

TABLE 12-continued

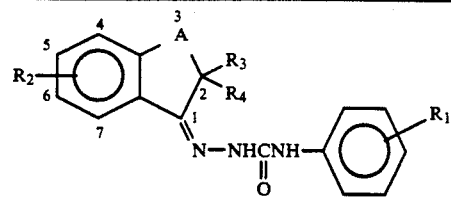

| R₁ | R₂ | R₃ | R₄ | A |
|---|---|---|---|---|
| 4-Cl | 5-Cl | CO₂Me | H | SCH₂ |
| 4-Br | 5-Cl | CO₂Me | H | SCH₂ |
| 4-OCF₂H | 5-Cl | CO₂Me | H | SCH₂ |
| 4-OCF₃ | 5-Cl | CO₂Me | H | SCH₂ |
| 4-CF₃ | 5-CF₃ | CO₂Me | H | SCH₂ |
| 4-Cl | 5-CF₃ | CO₂Me | H | SCH₂ |
| 4-Br | 5-CF₃ | CO₂Me | H | SCH₂ |
| 4-OCF₂H | 5-CF₃ | CO₂Me | H | SCH₂ |
| 4-OCF₃ | 5-CF₃ | CO₂Me | H | SCH₂ |
| 4-CF₃ | 5-OCF₂H | CO₂Me | H | SCH₂ |
| 4-Cl | 5-OCF₂H | CO₂Me | H | SCH₂ |
| 4-Br | 5-OCF₂H | CO₂Me | H | SCH₂ |
| 4-OCF₂H | 5-OCF₂H | CO₂Me | H | SCH₂ |
| 4-OCF₃ | 5-OCF₂H | CO₂Me | H | SCH₂ |
| 4-CF₃ | 4-F | CO₂Me | Me | SCH₂ |
| 4-Cl | 4-F | CO₂Me | Me | SCH₂ |
| 4-Br | 4-F | CO₂Me | Me | SCH₂ |
| 4-OCF₂H | 4-F | CO₂Me | Me | SCH₂ |
| 4-OCF₃ | 4-F | CO₂Me | Me | SCH₂ |
| 4-CF₃ | 4-Cl | CO₂Me | Me | SCH₂ |
| 4-Cl | 4-Cl | CO₂Me | Me | SCH₂ |
| 4-Br | 4-Cl | CO₂Me | Me | SCH₂ |
| 4-OCF₂H | 4-Cl | CO₂Me | Me | SCH₂ |
| 4-OCF₃ | 4-Cl | CO₂Me | Me | SCH₂ |
| 4-CF₃ | 5-F | CO₂Me | Me | SCH₂ |
| 4-Cl | 5-F | CO₂Me | Me | SCH₂ |
| 4-Br | 5-F | CO₂Me | Me | SCH₂ |
| 4-OCF₂H | 5-F | CO₂Me | Me | SCH₂ |
| 4-OCF₃ | 5-F | CO₂Me | Me | SCH₂ |
| 4-CF₃ | 5-Cl | CO₂Me | Me | SCH₂ |
| 4-Cl | 5-Cl | CO₂Me | Me | SCH₂ |
| 4-Br | 5-Cl | CO₂Me | Me | SCH₂ |
| 4-OCF₂H | 5-Cl | CO₂Me | Me | SCH₂ |
| 4-OCF₃ | 5-Cl | CO₂Me | Me | SCH₂ |
| 4-CF₃ | 5-CF₃ | CO₂Me | Me | SCH₂ |
| 4-Cl | 5-CF₃ | CO₂Me | Me | SCH₂ |
| 4-Br | 5-CF₃ | CO₂Me | Me | SCH₂ |
| 4-OCF₂H | 5-CF₃ | CO₂Me | Me | SCH₂ |
| 4-OCF₃ | 5-CF₃ | CO₂Me | Me | SCH₂ |
| 4-CF₃ | 5-OCF₂H | CO₂Me | Me | SCH₂ |
| 4-Cl | 5-OCF₂H | CO₂Me | Me | SCH₂ |
| 4-Br | 5-OCF₂H | CO₂Me | Me | SCH₂ |
| 4-OCF₂H | 5-OCF₂H | CO₂Me | Me | SCH₂ |
| 4-OCF₃ | 5-OCF₂H | CO₂Me | Me | SCH₂ |

TABLE 13

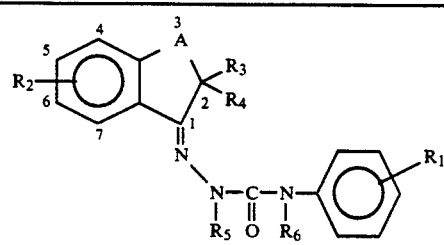

| R₁ | R₂ | R₃ | R₄ | R₅ | R₆ | A |
|---|---|---|---|---|---|---|
| 4-CF₃ | 5-Cl | Ph | H | Me | H | CH₂ |
| 4-Cl | 5-Cl | Ph | H | Me | H | CH₂ |
| 4-Br | 5-Cl | Ph | H | Me | H | CH₂ |
| 4-CF₃ | 5-Cl | Ph | H | C(O)Me | H | CH₂ |
| 4-Cl | 5-Cl | Ph | H | C(O)Me | H | CH₂ |
| 4-Br | 5-Cl | Ph | H | C(O)Me | H | CH₂ |
| 4-CF₃ | 5-Cl | Ph | H | CO₂Me | H | CH₂ |
| 4-Cl | 5-Cl | Ph | H | CO₂Me | H | CH₂ |
| 4-Br | 5-Cl | Ph | H | CO₂Me | H | CH₂ |

TABLE 13-continued

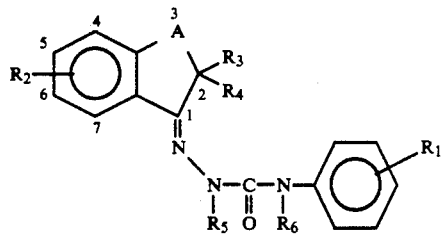

| R₁ | R₂ | R₃ | R₄ | R₅ | R₆ | A |
|---|---|---|---|---|---|---|
| 4-CF₃ | 5-Cl | Ph | H | Ph | H | CH₂ |
| 4-Cl | 5-Cl | Ph | H | Ph | H | CH₂ |
| 4-Br | 5-Cl | Ph | H | Ph | H | CH₂ |
| 4-CF₃ | 5-Cl | Ph | H | 4-Cl—Ph | H | CH₂ |
| 4-Cl | 5-Cl | Ph | H | 4-Cl—Ph | H | CH₂ |
| 4-Br | 5-Cl | Ph | H | 4-Cl—Ph | H | CH₂ |
| 4-CF₃ | 5-Cl | Ph | H | 4-F—Ph | H | CH₂ |
| 4-Cl | 5-Cl | Ph | H | 4-F—Ph | H | CH₂ |
| 4-Br | 5-Cl | Ph | H | 5-F—Ph | H | CH₂ |
| 4-CF₃ | 5-F | Ph | H | Me | H | CH₂ |
| 4-Cl | 5-F | Ph | H | Me | H | CH₂ |
| 4-Br | 5-F | Ph | H | Me | H | CH₂ |
| 4-CF₃ | 5-F | Ph | H | Ph | H | CH₂ |
| 4-Cl | 5-F | Ph | H | Ph | H | CH₂ |
| 4-Br | 5-F | Ph | H | Ph | H | CH₂ |
| 4-CF₃ | 5-F | Ph | H | SN(Me)CO₂n-Bu | H | CH₂ |
| 4-Cl | 5-F | Ph | H | SN(Me)CO₂n-Bu | H | CH₂ |
| 4-Br | 5-F | Ph | H | SN(Me)CO₂n-Bu | H | CH₂ |
| 4-CF₃ | 5-F | Ph | H | SN(i-Pr)CO₂Et | H | CH₂ |
| 4-Cl | 5-F | Ph | H | SN(i-Pr)CO₂Et | H | CH₂ |
| 4-Br | 5-F | Ph | H | SN(i-Pr)CO₂Et | H | CH₂ |
| 4-CF₃ | 5-F | Ph | H | SCO₂n-Hex | H | CH₂ |
| 4-Cl | 5-F | Ph | H | SCO₂n-Hex | H | CH₂ |
| 4-Br | 5-F | Ph | H | SCO₂n-Hex | H | CH₂ |
| 4-CF₃ | 5-F | Ph | H | SN(Me)SO₂Me | H | CH₂ |
| 4-Cl | 5-F | Ph | H | SN(Me)SO₂Me | H | CH₂ |
| 4-Br | 5-F | Ph | H | SN(Me)SO₂Me | H | CH₂ |
| 4-CF₃ | 5-Cl | 4-Cl—Ph | H | Me | H | CH₂ |
| 4-Cl | 5-Cl | 4-Cl—Ph | H | Me | H | CH₂ |
| 4-Br | 5-Cl | 4-Cl—Ph | H | Me | H | CH₂ |
| 4-CF₃ | 5-Cl | 4-Cl—Ph | H | 4-F—Ph | H | CH₂ |
| 4-Cl | 5-Cl | 4-Cl—Ph | H | 4-F—Ph | H | CH₂ |
| 4-Br | 5-Cl | 4-Cl—Ph | H | 4-F—Ph | H | CH₂ |
| 4-CF₃ | 5-Cl | 4-Cl—Ph | H | S—Ph | H | CH₂ |
| 4-Cl | 5-Cl | 4-Cl—Ph | H | S—Ph | H | CH₂ |
| 4-Br | 5-Cl | 4-Cl—Ph | H | S—Ph | H | CH₂ |
| 4-CF₃ | 5-Cl | 4-Cl—Ph | H | CO₂Et | H | CH₂ |
| 4-Cl | 5-Cl | 4-Cl—Ph | H | CO₂Et | H | CH₂ |
| 4-Br | 5-Cl | 4-Cl—Ph | H | CO₂Et | H | CH₂ |
| 4-CF₃ | 5-Cl | 4-Cl—Ph | H | SCO₂n-Bu | H | CH₂ |
| 4-Cl | 5-Cl | 4-Cl—Ph | H | SCO₂n-Bu | H | CH₂ |
| 4-Br | 5-Cl | 4-Cl—Ph | H | SCO₂n-Bu | H | CH₂ |
| 4-CF₃ | 5-Cl | 4-Cl—Ph | H | SMe | H | CH₂ |
| 4-Cl | 5-Cl | 4-Cl—Ph | H | SMe | H | CH₂ |
| 4-Br | 5-Cl | 4-Cl—Ph | H | SMe | H | CH₂ |
| 4-CF₃ | 5-Cl | 4-F—Ph | H | CO₂Me | H | CH₂ |
| 4-Cl | 5-Cl | 4-F—Ph | H | CO₂Me | H | CH₂ |
| 4-Br | 5-Cl | 4-F—Ph | H | CO₂Me | H | CH₂ |
| 4-CF₃ | 5-Cl | 4-F—Ph | H | SN(Me)SO₂-4-Me—Ph | H | CH₂ |
| 4-Cl | 5-Cl | 4-F—Ph | H | SN(Me)SO₂-4-Me—Ph | H | CH₂ |
| 4-Br | 5-Cl | 4-F—Ph | H | SN(Me)SO₂-4-Me—Ph | H | CH₂ |
| 4-CF₃ | 5-Cl | 4-F—Ph | H | SN(Me)P(O)(OEt)₂ | H | CH₂ |
| 4-Cl | 5-Cl | 4-F—Ph | H | SN(Me)P(O)(OEt)₂ | H | CH₂ |
| 4-Br | 5-Cl | 4-F—Ph | H | SN(Me)P(O)(OEt)₂ | H | CH₂ |
| 4-CF₃ | 5-Cl | 4-F—Ph | H | SN(Me)P(O)(OEt)(Et) | H | CH₂ |
| 4-Cl | 5-Cl | 4-F—Ph | H | SN(Me)P(O)(OEt)(Et) | H | CH₂ |

TABLE 13-continued

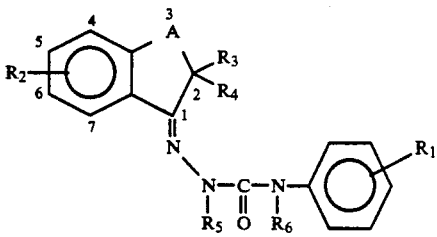

| R$_1$ | R$_2$ | R$_3$ | R$_4$ | R$_5$ | R$_6$ | A |
|---|---|---|---|---|---|---|
| 4-Br | 5-Cl | 4-F—Ph | H | SN(Me)P(=O)(OEt)(Et) | H | CH$_2$ |
| 4-CF$_3$ | 5-Cl | 4-F—Ph | H | CO$_2$Et | H | CH$_2$ |
| 4-Cl | 5-Cl | 4-F—Ph | H | CO$_2$Et | H | CH$_2$ |
| 4-Br | 5-Cl | 4-F—Ph | H | CO$_2$Et | H | CH$_2$ |
| 4-CF$_3$ | 5-Cl | 4-F—Ph | H | Ph | H | CH$_2$ |
| 4-Cl | 5-Cl | 4-F—Ph | H | Ph | H | CH$_2$ |
| 4-Br | 5-Cl | 4-F—Ph | H | Ph | H | CH$_2$ |
| 4-CF$_3$ | 5-Cl | Ph | H | H | Me | CH$_2$ |
| 4-Cl | 5-Cl | Ph | H | H | Me | CH$_2$ |
| 4-Br | 5-Cl | Ph | H | H | Me | CH$_2$ |
| 4-CF$_3$ | 5-Cl | Ph | H | H | C(O)Me | CH$_2$ |
| 4-Cl | 5-Cl | Ph | H | H | C(O)Me | CH$_2$ |
| 4-Br | 5-Cl | Ph | H | H | C(O)Me | CH$_2$ |
| 4-CF$_3$ | 5-Cl | Ph | H | H | CO$_2$Me | CH$_2$ |
| 4-Cl | 5-Cl | Ph | H | H | CO$_2$Me | CH$_2$ |
| 4-Br | 5-Cl | Ph | H | H | CO$_2$Me | CH$_2$ |
| 4-CF$_3$ | 5-Cl | Ph | H | H | CO$_2$Et | CH$_2$ |
| 4-Cl | 5-Cl | Ph | H | H | CO$_2$Et | CH$_2$ |
| 4-Br | 5-Cl | Ph | H | H | CO$_2$Et | CH$_2$ |
| 4-CF$_3$ | 5-Cl | Ph | H | H | C(O)Ph | CH$_2$ |
| 4-Cl | 5-Cl | Ph | H | H | C(O)Ph | CH$_2$ |
| 4-Br | 5-Cl | Ph | H | H | C(O)Ph | CH$_2$ |
| 4-CF$_3$ | 5-Cl | Ph | H | H | C(O)nPr | CH$_2$ |
| 4-Cl | 5-Cl | Ph | H | H | C(O)nPr | CH$_2$ |
| 4-Br | 5-Cl | Ph | H | H | C(O)nPr | CH$_2$ |
| 4-CF3 | 5-F | Ph | H | H | CH$_2$Ph | CH2 |
| 4-Cl | 5-F | Ph | H | H | CH$_2$Ph | CH2 |
| 4-Br | 5-F | Ph | H | H | CH$_2$Ph | CH2 |
| 4-CF$_3$ | 5-F | Ph | H | H | SN(Me)CO$_2$n-dec | CH$_2$ |
| 4-Cl | 5-F | Ph | H | H | SN(Me)CO$_2$n-dec | CH$_2$ |
| 4-Br | 5-F | Ph | H | H | SN(Me)CO$_2$n-dec | CH$_2$ |
| 4-CF$_3$ | 5-F | Ph | H | H | SN(i-Pr)CO$_2$Et | CH$_2$ |
| 4-Cl | 5-F | Ph | H | H | SN(i-Pr)CO$_2$Et | CH$_2$ |
| 4-Br | 5-F | Ph | H | H | SN(i-Pr)CO$_2$Et | CH$_2$ |
| 4-CF$_3$ | 5-F | Ph | H | H | SCO$_2$Et | CH$_2$ |
| 4-Cl | 5-F | Ph | H | H | SCO$_2$Et | CH$_2$ |
| 4-Br | 5-F | Ph | H | H | SCO$_2$Et | CH$_2$ |
| 4-CF$_3$ | 5-F | Ph | H | H | C(O)Me | CH$_2$ |
| 4-Cl | 5-F | Ph | H | H | C(O)Me | CH$_2$ |
| 4-Br | 5-F | Ph | H | H | C(O)Me | CH$_2$ |
| 4-CF$_3$ | 5-F | Ph | H | H | CO$_2$Me | CH$_2$ |
| 4-Cl | 5-F | Ph | H | H | CO$_2$Me | CH$_2$ |
| 4-Br | 5-F | Ph | H | H | CO$_2$Me | CH$_2$ |
| 4-CF$_3$ | 5-Cl | 4-Cl—Ph | H | H | Me | CH$_2$ |
| 4-Cl | 5-Cl | 4-Cl—Ph | H | H | Me | CH$_2$ |
| 4-Br | 5-Cl | 4-Cl—Ph | H | H | Me | CH$_2$ |
| 4-CF$_3$ | 5-Cl | 4-Cl—Ph | H | H | CO$_2$Me | CH$_2$ |
| 4-Cl | 5-Cl | 4-Cl—Ph | H | H | CO$_2$Me | CH$_2$ |
| 4-Br | 5-Cl | 4-Cl—Ph | H | H | CO$_2$Me | CH$_2$ |
| 4-CF$_3$ | 5-Cl | 4-Cl—Ph | H | H | CO$_2$Et | CH$_2$ |
| 4-Cl | 5-Cl | 4-Cl—Ph | H | H | CO$_2$Et | CH$_2$ |
| 4-Br | 5-Cl | 4-Cl—Ph | H | H | CO$_2$Et | CH$_2$ |
| 4-CF$_3$ | 5-Cl | 4-Cl—Ph | H | H | C(O)Me | CH$_2$ |
| 4-Cl | 5-Cl | 4-Cl—Ph | H | H | C(O)Me | CH$_2$ |
| 4-Br | 5-Cl | 4-Cl—Ph | H | H | C(O)Me | CH$_2$ |
| 4-CF$_3$ | 5-Cl | 4-Cl—Ph | H | H | SN(Et)$_2$ | CH$_2$ |
| 4-Cl | 5-Cl | 4-Cl—Ph | H | H | SN(Et)$_2$ | CH$_2$ |
| 4-Br | 5-Cl | 4-Cl—Ph | H | H | SN(Et)$_2$ | CH$_2$ |
| 4-CF$_3$ | 5-Cl | 4-Cl—Ph | H | H | SO$_2$Ph | CH$_2$ |
| 4-Cl | 5-Cl | 4-Cl—Ph | H | H | SO$_2$Ph | CH$_2$ |
| 4-Br | 5-Cl | 4-Cl—Ph | H | H | SO$_2$Ph | CH$_2$ |
| 4-CF$_3$ | 5-Cl | 4-F—Ph | H | H | Me | CH$_2$ |
| 4-Cl | 5-Cl | 4-F—Ph | H | H | Me | CH$_2$ |
| 4-Br | 5-Cl | 4-F—Ph | H | H | Me | CH$_2$ |

TABLE 13-continued

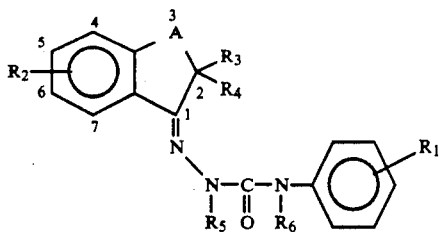

| R₁ | R₂ | R₃ | R₄ | R₅ | R₆ | A |
|---|---|---|---|---|---|---|
| 4-CF₃ | 5-Cl | 4-F—Ph | H | H | C(O)Me | CH₂ |
| 4-Cl | 5-Cl | 4-F—Ph | H | H | C(O)Me | CH₂ |
| 4-Br | 5-Cl | 4-F—Ph | H | H | C(O)Me | CH₂ |
| 4-CF₃ | 5-Cl | 4-F—Ph | H | H | CO₂Me | CH₂ |
| 4-Cl | 5-Cl | 4-F—Ph | H | H | CO₂Me | CH₂ |
| 4-Br | 5-Cl | 4-F—Ph | H | H | CO₂Me | CH₂ |
| 4-CF₃ | 5-Cl | 4-F—Ph | H | H | n-Bu | CH₂ |
| 4-Cl | 5-Cl | 4-F—Ph | H | H | n-Bu | CH₂ |
| 4-Br | 5-Cl | 4-F—Ph | H | H | n-Bu | CH₂ |
| 4-CF₃ | 5-Cl | 4-F—Ph | H | H | SN(Me)CO₂Et | CH₂ |
| 4-Cl | 5-Cl | 4-F—Ph | H | H | SN(Me)CO₂Et | CH₂ |
| 4-Br | 5-Cl | 4-F—Ph | H | H | SN(Me)CO₂Et | CH₂ |
| 4-CF₃ | 5-Cl | 4-F—Ph | H | H | C(O)Ph | CH₂ |
| 4-Cl | 5-Cl | 4-F—Ph | H | H | C(O)Ph | CH₂ |
| 4-Br | 5-Cl | 4-F—Ph | H | H | C(O)Ph | CH₂ |
| 4-CF₃ | 5-Cl | 4-Cl—Ph | Me | H | Me | CH₂ |
| 4-Cl | 5-Cl | 4-Cl—Ph | Me | H | Me | CH₂ |
| 4-Br | 5-Cl | 4-Cl—Ph | Me | H | Me | CH₂ |
| 4-CF₃ | 5-Cl | 4-Cl—Ph | Me | Me | H | CH₂ |
| 4-Cl | 5-Cl | 4-Cl—Ph | Me | Me | H | CH₂ |
| 4-Br | 5-Cl | 4-Cl—Ph | Me | Me | H | CH₂ |
| 4-CF₃ | 5-Cl | 4-Cl—Ph | Me | Ph | H | CH₂ |
| 4-Cl | 5-Cl | 4-Cl—Ph | Me | Ph | H | CH₂ |
| 4-Br | 5-Cl | 4-Cl—Ph | Me | Ph | H | CH₂ |
| 4-CF₃ | 5-Cl | 4-Cl—Ph | Me | H | CO₂Me | CH₂ |
| 4-Cl | 5-Cl | 4-Cl—Ph | Me | H | CO₂Me | CH₂ |
| 4-Br | 5-Cl | 4-Cl—Ph | Me | H | CO₂Me | CH₂ |
| 4-CF₃ | 5-Cl | 4-Cl—Ph | Me | H | C(O)Me | CH₂ |
| 4-Cl | 5-Cl | 4-Cl—Ph | Me | H | C(O)Me | CH₂ |
| 4-Br | 5-Cl | 4-Cl—Ph | Me | H | C(O)Me | CH₂ |
| 4-CF₃ | 5-Cl | 4-Cl—Ph | Me | H | SCO₂Me | CH₂ |
| 4-Cl | 5-Cl | 4-Cl—Ph | Me | H | SCO₂Me | CH₂ |
| 4-Br | 5-Cl | 4-Cl—Ph | Me | H | SCO₂Me | CH₂ |
| 4-CF₃ | 5-Cl | 4-Cl—Ph | H | Me | Me | CH₂ |
| 4-Cl | 5-Cl | 4-Cl—Ph | H | Me | Me | CH₂ |
| 4-Br | 5-Cl | 4-Cl—Ph | H | Me | Me | CH₂ |
| 4-CF₃ | 5-Cl | 4-Cl—Ph | H | Me | C(O)Me | CH₂ |
| 4-Cl | 5-Cl | 4-Cl—Ph | H | Me | C(O)Me | CH₂ |
| 4-Br | 5-Cl | 4-Cl—Ph | H | Me | C(O)Me | CH₂ |
| 4-CF₃ | 5-Cl | 4-Cl—Ph | H | Ph | Me | CH₂ |
| 4-Cl | 5-Cl | 4-Cl—Ph | H | Ph | Me | CH₂ |
| 4-Br | 5-Cl | 4-Cl—Ph | H | Ph | Me | CH₂ |
| 4-CF₃ | 5-Cl | 4-Cl—Ph | H | Ph | CO₂Me | CH₂ |
| 4-Cl | 5-Cl | 4-Cl—Ph | H | Ph | CO₂Me | CH₂ |
| 4-Br | 5-Cl | 4-Cl—Ph | H | Ph | CO₂Me | CH₂ |
| 4-CF₃ | 5-Cl | Ph | H | Me | Me | CH₂ |
| 4-Cl | 5-Cl | Ph | H | Me | Me | CH₂ |
| 4-Br | 5-Cl | Ph | H | Me | Me | CH₂ |
| 4-CF₃ | 5-Cl | Ph | H | CO₂Me | Me | CH₂ |
| 4-Cl | 5-Cl | Ph | H | CO₂Me | Me | CH₂ |
| 4-Br | 5-Cl | Ph | H | CO₂Me | Me | CH₂ |

TABLE 14

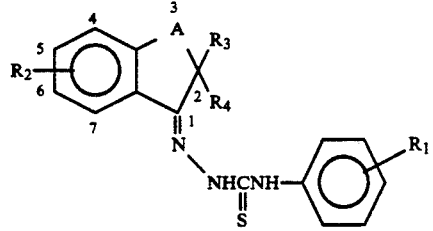

| R₁ | R₂ | R₃ | R₄ | A |
|---|---|---|---|---|
| 4-CF₃ | 5-Cl | Ph | H | CH₂ |
| 4-Cl | 5-Cl | Ph | H | CH₂ |
| 4-Br | 5-Cl | Ph | H | CH₂ |
| 4-OCF₂H | 5-Cl | Ph | H | CH₂ |
| 4-CF₃ | 5-Cl | 4-Cl—Ph | H | CH₂ |
| 4-Cl | 5-Cl | 4-Cl—Ph | H | CH₂ |
| 4-Br | 5-Cl | 4-Cl—Ph | H | CH₂ |
| 4-OCF₂H | 5-Cl | 4-Cl—Ph | H | CH₂ |
| 4-CF₃ | 5-Cl | 4-F—Ph | H | CH₂ |
| 4-Cl | 5-Cl | 4-F—Ph | H | CH₂ |
| 4-Br | 5-Cl | 4-F—Ph | H | CH₂ |
| 4-OCF₂H | 5-Cl | 4-F—Ph | H | CH₂ |
| 4-CF₃ | 5-Cl | 4-NO₂Ph | H | CH₂ |
| 4-Cl | 5-Cl | 4-NO₂Ph | H | CH₂ |
| 4-Br | 5-Cl | 4-NO₂Ph | H | CH₂ |
| 4-OCF₂H | 5-Cl | 4-NO₂Ph | H | CH₂ |
| 4-CF₃ | 5-F | Ph | H | CH₂ |
| 4-Cl | 5-F | Ph | H | CH₂ |
| 4-Br | 5-F | Ph | H | CH₂ |
| 4-OCF₂H | 5-F | Ph | H | CH₂ |
| 4-CF₃ | 5-F | 4-F—Ph | H | CH₂ |
| 4-Cl | 5-F | 4-F—Ph | H | CH₂ |
| 4-Br | 5-F | 4-F—Ph | H | CH₂ |
| 4-OCF₂H | 5-F | 4-F—Ph | H | CH₂ |
| 4-CF₃ | 5-F | 4-Cl—Ph | H | CH₂ |
| 4-Cl | 5-F | 4-Cl—Ph | H | CH₂ |
| 4-Br | 5-F | 4-Cl—Ph | H | CH₂ |
| 4-OCF₂H | 5-F | 4-Cl—Ph | H | CH₂ |
| 4-CF₃ | 5-F | 4-OMe—Ph | H | CH₂ |
| 4-Cl | 5-F | 4-OMe—Ph | H | CH₂ |
| 4-Br | 5-F | 4-OMe—Ph | H | CH₂ |
| 4-OCF₂H | 5-F | 4-OMe—Ph | H | CH₂ |
| 4-CF₃ | 5-Cl | Ph | Me | CH₂ |
| 4-Cl | 5-Cl | Ph | Me | CH₂ |
| 4-Br | 5-Cl | Ph | Me | CH₂ |
| 4-OCF₂H | 5-Cl | Ph | Me | CH₂ |
| 4-CF₃ | 5-Cl | 5-Cl | Me | CH₂ |
| 4-Cl | 5-Cl | 5-Cl | Me | CH₂ |
| 4-Br | 5-Cl | 5-Cl | Me | CH₂ |
| 4-OCF₂H | 5-Cl | 5-Cl | Me | CH₂ |
| 4-CF₃ | 5-F | Ph | Me | CH₂ |
| 4-Cl | 5-F | Ph | Me | CH₂ |
| 4-Br | 5-F | Ph | Me | CH₂ |
| 4-OCF₂H | 5-F | Ph | Me | CH₂ |
| 4-CF₃ | 5-F | 5-Cl | Me | CH₂ |
| 4-Cl | 5-F | 5-Cl | Me | CH₂ |
| 4-Br | 5-F | 5-Cl | Me | CH₂ |
| 4-OCF₂H | 5-F | 5-Cl | Me | CH₂ |
| 4-CF₃ | 5-Cl | CO₂Me | H | CH₂ |
| 4-Cl | 5-Cl | CO₂Me | H | CH₂ |
| 4-Br | 5-Cl | CO₂Me | H | CH₂ |
| 4-OCF₂H | 5-Cl | CO₂Me | H | CH₂ |
| 4-CF₃ | 5-Cl | CO₂Me | Me | CH₂ |
| 4-Cl | 5-Cl | CO₂Me | Me | CH₂ |
| 4-Br | 5-Cl | CO₂Me | Me | CH₂ |
| 4-OCF₂H | 5-Cl | CO₂Me | Me | CH₂ |
| 4-CF₃ | 4-F | CO₂Me | H | CH₂ |
| 4-Cl | 4-F | CO₂Me | H | CH₂ |
| 4-Br | 4-F | CO₂Me | H | CH₂ |
| 4-OCF₂H | 4-F | CO₂Me | H | CH₂ |
| 4-CF₃ | 4-F | CO₂Me | Me | CH₂ |
| 4-Cl | 4-F | CO₂Me | Me | CH₂ |
| 4-Br | 4-F | CO₂Me | Me | CH₂ |
| 4-OCF₂H | 4-F | CO₂Me | Me | CH₂ |
| 4-OCF₃ | 5-Cl | 4-Cl—Ph | H | CH₂ |
| 4-OCF₂CF₂H | 5-Cl | 4-Cl—Ph | H | CH₂ |
| 3-Cl,4-CF₃ | 5-Cl | 4-Cl—Ph | H | CH₂ |
| 3,4-CH₂C(Me)₂O | 5-Cl | 4-Cl—Ph | H | CH₂ |
| 3,4-CF₂CF₂O | 5-Cl | 4-Cl—Ph | H | CH₂ |

TABLE 14-continued

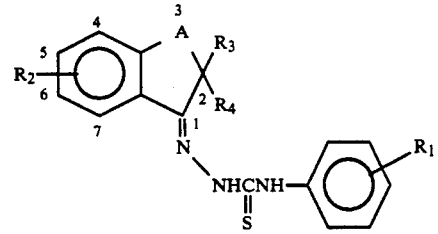

| R₁ | R₂ | R₃ | R₄ | A |
|---|---|---|---|---|
| 4-CN | 5-Cl | 4-Cl—Ph | H | CH₂ |
| 4-NO₂ | 5-Cl | 4-Cl—Ph | H | CH₂ |
| 4-F | 5-Cl | 4-Cl—Ph | H | CH₂ |
| 3,4-di-Cl | 5-Cl | 4-Cl—Ph | H | CH₂ |
| 4-CO₂Me | 5-Cl | 4-Cl—Ph | H | CH₂ |
| 4-SCF₂H | 5-Cl | 4-Cl—Ph | H | CH₂ |
| 4-SCF₂CF₂H | 5-Cl | 4-Cl—Ph | H | CH₂ |
| 4-OCF₂CF₂H | 5-Cl | 4-Cl—Ph | H | CH₂ |
| 4-OCF₃ | 5-Cl | Ph | H | CH₂ |
| 4-OCF₂CF₂H | 5-Cl | Ph | H | CH₂ |
| 3-Cl,4-CF₃ | 5-Cl | Ph | H | CH₂ |
| 3,4-CH₂C(Me)₂O | 5-Cl | Ph | H | CH₂ |
| 3,4-CF₂CF₂O | 5-Cl | Ph | H | CH₂ |
| 4-CN | 5-Cl | Ph | H | CH₂ |
| 4-NO₂ | 5-Cl | Ph | H | CH₂ |
| 4-F | 5-Cl | Ph | H | CH₂ |
| 3,4-di-Cl | 5-Cl | Ph | H | CH₂ |
| 4-CO₂Me | 5-Cl | Ph | H | CH₂ |
| 4-SCF₂H | 5-Cl | Ph | H | CH₂ |
| 4-SCF₂CF₂H | 5-Cl | Ph | H | CH₂ |
| 4-OCH₂CF₃ | 5-Cl | Ph | H | CH₂ |
| 4-CF₃ | 5-Cl | Ph | Me | O |
| 4-Cl | 5-Cl | Ph | Me | O |
| 4-Br | 5-Cl | Ph | Me | O |
| 4-OCF₂H | 5-Cl | Ph | Me | O |
| 4-CF₃ | 5-Cl | 4-Cl—Ph | Me | O |
| 4-Cl | 5-Cl | 4-Cl—Ph | Me | O |
| 4-Br | 5-Cl | 4-Cl—Ph | Me | O |
| 4-OCF₂H | 5-Cl | 4-Cl—Ph | Me | O |
| 4-CF₃ | 5-F | Ph | Me | O |
| 4-Cl | 5-F | Ph | Me | O |
| 4-Br | 5-F | Ph | Me | O |
| 4-OCF₂H | 5-F | Ph | Me | O |
| 4-CF₃ | 5-F | 4-Cl—Ph | Me | O |
| 4-Cl | 5-F | 4-Cl—Ph | Me | O |
| 4-Br | 5-F | 4-Cl—Ph | Me | O |
| 4-OCF₂H | 5-F | 4-Cl—Ph | Me | O |
| 4-CF₃ | 5-F | Me | allyl | O |
| 4-OCF₃ | 5-F | Me | allyl | O |
| 4-CF₃ | 5-Cl | Me | allyl | O |
| 4-OCF₃ | 5-Cl | Me | allyl | O |
| 4-CF₃ | 5-CF₃ | Me | allyl | O |
| 4-OCF₃ | 5-CF₃ | Me | allyl | O |
| 4-CF₃ | 5-F | CH₂Ph | Me | O |
| 4-OCF₃ | 5-F | CH₂Ph | Me | O |
| 4-CF₃ | 5-Cl | CH₂Ph | Me | O |
| 4-OCF₃ | 5-Cl | CH₂Ph | Me | O |
| 4-CF₃ | 5-F | Me | H | O |
| 4-OCF₃ | 5-F | Me | H | O |
| 4-CF₃ | 5-Cl | Me | H | O |
| 4-OCF₃ | 5-Cl | Me | H | O |
| 4-CF₃ | 5-F | i-Pr | H | O |
| 4-OCF₃ | 5-F | i-Pr | H | O |
| 4-CF₃ | 5-Cl | i-Pr | H | O |
| 4-OCF₃ | 5-Cl | i-Pr | H | O |
| 4-CF₃ | 5-Cl | Ph | H | CH₂CH₂ |
| 4-Cl | 5-Cl | Ph | H | CH₂CH₂ |
| 4-Br | 5-Cl | Ph | H | CH₂CH₂ |
| 4-OCF₂H | 5-Cl | Ph | H | CH₂CH₂ |
| 4-CF₃ | 5-Cl | 4-Cl—Ph | H | CH₂CH₂ |
| 4-Cl | 5-Cl | 4-Cl—Ph | H | CH₂CH₂ |
| 4-Br | 5-Cl | 4-Cl—Ph | H | CH₂CH₂ |
| 4-OCF₂H | 5-Cl | 4-Cl—Ph | H | CH₂CH₂ |
| 4-CF₃ | 5-Cl | 4-F—Ph | H | CH₂CH₂ |
| 4-Cl | 5-Cl | 4-F—Ph | H | CH₂CH₂ |
| 4-Br | 5-Cl | 4-F—Ph | H | CH₂CH₂ |
| 4-OCF₂H | 5-Cl | 4-F—Ph | H | CH₂CH₂ |
| 4-CF₃ | 5-Cl | 4-NO₂Ph | H | CH₂CH₂ |
| 4-Cl | 5-Cl | 4-NO₂Ph | H | CH₂CH₂ |

TABLE 14-continued

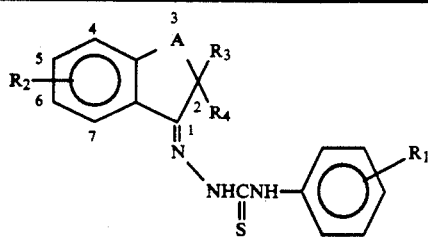

| R₁ | R₂ | R₃ | R₄ | A |
|---|---|---|---|---|
| 4-Br | 5-Cl | 4-NO₂Ph | H | CH₂CH₂ |
| 4-OCF₂H | 5-Cl | 4-NO₂Ph | H | CH₂CH₂ |
| 4-CF₃ | 5-F | Ph | H | CH₂CH₂ |
| 4-Cl | 5-F | Ph | H | CH₂CH₂ |
| 4-Br | 5-F | Ph | H | CH₂CH₂ |
| 4-OCF₂H | 5-F | Ph | H | CH₂CH₂ |
| 4-CF₃ | 5-F | 4-F—Ph | H | CH₂CH₂ |
| 4-Cl | 5-F | 4-F—Ph | H | CH₂CH₂ |
| 4-Br | 5-F | 4-F—Ph | H | CH₂CH₂ |
| 4-OCF₂H | 5-F | 4-F—Ph | H | CH₂CH₂ |
| 4-CF₃ | 5-F | 4-Cl—Ph | H | CH₂CH₂ |
| 4-Cl | 5-F | 4-Cl—Ph | H | CH₂CH₂ |
| 4-Br | 5-F | 4-Cl—Ph | H | CH₂CH₂ |
| 4-OCF₂H | 5-F | 4-Cl—Ph | H | CH₂CH₂ |
| 4-CF₃ | 5-F | 4-OMe | H | CH₂CH₂ |
| 4-Cl | 5-F | 4-OMe | H | CH₂CH₂ |
| 4-Br | 5-F | 4-OMe | H | CH₂CH₂ |
| 4-OCF₂H | 5-F | 4-OMe | H | CH₂CH₂ |
| 4-CF₃ | 5-Cl | Ph | Me | CH₂CH₂ |
| 4-Cl | 5-Cl | Ph | Me | CH₂CH₂ |
| 4-Br | 5-Cl | Ph | Me | CH₂CH₂ |
| 4-OCF₂H | 5-Cl | Ph | Me | CH₂CH₂ |
| 4-CF₃ | 5-Cl | 4-Cl—Ph | Me | CH₂CH₂ |
| 4-Cl | 5-Cl | 4-Cl—Ph | Me | CH₂CH₂ |
| 4-Br | 5-Cl | 4-Cl—Ph | Me | CH₂CH₂ |
| 4-OCF₂H | 5-Cl | 4-Cl—Ph | Me | CH₂CH₂ |
| 4-CF₃ | 5-F | Ph | Me | CH₂CH₂ |
| 4-Cl | 5-F | Ph | Me | CH₂CH₂ |
| 4-Br | 5-F | Ph | Me | CH₂CH₂ |
| 4-OCF₂H | 5-F | Ph | Me | CH₂CH₂ |
| 4-CF₃ | 5-F | 4-Cl—Ph | Me | CH₂CH₂ |
| 4-Cl | 5-F | 4-Cl—Ph | Me | CH₂CH₂ |
| 4-Br | 5-F | 4-Cl—Ph | Me | CH₂CH₂ |
| 4-OCF₂H | 5-F | 4-Cl—Ph | Me | CH₂CH₂ |
| 4-CF₃ | 5-Cl | CO₂Me | H | CH₂CH₂ |
| 4-Cl | 5-Cl | CO₂Me | H | CH₂CH₂ |
| 4-Br | 5-Cl | CO₂Me | H | CH₂CH₂ |
| 4-OCF₂H | 5-Cl | CO₂Me | H | CH₂CH₂ |
| 4-CF₃ | 5-Cl | CO₂Me | Me | CH₂CH₂ |
| 4-Cl | 5-Cl | CO₂Me | Me | CH₂CH₂ |
| 4-Br | 5-Cl | CO₂Me | Me | CH₂CH₂ |
| 4-OCF₂H | 5-Cl | CO₂Me | Me | CH₂CH₂ |
| 4-CF₃ | 4-F | CO₂Me | H | CH₂CH₂ |
| 4-Cl | 4-F | CO₂Me | H | CH₂CH₂ |
| 4-Br | 4-F | CO₂Me | H | CH₂CH₂ |
| 4-OCF₂H | 4-F | CO₂Me | H | CH₂CH₂ |
| 4-CF₃ | 4-F | CO₂Me | Me | CH₂CH₂ |
| 4-Cl | 4-F | CO₂Me | Me | CH₂CH₂ |
| 4-Br | 4-F | CO₂Me | Me | CH₂CH₂ |
| 4-OCF₂H | 4-F | CO₂Me | Me | CH₂CH₂ |
| 4-OCF₃ | 5-Cl | 4-Cl—Ph | H | CH₂CH₂ |
| 4-OCF₂CF₂H | 5-Cl | 4-Cl—Ph | H | CH₂CH₂ |
| 3-Cl,4-CF₃ | 5-Cl | 4-Cl—Ph | H | CH₂CH₂ |
| 3,4-CH₂C(Me)₂O | 5-Cl | 4-Cl—Ph | H | CH₂CH₂ |
| 3,4-CF₂CF₂O | 5-Cl | 4-Cl—Ph | H | CH₂CH₂ |
| 4-CN | 5-Cl | 4-Cl—Ph | H | CH₂CH₂ |
| 4-NO₂ | 5-Cl | 4-Cl—Ph | H | CH₂CH₂ |
| 4-F | 5-Cl | 4-Cl—Ph | H | CH₂CH₂ |
| 3,4-di-Cl | 5-Cl | 4-Cl—Ph | H | CH₂CH₂ |
| 4-CO₂Me | 5-Cl | 4-Cl—Ph | H | CH₂CH₂ |
| 4-SCF₂H | 5-Cl | 4-Cl—Ph | H | CH₂CH₂ |
| 4-SCF₂CF₂H | 5-Cl | 4-Cl—Ph | H | CH₂CH₂ |
| 4-OCH₂CF₃ | 5-Cl | 4-Cl—Ph | H | CH₂CH₂ |
| 4-OCF₃ | 5-Cl | Ph | H | CH₂CH₂ |
| 4-OCF₂CF₂H | 5-Cl | Ph | H | CH₂CH₂ |
| 3-Cl,4-CF₃ | 5-Cl | Ph | H | CH₂CH₂ |
| 3,4-CH₂C(Me)₂O | 5-Cl | Ph | H | CH₂CH₂ |
| 3,4-CF₂CF₂O | 5-Cl | Ph | H | CH₂CH₂ |
| 4-CN | 5-Cl | Ph | H | CH₂CH₂ |
| 4-NO₂ | 5-Cl | Ph | H | CH₂CH₂ |
| 4-F | 5-Cl | Ph | H | CH₂CH₂ |
| 3,4-di-Cl | 5-Cl | Ph | H | CH₂CH₂ |
| 4-CO₂Me | 5-Cl | Ph | H | CH₂CH₂ |
| 4-SCF₂H | 5-Cl | Ph | H | CH₂CH₂ |
| 4-SCF₂CF₂H | 5-Cl | Ph | H | CH₂CH₂ |
| 4-OCH₂CF₃ | 5-Cl | Ph | H | CH₂CH₂ |

TABLE 15

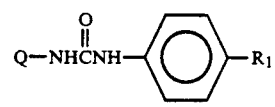

| Q | R₁ | R₂ | R₃ | R₄ | A |
|---|---|---|---|---|---|
| Q-2 | CF₃ | H | H | H | CH₂ |
| Q-2 | OCF₃ | H | H | H | CH₂ |
| Q-2 | CF₃ | H | Me | H | CH₂ |
| Q-2 | OCF₃ | H | Me | H | CH₂ |
| Q-2 | CF₃ | H | 4-F—Ph | H | CH₂ |
| Q-2 | OCF₃ | H | 4-F—Ph | H | CH₂ |
| Q-2 | CF₃ | H | 4-Cl—Ph | H | CH₂ |
| Q-2 | OCF₃ | H | 4-Cl—Ph | H | CH₂ |
| Q-2 | CF₃ | 5-CF₃ | Me | H | CH₂ |
| Q-2 | OCF₃ | 5-CF₃ | Me | H | CH₂ |
| Q-2 | CF₃ | 5-CF₃ | 4-F—Ph | H | CH₂ |
| Q-2 | OCF₃ | 5-CF₃ | 4-F—Ph | H | CH₂ |
| Q-2 | CF₃ | 5-CF₃ | 4-Cl—Ph | H | CH₂ |
| Q-2 | OCF₃ | 5-CF₃ | 4-Cl—Ph | H | CH₂ |
| Q-2 | CF₃ | 5-Cl | Me | H | CH₂ |
| Q-2 | OCF₃ | 5-Cl | Me | H | CH₂ |
| Q-2 | CF₃ | 5-Cl | 4-F—Ph | H | CH₂ |
| Q-2 | OCF₃ | 5-Cl | 4-F—Ph | H | CH₂ |
| Q-2 | CF₃ | H | H | H | O |
| Q-2 | OCF₃ | H | H | H | O |
| Q-2 | CF₃ | H | Me | H | O |
| Q-2 | OCF₃ | H | Me | H | O |
| Q-2 | CF₃ | H | 4-F—Ph | Me | O |
| Q-2 | OCF₃ | H | 4-F—Ph | Me | O |
| Q-2 | CF₃ | H | 4-Cl—Ph | Me | O |
| Q-2 | OCF₃ | H | 4-Cl—Ph | Me | O |
| Q-2 | CF₃ | H | i-Pr | H | O |
| Q-2 | OCF₃ | H | i-Pr | H | O |
| Q-2 | CF₃ | 5-CF₃ | H | H | O |
| Q-2 | OCF₃ | 5-CF₃ | H | H | O |
| Q-2 | CF₃ | 5-CF₃ | Me | H | O |
| Q-2 | OCF₃ | 5-CF₃ | Me | H | O |
| Q-2 | CF₃ | 5-CF₃ | i-Pr | H | O |
| Q-2 | OCF₃ | 5-CF₃ | i-Pr | H | O |
| Q-2 | CF₃ | 5-CF₃ | 4-F—Ph | Me | O |
| Q-2 | OCF₃ | 5-CF₃ | 4-F—Ph | Me | O |
| Q-3 | CF₃ | H | H | H | CH₂ |
| Q-3 | OCF₃ | H | H | H | CH₂ |
| Q-3 | CF₃ | H | Me | H | CH₂ |
| Q-3 | OCF₃ | H | Me | H | CH₂ |
| Q-3 | CF₃ | H | 4-F—Ph | H | CH₂ |
| Q-3 | OCF₃ | H | 4-F—Ph | H | CH₂ |
| Q-3 | CF₃ | H | 4-Cl—Ph | H | CH₂ |
| Q-3 | OCF₃ | H | 4-Cl—Ph | H | CH₂ |
| Q-3 | CF₃ | 4-CF₃ | Me | H | CH₂ |
| Q-3 | OCF₃ | 4-CF₃ | Me | H | CH₂ |
| Q-3 | CF₃ | 4-CF₃ | 4-F—Ph | H | CH₂ |
| Q-3 | OCF₃ | 4-CF₃ | 4-F—Ph | H | CH₂ |
| Q-3 | CF₃ | 4-CF₃ | 4-Cl—Ph | H | CH₂ |
| Q-3 | OCF₃ | 4-CF₃ | 4-Cl—Ph | H | CH₂ |

TABLE 15-continued

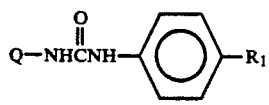

| Q | R₁ | R₂ | R₃ | R₄ | A |
|---|---|---|---|---|---|
| Q-3 | CF₃ | 4-CF₃ | Me | H | CH₂ |
| Q-3 | OCF₃ | 4-CF₃ | Me | H | CH₂ |
| Q-3 | CF₃ | 4-CF₃ | 4-F—Ph | H | CH₂ |
| Q-3 | OCF₃ | 4-CF₃ | 4-F—Ph | H | CH₂ |
| Q-3 | CF₃ | H | H | H | O |
| Q-3 | OCF₃ | H | H | H | O |
| Q-3 | CF₃ | H | Me | H | O |
| Q-3 | OCF₃ | H | Me | H | O |
| Q-3 | CF₃ | H | 4-F—Ph | Me | O |
| Q-3 | OCF₃ | H | 4-F—Ph | Me | O |
| Q-3 | CF₃ | H | 4-Cl—Ph | Me | O |
| Q-3 | OCF₃ | H | 4-Cl—Ph | Me | O |
| Q-3 | CF₃ | H | i-Pr | H | O |
| Q-3 | OCF₃ | H | i-Pr | H | O |
| Q-3 | CF₃ | 4-CF₃ | H | H | O |
| Q-3 | OCF₃ | 4-CF₃ | H | H | O |
| Q-3 | CF₃ | 4-CF₃ | Me | H | O |
| Q-3 | OCF₃ | 4-CF₃ | Me | H | O |
| Q-3 | CF₃ | 4-CF₃ | i-Pr | H | O |
| Q-3 | OCF₃ | 4-CF₃ | i-Pr | H | O |
| Q-3 | CF₃ | 4-CF₃ | 4-F—Ph | Me | O |
| Q-3 | OCF₃ | 4-CF₃ | 4-F—Ph | Me | O |
| Q-4 | CF₃ | H | H | H | CH₂ |
| Q-4 | OCF₃ | H | H | H | CH₂ |
| Q-4 | CF₃ | H | Me | H | CH₂ |
| Q-4 | OCF₃ | H | Me | H | CH₂ |
| Q-4 | CF₃ | H | 4-F—Ph | H | CH₂ |
| Q-4 | OCF₃ | H | 4-F—Ph | H | CH₂ |
| Q-4 | CF₃ | H | 4-Cl—Ph | H | CH₂ |
| Q-4 | OCF₃ | H | 4-Cl—Ph | H | CH₂ |
| Q-4 | CF₃ | 5-CF₃ | Me | H | CH₂ |
| Q-4 | OCF₃ | 5-CF₃ | Me | H | CH₂ |
| Q-4 | CF₃ | 5-CF₃ | 4-F—Ph | H | CH₂ |
| Q-4 | OCF₃ | 5-CF₃ | 4-F—Ph | H | CH₂ |
| Q-4 | CF₃ | 5-CF₃ | 4-Cl—Ph | H | CH₂ |
| Q-4 | OCF₃ | 5-CF₃ | 4-Cl—Ph | H | CH₂ |
| Q-4 | CF₃ | 4-F | Me | H | CH₂ |
| Q-4 | OCF₃ | 4-F | Me | H | CH₂ |
| Q-4 | CF₃ | 4-F | 4-F—Ph | H | CH₂ |
| Q-4 | OCF₃ | 4-F | 4-F—Ph | H | CH₂ |
| Q-4 | CF₃ | H | H | H | O |
| Q-4 | OCF₃ | H | H | H | O |
| Q-4 | CF₃ | H | Me | H | O |
| Q-4 | OCF₃ | H | Me | H | O |
| Q-4 | CF₃ | H | 4-F—Ph | Me | O |
| Q-4 | OCF₃ | H | 4-F—Ph | Me | O |
| Q-4 | CF₃ | H | 4-Cl—Ph | Me | O |
| Q-4 | OCF₃ | H | 4-Cl—Ph | Me | O |
| Q-4 | CF₃ | H | i-Pr | H | O |
| Q-4 | OCF₃ | H | i-Pr | H | O |
| Q-4 | CF₃ | 5-CF₃ | H | H | O |
| Q-4 | OCF₃ | 5-CF₃ | H | H | O |
| Q-4 | CF₃ | 5-CF₃ | Me | H | O |
| Q-4 | OCF₃ | 5-CF₃ | Me | H | O |
| Q-4 | CF₃ | 5-CF₃ | i-Pr | H | O |
| Q-4 | OCF₃ | 5-CF₃ | i-Pr | H | O |
| Q-4 | CF₃ | 5-CF₃ | 4-F—Ph | H | O |
| Q-4 | OCF₃ | 5-CF₃ | 4-F—Ph | H | O |
| Q-5 | CF₃ | H | H | H | CH₂ |
| Q-5 | OCF₃ | H | H | H | CH₂ |
| Q-5 | CF₃ | H | Me | H | CH₂ |
| Q-5 | OCF₃ | H | Me | H | CH₂ |
| Q-5 | CF₃ | H | 4-F—Ph | H | CH₂ |
| Q-5 | OCF₃ | H | 4-F—Ph | H | CH₂ |
| Q-5 | CF₃ | H | 4-Cl—Ph | H | CH₂ |
| Q-5 | OCF₃ | H | 4-Cl—Ph | H | CH₂ |
| Q-5 | CF₃ | 5-CF₃ | Me | H | CH₂ |
| Q-5 | OCF₃ | 5-CF₃ | Me | H | CH₂ |
| Q-5 | CF₃ | 5-CF₃ | 4-F—Ph | H | CH₂ |
| Q-5 | OCF₃ | 5-CF₃ | 4-F—Ph | H | CH₂ |
| Q-5 | CF₃ | 5-CF₃ | 4-Cl—Ph | H | CH₂ |
| Q-5 | OCF₃ | 5-CF₃ | 4-Cl—Ph | H | CH₂ |
| Q-5 | CF₃ | 4-F | Me | H | CH₂ |
| Q-5 | OCF₃ | 4-F | Me | H | CH₂ |
| Q-5 | CF₃ | 4-F | 4-F—Ph | H | CH₂ |

TABLE 15-continued

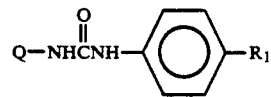

| Q | R₁ | R₂ | R₃ | R₄ | A |
|---|---|---|---|---|---|
| Q-5 | OCF₃ | 4-F | 4-F—Ph | H | CH₂ |
| Q-5 | CF₃ | 5-CF₃ | H | H | O |
| Q-5 | OCF₃ | 5-CF₃ | H | H | O |
| Q-5 | CF₃ | 5-CF₃ | Me | H | O |
| Q-5 | OCF₃ | 5-CF₃ | Me | H | O |
| Q-5 | CF₃ | 5-CF₃ | 4-F—Ph | Me | O |
| Q-5 | OCF₃ | 5-CF₃ | 4-₃F—Ph | Me | O |
| Q-5 | CF₃ | 5-CF₃ | 4-Cl—Ph | Me | O |
| Q-5 | OCF₃ | 5-CF₃ | 4-Cl—Ph | Me | O |
| Q-5 | CF₃ | 5-CF₃ | i-Pr | H | O |
| Q-5 | OCF₃ | 5-CF₃ | i-Pr | H | O |
| Q-5 | CF₃ | 5-Cl | H | H | O |
| Q-5 | OCF₃ | 5-Cl | H | H | O |
| Q-5 | CF₃ | 5-Cl | Me | H | O |
| Q-5 | OCF₃ | 5-Cl | Me | H | O |
| Q-5 | CF₃ | 5-Cl | i-Pr | H | O |
| Q-5 | OCF₃ | 5-Cl | i-Pr | H | O |
| Q-5 | CF₃ | 5-Cl | 4-F—Ph | Me | O |
| Q-5 | OCF₃ | 5-Cl | 4-F—Ph | Me | O |

TABLE 16

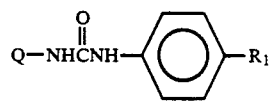

(V = S)

| Q | R₁ | R₂ | R₃ | R₄ | A |
|---|---|---|---|---|---|
| Q-6 | CF₃ | H | H | H | CH₂ |
| Q-6 | OCF₃ | H | H | H | CH₂ |
| Q-6 | CF₃ | H | Me | H | CH₂ |
| Q-6 | OCF₃ | H | Me | H | CH₂ |
| Q-6 | CF₃ | H | 4-F—Ph | H | CH₂ |
| Q-6 | OCF₃ | H | 4-F—Ph | H | CH₂ |
| Q-6 | CF₃ | H | 4-Cl—Ph | H | CH₂ |
| Q-6 | OCF₃ | H | 4-Cl—Ph | H | CH₂ |
| Q-6 | CF₃ | 5-Cl | Me | H | CH₂ |
| Q-6 | OCF₃ | 5-Cl | Me | H | CH₂ |
| Q-6 | CF₃ | 5-Cl | 4-F—Ph | H | CH₂ |
| Q-6 | OCF₃ | 5-Cl | 4-F—Ph | H | CH₂ |
| Q-6 | CF₃ | 5-Cl | 4-Cl—Ph | H | CH₂ |
| Q-6 | OCF₃ | 5-Cl | 4-Cl—Ph | H | CH₂ |
| Q-6 | CF₃ | 5-F | Me | H | CH₂ |
| Q-6 | OCF₃ | 5-F | Me | H | CH₂ |
| Q-6 | CF₃ | 5-F | 4-F—Ph | H | CH₂ |
| Q-6 | OCF₃ | 5-F | 4-F—Ph | H | CH₂ |
| Q-6 | CF₃ | H | H | H | O |
| Q-6 | OCF₃ | H | H | H | O |
| Q-6 | CF₃ | H | Me | H | O |
| Q-6 | OCF₃ | H | Me | H | O |
| Q-6 | CF₃ | H | 4-F—Ph | Me | O |
| Q-6 | OCF₃ | H | 4-₃F—Ph | Me | O |
| Q-6 | CF₃ | H | 4-Cl—Ph | Me | O |
| Q-6 | OCF₃ | H | 4-Cl—Ph | Me | O |
| Q-6 | CF₃ | H | i-Pr | H | O |
| Q-6 | OCF₃ | H | i-Pr | H | O |
| Q-6 | CF₃ | 5-Cl | H | H | O |
| Q-6 | OCF₃ | 5-Cl | H | H | O |
| Q-6 | CF₃ | 5-Cl | Me | H | O |
| Q-6 | OCF₃ | 5-Cl | Me | H | O |
| Q-6 | CF₃ | 5-Cl | i-Pr | H | O |
| Q-6 | OCF₃ | 5-Cl | i-Pr | H | O |
| Q-6 | CF₃ | 5-Cl | 4-F—Ph | Me | O |
| Q-6 | OCF₃ | 5-Cl | 4-F—Ph | Me | O |
| Q-7 | CF₃ | H | H | H | CH₂ |
| Q-7 | OCF₃ | H | H | H | CH₂ |
| Q-7 | CF₃ | H | Me | H | CH₂ |
| Q-7 | OCF₃ | H | Me | H | CH₂ |
| Q-7 | CF₃ | H | 4-F—Ph | H | CH₂ |
| Q-7 | OCF₃ | H | 4-F—Ph | H | CH₂ |

TABLE 16-continued $$Q-NHCNH-\underset{\underset{\parallel}{O}}{}\!\!\!\!\!\!\!\!\!\!-\!\!\bigcirc\!\!-R_1$$

(V = S)

| Q | R₁ | R₂ | R₃ | R₄ | A |
|---|---|---|---|---|---|
| Q-7 | CF₃ | H | 4-Cl—Ph | H | CH₂ |
| Q-7 | OCF₃ | H | 4-Cl—Ph | H | CH₂ |
| Q-7 | CF₃ | 4-Cl | Me | H | CH₂ |
| Q-7 | OCF₃ | 4-Cl | Me | H | CH₂ |
| Q-7 | CF₃ | 4-Cl | 4-F—Ph | H | CH₂ |
| Q-7 | OCF₃ | 4-Cl | 4-F—Ph | H | CH₂ |
| Q-7 | CF₃ | 4-Cl | 4-Cl—Ph | H | CH₂ |
| Q-7 | OCF₃ | 4-Cl | 4-Cl—Ph | H | CH₂ |
| Q-7 | CF₃ | 4-F | Me | H | CH₂ |
| Q-7 | OCF₃ | 4-F | Me | H | CH₂ |
| Q-7 | CF₃ | 4-F | 4-F—Ph | H | CH₂ |
| Q-7 | OCF₃ | 4-F | 4-F—Ph | H | CH₂ |
| Q-7 | CF₃ | H | H | H | O |
| Q-7 | OCF₃ | H | H | H | O |
| Q-7 | CF₃ | H | Me | H | O |
| Q-7 | OCF₃ | H | Me | H | O |
| Q-7 | CF₃ | H | 4-F—Ph | Me | O |
| Q-7 | OCF₃ | H | 4-₃F—Ph | Me | O |
| Q-7 | CF₃ | H | 4-Cl—Ph | Me | O |
| Q-7 | OCF₃ | H | 4-Cl—Ph | Me | O |
| Q-7 | CF₃ | H | i-Pr | H | O |
| Q-7 | OCF₃ | H | i-Pr | H | O |
| Q-7 | CF₃ | 4-F | H | H | O |
| Q-7 | OCF₃ | 4-F | H | H | O |
| Q-7 | CF₃ | 4-F | Me | H | O |
| Q-7 | OCF₃ | 4-F | Me | H | O |
| Q-7 | CF₃ | 4-F | i-Pr | H | O |
| Q-7 | OCF₃ | 4-F | i-Pr | H | O |
| Q-7 | CF₃ | 4-F | 4-F—Ph | Me | O |
| Q-7 | OCF₃ | 4-F | 4-F—Ph | Me | O |
| Q-8 | CF₃ | H | H | H | CH₂ |
| Q-8 | OCF₃ | H | H | H | CH₂ |
| Q-8 | CF₃ | H | Me | H | CH₂ |
| Q-8 | OCF₃ | H | Me | H | CH₂ |
| Q-8 | CF₃ | H | 4-F—Ph | H | CH₂ |
| Q-8 | OCF₃ | H | 4-F—Ph | H | CH₂ |
| Q-8 | CF₃ | H | 4-Cl—Ph | H | CH₂ |
| Q-8 | OCF₃ | H | 4-Cl—Ph | H | CH₂ |
| Q-8 | CF₃ | 4-F | Me | H | CH₂ |
| Q-8 | OCF₃ | 4-F | Me | H | CH₂ |
| Q-8 | CF₃ | 4-F | 4-F—Ph | H | CH₂ |
| Q-8 | OCF₃ | 4-F | 4-F—Ph | H | CH₂ |
| Q-8 | CF₃ | 4-F | 4-Cl—Ph | H | CH₂ |
| Q-8 | OCF₃ | 4-F | 4-Cl—Ph | H | CH₂ |
| Q-8 | CF₃ | 5-Cl | Me | H | CH₂ |
| Q-8 | OCF₃ | 5-Cl | Me | H | CH₂ |
| Q-8 | CF₃ | 5-Cl | 4-F—Ph | H | CH₂ |
| Q-8 | OCF₃ | 5-Cl | 4-F—Ph | H | CH₂ |
| Q-8 | CF₃ | 4-F | H | H | O |
| Q-8 | OCF₃ | 4-F | H | H | O |
| Q-8 | CF₃ | 4-F | Me | H | O |
| Q-8 | OCF₃ | 4-F | Me | H | O |
| Q-8 | CF₃ | 4-F | 4-F—Ph | Me | O |
| Q-8 | OCF₃ | 4-F | 4-₃F—Ph | Me | O |
| Q-8 | CF₃ | 4-F | 4-Cl—Ph | Me | O |
| Q-8 | OCF₃ | 4-F | 4-Cl—Ph | Me | O |
| Q-8 | CF₃ | 4-F | i-Pr | H | O |
| Q-8 | OCF₃ | 4-F | i-Pr | H | O |
| Q-8 | CF₃ | 5-Cl | H | H | O |
| Q-8 | OCF₃ | 5-Cl | H | H | O |
| Q-8 | CF₃ | 5-Cl | Me | H | O |
| Q-8 | OCF₃ | 5-Cl | Me | H | O |
| Q-8 | CF₃ | 5-Cl | i-Pr | H | O |
| Q-8 | OCF₃ | 5-Cl | i-Pr | H | O |
| Q-8 | CF₃ | 5-Cl | 4-F—Ph | Me | O |
| Q-8 | OCF₃ | 5-Cl | 4-F—Ph | Me | O |

ARTHROPODICIDAL FORMULATION AND USE

The compounds of this invention will generally be used in formulation with a carrier comprising a liquid or solid diluent or an organic solvent. Useful formulations of the compounds of Formula I can be prepared in conventional ways. They include dusts, granules, pellets, solutions, suspensions, emulsions, baits, wettable powders, emulsifiable concentrates, dry flowables and the like. Many of these can be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s): and at least one of a) about 0.1% to 20% surfactant(s) and b) about 5% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 25–90 | 0–74 | 1–10 |
| Oil Suspensions, Emulsions, Solutions, (including Emulsifiable Concentrates) | 1–50 | 40–95 | 0–35 |
| Dusts | 1–25 | 70–99 | 0–5 |
| Granules, Baits and Pellets | 0.01–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are Preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, U.S. Pat. No. 3,060,084). Granules and pellets can be made by spraying the active material upon preformed granular carriers or by agglomeration techniques. See Browning, "Agglomeration", *Chemical Engineering*, Dec. 4, 1967, pages 147 and following, and "Perry's Chemical Engineer's Handbook", 4th Ed., McGraw-Hill, New York, 1963, pages 8 to 59 and following.

EXAMPLE A

Emulsifiable Concentrate

| | |
|---|---|
| 2-(5-chloro-2,3-dihydro-2-phenyl-1H-inden-1-ylidene)-N-[4-(trifluoromethyl)phenyl]hydrazinecarboxamide | 20% |
| blend of oil soluble sulfonates and polyoxyethylene ethers | 10% |
| isophorone | 70% |

The ingredients are combined and stirred with gentle warming to speed solution. A fine screen filter is included in packaging operation to insure the absence of any extraneous undissolved material in the product.

EXAMPLE B

Wettable Powder

| | |
|---|---|
| 2-(5-chloro-2,3-dihydro-2-phenyl-1H-inden-1-ylidene)-N-[4-(trifluoromethyl)phenyl]hydrazinecarboxamide | 30% |
| sodium alkylnaphthalenesulfonate | 2% |
| sodium ligninsulfonate | 2% |
| synthetic amorphous silica | 3% |
| kaolinite | 63% |

The active ingredient is mixed with the inert materials in a blender. After grinding in a hammermill, the material is re-blended and sifted through a 50 mesh screen.

EXAMPLE C

Dust

| | |
|---|---|
| Wettable powder of Example B | 10% |
| pyrophyllite (powder) | 90% |

The wettable powder and the pyrophyllite diluent are thoroughly blended and then packaged. The product is suitable for use as a dust.

EXAMPLE D

Granule

| | |
|---|---|
| 2-[5-chloro-2-(4-chlorophenyl)-2,3-dihydro-1H-inden-1-ylidene]-N-[4-(trifluoromethyl)phenyl]hydrazinecarboxamide | 10% |
| attapulgite granules (low volative matter, 0.71/0.30 mm; U.S.S. No. 25-50 sieves) | 90% |

The active ingredient is dissolved in a volatile solvent such as acetone and sprayed upon dedusted and pre-warmed attapulgite granules in a double cone blender. The acetone is then driven off by heating. The granules are then allowed to cool and are packaged.

EXAMPLE E

Granule

| | |
|---|---|
| Wettable powder of Example B | 15% |
| gypsum | 69% |
| potassium sulfate | 16% |

The ingredients are blended in a rotating mixer and water sprayed on to accomplish granulation. When most of the material has reached the desired range of 0.1 to 0.42 mm (U.S.S. No. 18 to 40 sieves), the granules are removed, dried, and screened. Oversize material is crushed to produce additional material in the desired range. These granules contain 4.5% active ingredient.

EXAMPLE F

Solution

| | |
|---|---|
| 2-(5-chloro-2,3-dihydro-2-phenyl-1H-inden-1-ylidene)-N-[4-(trifluoromethyl)phenyl]hydrazinecarboxamide | 25% |
| N-methyl-pyrrolidone | 75% |

The ingredients are combined and stirred to produce a solution suitable for direct, low volume application.

EXAMPLE G

Aqueous Suspension

| | |
|---|---|
| 2-(5-chloro-2,3-dihydro-2-phenyl-1H-inden-1-ylidene)-N-[4-(trifluoromethyl)phenyl]hydrazinecarboxamide | 40% |
| polyacrylic acid thickener | 0.3% |
| dodecyclophenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE H

Oil Suspension

| | |
|---|---|
| 2-[5-chloro-2-(4-chlorophenyl)-2,3-dihydro-1H-inden-1-ylidene]-N-[4-(trifluoromethyl)phenyl]hydrazinecarboxamide | 35.0% |
| blend of polyalcohol carboxylic esters and oil soluble petroleum sulfonates | 6.0% |
| xylene range solvent | 59.0% |

The ingredients are combined and ground together in a sand mill to produce particles essentially all below 5 microns. The product can be used directly, extended with oils, or emulsified in water.

EXAMPLE I

Bait Granules

| | |
|---|---|
| 2-(5-chloro-2,3-dihydro-2-phenyl-1H-inden-1-ylidene)-N-[4-(trifluoromethyl)phenyl]hydrazinecarboxamide | 3.0% |
| blend of polyethoxylated nonylphenols and sodium dodecylbenzene sulfonates | 9.0% |
| ground up corn cobs | 88.0% |

The active ingredient and surfactant blend are dissolved in a suitable solvent such as acetone and sprayed onto the ground corn cobs. The granules are then dried and packaged. Compounds of Formula I can also be mixed with one or more other insecticides, fungicides, nematocides, bactericides, acaricides, or other biologically active compounds to form a multi-component pesticide giving an even broader spectrum of effective agricultural protection. Examples of other agricultural protectants with which compounds of the present invention can be mixed or formulated are:

Insecticides 3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl O-(methylcarbamoyl)thiolacetohydroxamate (methomyl)
N'-(4-chloro-o-tolyl)-N,N-dimethylformamidine (chlordimeform)
O,O-diethyl-O-(2-isopropyl-4-methyl-6-pyrimidylphosphorothioate (diazinon)
octachlorocamphene (toxaphene)
O-ethyl O-p-nitrophenyl phenylphosphonothioate (EPN)
(S)-a-cyano-m-phenoxybenzyl(1R,3R)-3-(2,2-dibromovinyl)-2,2-dimethylcyclopropanecarboxylate (deltamethrin)
Methyl-N ,N -dimethyl-N-[(methylcarbamoyl)oxy]-1-thioox amimidate (oxamyl)
cyano(3-phenoxyphenyl)-methyl-4-chloro-a-(1-methylethyl)benzeneacetate (fenvalerate)
(3-phenoxyphenyl)methyl(+)-cis,trans-3-(2,2-dichloro ethenyl)-2,2-dimethylcyclopropanecarboxylate (permethrin)
a-cyano-3-phenoxybenzyl 3-(2,2-dichlorovinyl)-2,2-dimethylcyclopropane carboxylate (cypermethrin)
O-ethyl-S-(p-chlorophenyl)ethylphosphonodithioate (profenofos)
phosphorothiolothionic acid, O-ethyl-O-[4-(methylthio)-phenyl]-S-n-propyl ester (sulprofos).

Additional insecticides are listed hereafter by their common names: triflumuron, diflubenzuron, methoprene, buprofezin, thiodicarb, acephate, azinphosmethyl, chlorpyrifos, dimethoate, fonophos, isofenphos, methidathion, methamidiphos, monocrotphos, phosmet, phosphamidon, phosalone, pirimicarb, phorate, profenofos, terbufos, trichlorfon, methoxychlor, bifenthrin, biphenate, cyfluthrin, fenpropathrin, fluvalinate, flucythrinate, tralomethrin, metaldehyde and rotenone.

FUNGICIDES methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoly)-2-benzimidazolecarbamate (benomyl)
1-[2-(2,4-dichlorophenyl)-4-propyl-1,3-dioxolan-2-ylmethyl]-1H-1,2,4-triazole (propiconazole)
2-cyano-N-ethylcarbamoy-2-methoxyiminoacetamide (cymoxanil)
1-(4-chlorophenoxy)-3,3-dimethyl-1-(1H-1,2,4-triazol-1-yl)-2-butanone (triadimefon)
N-(trichloromethylthio)tetrahydrophthalimide (captan)
N-(trichloromethylthio)phthalimide (folpet)
1-[[[bis(4-fluorophenyl)][methyl]silyl]methyl]-1H-1,2,4-triazole.

NEMATOCIDES

S-methyl 1-(dimethylcarbamoyl)-N-(methylcarbamoyloxy)thioformimidate
S-methyl 1-carbamoyl-N-(methylcarbamoyloxy)thioformimidate
N-isopropylphosphoramidic acid, O-ethyl O'-[4-(methylthio)-m-tolyl]diester (fenamiphos)

BACTERICIDES tribasic copper sulfate
streptomycin sulfate

ACARICIDES senecioic acid, ester with 2-sec-butyl-4,6-dinitrophenol (binapacryl)
6-methyl-1,3-cithiolo[4,5-α]quinoxalin-2-one (oxythioquinox)
ethyl 4,4'-dichlorobenzilate (chlorobenzilate)
1,1-bis(P-chlorophenyl)-2,2,2-trichloroethanol (dicofol)
bis(pentachloro-2,4-cyclopentadien-1-yl) (dienochlor)
tricyclohexyltin hydroxide (cyhexatin)
trans-5-(4-chlorophenyl)-N-cyclohexyl-4-methyl-2-oxothiazolidine-3-carboxamide (hexythiazox)
amitraz
propargite
fenbutatin-oxide

BIOLOGICAL

*Bacillus thuringiensis*
*Avermectin B.*

UTILITY

The compounds of this invention exhibit activity against a wide spectrum of foliar and soil inhabiting arthropods which are pests of growing and stored agronomic crops, forestry, greenhouse crops, ornamentals, nursery crops, stored food and fiber products, livestock, household, and public and animal health. Those skilled in the art will recognize that not all compounds are equally effective against all pests but the compounds of this invention display activity against economically important agronomic, forestry, greenhouse, ornamental food and fiber product, stored product, and nursery pests, such as:

larvae of the order Lepidoptera including fall and beet armyworm and other Spodoptera spp., tobacco budworm, corn earworm and other Heliothis spp., European corn borer, navel orangeworm, stalk/stem borers and other pyralids, cabbage and soybean loopers and other loopers, codling moth, grape berry moth and other tortricids, black cutworm, spotted cutworm, other cutworms and other noctuids, diamondback moth, green cloverworm, velvetbean caterpillar, green cloverworm, pink bollworm, gypsy moth, and spruce budworm;

foliar feeding larvae and adults of the order Coleoptera including Colorado potato beetle, Mexican bean beetle, flea beetle, Japanese beetles, and other leaf beetles, boll weevil, rice water weevil, granary weevil, rice weevil and other weevil pests, and soil inhabiting insects such as Western corn rootworm and other Diabrotica spp., Japanese beetle, European chafer and other coleopteran grubs, and wireworms;

adults and larvae of the orders Hemiptera and Homoptera including tarnished plant bug and other plant bugs (miridae), aster leafhopper and other leafhoppers (cicadellidae), rice planthopper, brown planthopper, and other planthoppers (fulgoroidea), psylids, whiteflies (aleurodidae), aphids (aphidae), scales (coccidae and diaspididae), lace bugs (tingidae), stink bugs (pentatomidae), cinch bugs and other seed bugs (lygaeidae), cicadas (cicadidae), spittlebugs (cercopids), squash bugs (coreidae), red bugs and cotton stainers (pyrrhocoridae);

adults and larvae of the order acari (mites) including European red mite, two spotted spider mite, rust mites, McDaniel mite, and foliar feeding mites;

adults and immatures of the order Orthoptera including grasshoppers;

adults and immatures of the order Diptera including leafminers, midges, fruit flies (tephritidae), and soil maggots;

adults and immatures of the order Thysanoptera including onion thrips and other foliar feeding thrips.

The compounds are also active against economically important livestock, household, public and animal health pests such as:

insect pests of the order Hymenoptera including carpenter ants, bees, hornets, and wasps;

insect pests of the order Diptera including house files, stable flies, face flies, horn flies, blow flies, and other muscoid fly pests, horse flies, deer flies and other Brachycera, mosquitoes, black flies, biting midges, sand flies, sciarids, and other Nematocera;

insect pests of the order Orthoptera including cockroaches and crickets;

insect pests of the order Isoptera including the Eastern subterranean termite and other termites;

insect pests of the order Mallophaga and Anoplura including the head louse, body louse, chicken head louse and other sucking and chewing parasitic lice that attack man and animals;

insect pests of the order Siphonoptera including the cat flea, dog flea and other fleas.

The specific species for which control is exemplified are: fall armyworm, *Spodoptera fruigiperda*: tobacco budworm, *Heliothis virescens*; boll weevil, *Anthonomus grandis*: aster leafhopper, *Macrosteles fascifrons;* southern corn rootworm, *Diabrotica undecimpunctata*. The pest control protection afforded by these compounds of the present invention is not limited, however to these species.

APPLICATION

Arthropod pests are controlled and protection of agronomic crops, animal and human health is achieved by applying one or more of the Formula I compounds of this invention, in an effective amount, to the locus of infestation, to the area to be protected, or directly on the pests to be controlled. Because of the diversity of habitat and behavior of these arthropod pest species, many different methods of application are employed. A preferred method of application is by spraying with equipment that distributes the compound in the environment of the pests, on the foliage, animal, person, or premise, in the soil or animal, to the plant part that is infested or needs to be protected. Alternatively, granular formulations of these toxicant compounds can be applied to or incorporated into the soil.

Other methods of application can also be employed including direct and residual sprays, aerial, baits, eartags, boluses, foggers, aerosols, and many others. The compounds can be incorporated into baits that are consumed by the arthropods or in devices such as traps and the like which entice them to ingest or otherwise contact the compounds.

The compounds of this invention can be applied in their pure state, but most often application will be of a formulation comprising one or more compounds with suitable carriers, diluents, and surfactants and Possibly in combination with a food depending on the contemplated end use. A preferred method of application involves spraying a water dispersion or refined oil solution of the compounds. Combinations with spray oils, spray oil concentrations, and synergists such as piperonyl butoxide often enhance the efficacy of the compounds of Formula I.

The rate of application of the Formula I compounds required for effective control will depend on such factors as the species of arthropod to be controlled, the pest's life cycle, life stage, its size, location, time of year, host crop or animal, feeding behavior, mating behavior, ambient moisture, temperature, etc. In general, application rates of 0.05 to 2 kg of active ingredient per hectare are sufficient to provide large-scale effective control of pests in agronomic ecosystems under normal circumstances, but as little as 0.001 kg/hectare or as 1 much as 8 kg hectare may be required. For nonagronomic applications, effective use rates will range from about 0.1 to 5 mg/square foot but as little as about 0.01 mg/square foot or as much as 15 mg/square foot may be required.

The following Examples demonstrate the control efficacy of compounds of Formula I on specific pests; see Tables 1 to 10 for compound descriptions. Compounds followed by a dash in the percent mortality column were either not screened or had less than 80% mortality on the test species.

EXAMPLE 8

Fall Armyworm

Test units, each consisting of an 8-ounce plastic cup containing a layer of wheat germ diet, approximately 0.5 cm thick, were Prepared. Ten third-instar larvae of fall armyworm (*Spodoptera frigiperda*) were placed into each cup. Solutions of each of the test compounds (acetone/distilled water 75/25 solvent) were sprayed onto the cups, a single solution per set of three cups. Spraying was accomplished by passing the cups, on a conveyer belt, directly beneath a flat fan hydraulic nozzle which discharged the spray at a rate of 0.5 pounds of active ingredient per acre (about 0.55 kg/ha) at 30 p.s.i. The cups were then covered and held at 27° C. and 50% relative humidity for 72 hours, after which time readings were taken. The results are tabulated below.

| Compound | % Mort. |
| --- | --- |
| 1 | 100 |
| 2 | 100 |
| 3 | 100 |
| 4 | 100 |
| 5 | 100 |
| 6 | — |
| 7 | 100 |
| 8 | 100 |
| 9 | 100 |
| 10 | 100 |

-continued

| Compound | % Mort. |
|---|---|
| 11 | 100 |
| 12 | 100 |
| 13 | 100 |
| 14 | 100 |
| 15 | 100 |
| 16 | 100 |
| 17 | 100 |
| 18 | 67 |
| 19 | 60 |
| 20 | 47 |
| 21 | 100 |
| 22 | 87 |
| 23 | 100 |
| 24 | 87 |
| 25 | 100 |
| 26 | 100 |
| 27 | 100 |
| 28 | — |
| 29 | 100 |
| 30 | 100 |
| 31 | — |
| 32 | — |
| 33 | — |
| 34 | 100 |
| 35 | — |
| 36 | 100 |
| 37 | 100 |
| 38 | 100 |
| 39 | 87 |
| 40 | 93 |
| 41 | 73 |
| 42 | 100 |
| 43 | 100 |
| 44 | 100 |
| 45 | 100 |
| 46 | 100 |
| 47 | 100 |
| 48 | 87 |
| 49 | 80 |
| 50 | 80 |
| 51 | 100 |
| 52 | — |
| 53 | — |
| 54 | 100 |
| 55 | 100 |
| 56 | — |
| 57 | 80 |
| 58 | — |
| 59 | 80 |
| 60 | 47 |
| 61 | 100 |
| 62 | 100 |
| 63 | 60 |
| 64 | — |
| 65 | — |
| 66 | 100 |
| 67 | 100 |
| 68 | 100 |
| 69 | 100 |
| 70 | — |
| 71 | 40 |
| 72 | 100 |
| 73 | 93 |
| 74 | 27 |
| 75 | 20 |
| 76 | — |
| 77 | 100 |
| 78 | 20 |
| 79 | 40 |
| 80 | — |
| 81 | 87 |
| 82 | 33 |
| 83 | 80 |
| 84 | 60 |
| 85 | 80 |
| 86 | — |
| 87 | — |
| 88 | 73 |
| 89 | — |
| 90[1] | 100 |
| 91 | 100 |

-continued

| Compound | % Mort. |
|---|---|
| 92 | 100 |
| 93 | 100 |
| 94 | 100 |
| 95 | 93 |
| 96 | — |
| 97 | — |
| 98 | 100 |
| 99 | 93 |
| 100 | 60 |
| 101 | — |
| 102 | — |
| 103 | — |
| 104 | 100 |
| 105 | 100 |
| 106 | 100 |
| 107 | 100 |
| 108 | 100 |
| 109 | — |
| 110 | 100 |
| 111 | 100 |
| 112 | 100 |
| 113 | 33 |
| 114 | — |
| 115 | — |
| 116 | — |
| 117 | — |
| 118 | — |
| 119 | — |
| 120 | — |
| 121 | 60 |
| 122 | — |
| 123 | — |
| 124 | — |
| 125 | — |
| 126 | — |
| 127 | — |
| 128 | — |
| 129 | — |
| 130 | — |
| 131 | — |
| 132 | — |
| 133 | — |
| 134 | 33 |
| 135 | — |
| 136 | — |
| 137 | — |
| 138 | 33 |
| 139 | — |
| 140 | — |
| 141 | — |
| 142 | 33 |
| 143 | 100 |
| 144 | 60 |
| 145 | — |
| 146 | — |
| 147 | — |
| 148 | — |
| 149 | 13 |
| 150 | — |
| 151 | — |
| 152 | — |
| 153 | — |
| 154 | — |
| 155 | — |
| 156 | — |
| 157 | — |
| 158 | — |
| 159 | — |
| 160 | 20 |
| 161 | — |
| 162 | — |
| 163 | — |
| 164 | — |
| 165 | 0 |
| 166 | 0 |
| 167 | — |
| 168 | 47 |
| 169 | — |
| 170 | 20 |
| 171 | — |
| 172 | — |

| Compound | % Mort. |
|---|---|
| 173 | — |
| 174 | — |
| 175 | — |
| 176 | 67 |
| 177 | 87 |
| 178 | 33 |
| 179 | — |
| 180 | — |
| 181 | 100 |
| 182 | — |
| 183 | — |
| 184 | — |
| 185 | — |
| 186 | — |
| 187 | — |
| 188 | — |
| 189 | 100 |
| 190 | 93 |
| 191 | 20 |
| 192 | — |
| 193 | 60 |
| 194 | — |
| 195 | — |
| 196 | — |
| 197 | — |
| 198 | — |
| 199 | — |
| 200 | — |
| 201 | — |
| 202 | 100 |
| 203 | — |
| 204 | 100 |
| 205 | 67 |
| 206 | 100 |
| 207 | — |
| 208 | — |
| 209 | 40 |
| 210 | — |
| 211 | — |
| 212 | 100 |
| 213 | — |
| 214 | — |
| 215 | — |
| 216 | 73 |
| 217 | — |
| 218 | — |
| 219 | — |
| 220 | 60 |
| 221 | — |
| 222 | 100 |
| 223 | — |
| 224 | 47 |
| 225 | — |
| 226 | — |
| 227 | 73 |
| 228 | — |
| 229 | — |
| 230 | — |
| 231 | — |
| 232 | — |
| 233 | — |
| 234 | 47 |
| 235 | — |
| 236 | — |
| 237 | 87 |
| 238 | 53 |
| 239 | — |
| 240 | 93 |
| 241 | 100 |
| 242 | 100 |
| 243 | 13 |
| 244 | — |
| 245 | 67 |
| 246 | — |
| 247 | — |
| 248 | — |
| 249 | — |
| 250 | 40 |
| 251 | 40 |
| 252 | 67 |
| 253 | 87 |
| 254 | 100 |
| 255 | 30 |
| 256 | — |
| 257 | — |
| 258 | 60 |
| 259 | — |
| 260 | — |
| 261 | — |
| 262 | — |
| 263 | — |
| 265 | — |
| 266 | — |
| 267 | — |
| 268 | — |
| 269 | — |

[1]Test procedure was identical to that described except there was only one test cup.

EXAMPLE 9

Tobacco Budworm

The test procedure of Example 8 was repeated for efficacy against third-instar larvae of the tobacco budworm (*Heliothis virescens*) except that mortality was assessed at 48 hours. The results are tabulated below.

| Compound | % Mort. |
|---|---|
| 1 | 100 |
| 2 | 100 |
| 3 | 73 |
| 4 | 100 |
| 5 | 93 |
| 6 | — |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 40 |
| 20 | 67 |
| 21 | 100 |
| 22 | — |
| 23 | — |
| 24 | 13 |
| 25 | 100 |
| 26 | 100 |
| 27 | 100 |
| 28 | 47 |
| 29 | 87 |
| 30 | 73 |
| 31 | — |
| 32 | — |
| 33 | — |
| 34 | — |
| 35 | 0 |
| 36 | 93 |
| 37 | 100 |
| 38 | 100 |
| 39 | 73 |
| 40 | 100 |
| 41 | 73 |
| 42 | 100 |
| 43 | 87 |
| 44 | 100 |
| 45 | 100 |
| 46 | 100 |
| 47 | 73 |
| 48 | 33 |
| 49 | — |
| 50 | 60 |

-continued

| Compound | % Mort. |
|---|---|
| 51 | — |
| 52 | — |
| 53 | — |
| 54 | 100 |
| 55 | 100 |
| 56 | — |
| 57 | — |
| 58 | — |
| 59 | 100 |
| 60 | — |
| 61 | 40 |
| 62 | — |
| 63 | 0 |
| 64 | — |
| 65 | — |
| 66 | 100 |
| 67 | 100 |
| 68 | 87 |
| 69 | 100 |
| 70 | 93 |
| 71 | — |
| 72 | 100 |
| 73 | 60 |
| 74 | — |
| 75 | — |
| 76 | — |
| 77 | 100 |
| 78 | 20 |
| 79 | — |
| 80 | — |
| 81 | — |
| 82 | — |
| 83 | — |
| 84 | — |
| 85 | — |
| 86 | — |
| 87 | — |
| 88 | 60 |
| 89 | — |
| 90[1] | — |
| 91 | 100 |
| 92 | 100 |
| 93 | 100 |
| 94 | 87 |
| 95 | 80 |
| 96 | — |
| 97 | — |
| 98 | 100 |
| 99 | — |
| 100 | — |
| 101 | — |
| 102 | — |
| 103 | 87 |
| 104 | 33 |
| 105 | 100 |
| 106 | 100 |
| 107 | 100 |
| 108 | — |
| 109 | — |
| 110 | 67 |
| 111 | — |
| 112 | — |
| 113 | — |
| 114 | — |
| 115 | — |
| 116 | — |
| 117 | — |
| 118 | — |
| 119 | — |
| 120 | — |
| 121 | — |
| 122 | — |
| 123 | — |
| 124 | — |
| 125 | — |
| 126 | — |
| 127 | — |
| 128 | — |
| 129 | — |
| 130 | — |
| 131 | — |

-continued

| Compound | % Mort. |
|---|---|
| 132 | 0 |
| 133 | — |
| 134 | — |
| 135 | — |
| 136 | — |
| 137 | — |
| 138 | 67 |
| 139 | — |
| 140 | 27 |
| 141 | — |
| 142 | 20 |
| 143 | 100 |
| 144 | 80 |
| 145 | — |
| 146 | — |
| 147 | — |
| 148 | — |
| 149 | — |
| 150 | — |
| 151 | — |
| 152 | — |
| 153 | — |
| 154 | — |
| 155 | — |
| 156 | — |
| 157 | — |
| 158 | — |
| 159 | — |
| 160 | — |
| 161 | — |
| 162 | — |
| 163 | — |
| 164 | — |
| 165 | 80 |
| 166 | 73 |
| 167 | 40 |
| 168 | — |
| 169 | — |
| 170 | 47 |
| 171 | — |
| 172 | 27 |
| 173 | — |
| 174 | — |
| 175 | — |
| 176 | 80 |
| 177 | 20 |
| 178 | — |
| 179 | 73 |
| 180 | — |
| 181 | 53 |
| 182 | — |
| 183 | — |
| 184 | — |
| 185 | — |
| 186 | — |
| 187 | — |
| 188 | — |
| 189 | — |
| 190 | 53 |
| 191 | — |
| 192 | — |
| 193 | — |
| 194 | 13 |
| 195 | — |
| 196 | — |
| 197 | — |
| 198 | — |
| 199 | — |
| 200 | — |
| 201 | — |
| 202 | 100 |
| 203 | — |
| 204 | 67 |
| 205 | 67 |
| 206 | 100 |
| 207 | 33 |
| 208 | — |
| 209 | 60 |
| 210 | — |
| 211 | — |
| 212 | — |

-continued

| Compound | % Mort. |
|---|---|
| 213 | — |
| 214 | — |
| 215 | — |
| 216 | 20 |
| 217 | 13 |
| 218 | — |
| 219 | — |
| 220 | — |
| 221 | — |
| 222 | — |
| 223 | — |
| 224 | — |
| 225 | — |
| 226 | — |
| 227 | — |
| 228 | — |
| 229 | — |
| 230 | — |
| 231 | — |
| 232 | — |
| 233 | — |
| 234 | — |
| 235 | — |
| 236 | 80 |
| 237 | — |
| 238 | 60 |
| 239 | 80 |
| 240 | — |
| 241 | 70 |
| 242 | 93 |
| 243 | 7 |
| 244 | — |
| 245 | — |
| 246 | — |
| 247 | — |
| 248 | — |
| 249 | — |
| 250 | — |
| 251 | — |
| 252 | 87 |
| 253 | 53 |
| 254 | — |
| 255 | 7 |
| 256 | 33 |
| 257 | 47 |
| 258 | 33 |
| 259 | — |
| 260 | — |
| 261 | — |
| 262 | — |
| 263 | — |
| 264 | — |
| 265 | — |
| 266 | — |
| 267 | — |
| 268 | — |
| 269 | — |

EXAMPLE 10

Aster Leafhopper

Test units were prepared from a series of 12-ounce cups, each containing oat (*Avena sativa*) seedlings in a 1-inch layer of sterilized soil. The test units were sprayed with individual solutions of the below-listed compounds. After the oats had dried from being sprayed, between 10 and 15 adult aster leafhoppers (*Mascrosteles fascifrons*) were aspirated into each of the covered cups. The cups were held at 27° C. and 50% relative humidity for 48 hours, after which time mortality readings were taken. The following table depicts the activity of the compounds tested on aster leafhopper.

| Compound | % Mort. |
|---|---|
| 1 | — |
| 2 | — |
| 3 | — |
| 4 | 6 |
| 5 | — |
| 6 | — |
| 7 | 44 |
| 8 | — |
| 9 | 100 |
| 10 | 85 |
| 11 | — |
| 12 | 95 |
| 13 | 83 |
| 14 | — |
| 15 | 73 |
| 16 | 75 |
| 17 | — |
| 18 | 100 |
| 19 | 100 |
| 20 | 100 |
| 21 | — |
| 22 | — |
| 23 | — |
| 24 | — |
| 25 | — |
| 26 | — |
| 27 | — |
| 28 | — |
| 29 | — |
| 30 | — |
| 31 | — |
| 32 | — |
| 33 | — |
| 34 | — |
| 35 | — |
| 36 | — |
| 37 | 91 |
| 38 | — |
| 39 | — |
| 40 | — |
| 41 | 60 |
| 42 | 98 |
| 43 | 89 |
| 44 | — |
| 45 | 100 |
| 46 | — |
| 47 | 100 |
| 48 | — |
| 49 | — |
| 50 | — |
| 51 | — |
| 52 | — |
| 53 | — |
| 54 | — |
| 55 | — |
| 56 | — |
| 57 | — |
| 58 | — |
| 59 | — |
| 60 | 12 |
| 61 | 96 |
| 62 | — |
| 63 | — |
| 64 | — |
| 65 | — |
| 66 | 50 |
| 67 | — |
| 68 | 72 |
| 69 | 88 |
| 70 | 84 |
| 71 | — |
| 72 | — |
| 73 | — |
| 74 | — |
| 75 | — |
| 76 | — |
| 77 | 100 |
| 78 | 83 |
| 79 | 71 |
| 80 | — |
| 81 | 100 |

-continued

| Compound | % Mort. |
|---|---|
| 82 | — |
| 83 | 82 |
| 84 | — |
| 85 | — |
| 86 | — |
| 87 | — |
| 88 | 91 |
| 89 | — |
| 90[1] | — |
| 91 | — |
| 92 | 77 |
| 93 | 94 |
| 94 | — |
| 95 | 74 |
| 96 | — |
| 97 | — |
| 98 | — |
| 99 | 100 |
| 100 | — |
| 101 | — |
| 102 | — |
| 103 | — |
| 104 | — |
| 105 | 100 |
| 106 | 84 |
| 107 | 100 |
| 108 | 71 |
| 109 | — |
| 110 | — |
| 111 | — |
| 112 | — |
| 113 | — |
| 114 | — |
| 115 | — |
| 116 | — |
| 117 | — |
| 118 | — |
| 119 | — |
| 120 | — |
| 121 | — |
| 122 | — |
| 123 | — |
| 124 | — |
| 125 | — |
| 126 | — |
| 127 | — |
| 128 | — |
| 129 | — |
| 130 | — |
| 131 | — |
| 132 | — |
| 133 | — |
| 134 | — |
| 135 | — |
| 136 | — |
| 137 | — |
| 138 | 92 |
| 139 | — |
| 140 | — |
| 141 | — |
| 142 | — |
| 143 | — |
| 144 | — |
| 145 | — |
| 146 | — |
| 147 | — |
| 148 | — |
| 149 | — |
| 150 | — |
| 151 | — |
| 152 | — |
| 153 | — |
| 154 | — |
| 155 | — |
| 156 | — |
| 157 | — |
| 158 | — |
| 159 | — |
| 160 | — |
| 161 | — |
| 162 | — |

-continued

| Compound | % Mort. |
|---|---|
| 163 | — |
| 164 | — |
| 165 | 36 |
| 166 | — |
| 167 | — |
| 168 | — |
| 169 | — |
| 170 | — |
| 171 | — |
| 172 | — |
| 173 | — |
| 174 | — |
| 175 | — |
| 176 | 91 |
| 177 | 93 |
| 178 | 60 |
| 179 | — |
| 180 | — |
| 181 | 98 |
| 182 | 68 |
| 183 | — |
| 184 | — |
| 185 | — |
| 186 | — |
| 187 | — |
| 188 | — |
| 189 | 81 |
| 190 | 70 |
| 191 | — |
| 192 | 95 |
| 193 | — |
| 194 | — |
| 195 | — |
| 196 | — |
| 197 | — |
| 198 | — |
| 199 | — |
| 200 | — |
| 201 | — |
| 202 | 100 |
| 203 | — |
| 204 | 94 |
| 205 | — |
| 206 | 66 |
| 207 | 57 |
| 208 | — |
| 209 | — |
| 210 | 90 |
| 211 | — |
| 212 | 88 |
| 213 | — |
| 214 | — |
| 215 | — |
| 216 | — |
| 217 | — |
| 218 | — |
| 219 | — |
| 220 | — |
| 221 | — |
| 222 | — |
| 223 | — |
| 224 | — |
| 225 | — |
| 226 | — |
| 227 | — |
| 228 | — |
| 229 | — |
| 230 | — |
| 231 | — |
| 232 | — |
| 233 | — |
| 234 | 92 |
| 235 | 100 |
| 236 | 91 |
| 237 | 98 |
| 238 | 98 |
| 239 | 98 |
| 240 | 100 |
| 241 | 97 |
| 242 | — |
| 243 | — |

-continued

| Compound | % Mort. |
|---|---|
| 244 | — |
| 245 | — |
| 246 | — |
| 247 | — |
| 248 | — |
| 249 | — |
| 250 | — |
| 251 | — |
| 252 | — |
| 253 | — |
| 254 | — |
| 255 | — |
| 256 | — |
| 257 | — |
| 258 | 62 |
| 259 | — |
| 260 | — |
| 261 | — |
| 262 | — |
| 263 | — |
| 264 | — |
| 265 | — |
| 266 | — |
| 267 | — |
| 268 | — |
| 269 | — |

EXAMPLE 11

Southern Corn Rootworm

Test units, each consisting of an 8-ounce plastic cup containing 1 sprouted corn seed, were prepared. Sets of three tests units were sprayed as described in Example 8 with individual solutions of the below-listed compounds. After the spray on the cups had dried, five third-instar larvae of the southern corn rootworm (*Diabrotica undecimpunctata howardi*) were placed into each cup. A moistened dental wick was inserted into each cup to prevent drying and the cups were then covered. The cups were then held at 27° C. and 50% relative humidity for 48 hours, after which time mortality readings were taken. The results are tabulated below.

| Compound | % Mort. |
|---|---|
| 1 | 100 |
| 2 | 100 |
| 3 | 100 |
| 4 | 100 |
| 5 | 100 |
| 6 | — |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 22 | — |
| 23 | 100 |
| 24 | 93 |
| 25 | — |
| 26 | 87 |
| 27 | — |
| 28 | — |
| 29 | — |
| 30 | 87 |
| 31 | 100 |
| 32 | — |
| 33 | — |
| 34 | 100 |
| 35 | — |
| 36 | 100 |
| 37 | 100 |
| 38 | 100 |
| 39 | 100 |
| 40 | 80 |
| 41 | 100 |
| 42 | 100 |
| 43 | 100 |
| 44 | 100 |
| 45 | — |
| 46 | 100 |
| 47 | — |
| 48 | — |
| 49 | — |
| 50 | 47 |
| 51 | 100 |
| 52 | — |
| 53 | — |
| 54 | 100 |
| 55 | 100 |
| 56 | — |
| 57 | — |
| 58 | 30 |
| 59 | 100 |
| 60 | 80 |
| 61 | 100 |
| 62 | 100 |
| 63 | 80 |
| 64 | 100 |
| 65 | — |
| 66 | 100 |
| 67 | 100 |
| 68 | 100 |
| 69 | 100 |
| 70 | 100 |
| 71 | 47 |
| 72 | 73 |
| 73 | — |
| 74 | 100 |
| 75 | 67 |
| 76 | 67 |
| 77 | 100 |
| 78 | — |
| 79 | 100 |
| 80 | — |
| 81 | 100 |
| 82 | 100 |
| 83 | 100 |
| 84 | — |
| 85 | — |
| 86 | — |
| 87 | 93 |
| 88 | 100 |
| 89 | 100 |
| 90[1] | — |
| 91 | 100 |
| 92 | 100 |
| 93 | 100 |
| 94 | 100 |
| 95 | 100 |
| 96 | 100 |
| 97 | 100 |
| 98 | 100 |
| 99 | 100 |
| 100 | 100 |
| 101 | 100 |
| 102 | 40 |
| 103 | — |
| 104 | — |
| 105 | 100 |
| 106 | 67 |
| 107 | 100 |
| 108 | 100 |
| 109 | — |
| 110 | 100 |
| 111 | 100 |

-continued

| Compound | % Mort. |
|---|---|
| 112 | 100 |
| 113 | — |
| 114 | — |
| 115 | — |
| 116 | — |
| 117 | — |
| 118 | — |
| 119 | — |
| 120 | — |
| 121 | — |
| 122 | — |
| 123 | — |
| 124 | — |
| 125 | — |
| 126 | — |
| 127 | — |
| 128 | — |
| 129 | — |
| 130 | 60 |
| 131 | — |
| 132 | — |
| 133 | 47 |
| 134 | 100 |
| 135 | — |
| 136 | 100 |
| 137 | 100 |
| 138 | 100 |
| 139 | 100 |
| 140 | 93 |
| 141 | 100 |
| 142 | — |
| 143 | 100 |
| 144 | 100 |
| 145 | 87 |
| 146 | — |
| 147 | 100 |
| 148 | 47 |
| 149 | — |
| 150 | — |
| 151 | — |
| 152 | 100 |
| 153 | — |
| 154 | — |
| 155 | — |
| 156 | — |
| 157 | — |
| 158 | — |
| 159 | — |
| 160 | 0 |
| 161 | — |
| 162 | — |
| 163 | — |
| 164 | 93 |
| 165 | 100 |
| 166 | 87 |
| 167 | — |
| 168 | 100 |
| 169 | 100 |
| 170 | 100 |
| 171 | — |
| 172 | 93 |
| 173 | 100 |
| 174 | — |
| 175 | — |
| 176 | 100 |
| 177 | 100 |
| 178 | 100 |
| 179 | 100 |
| 180 | 100 |
| 181 | 100 |
| 182 | 100 |
| 183 | 60 |
| 184 | — |
| 185 | 100 |
| 186 | 100 |
| 187 | — |
| 188 | — |
| 189 | 100 |
| 190 | 100 |
| 191 | 100 |
| 192 | 100 |

-continued

| Compound | % Mort. |
|---|---|
| 193 | 100 |
| 194 | 100 |
| 195 | — |
| 196 | — |
| 197 | — |
| 198 | — |
| 199 | — |
| 200 | — |
| 201 | — |
| 202 | 100 |
| 203 | — |
| 204 | 100 |
| 205 | 100 |
| 206 | 100 |
| 207 | 93 |
| 208 | 100 |
| 209 | 100 |
| 210 | 100 |
| 211 | 100 |
| 212 | 100 |
| 213 | — |
| 214 | — |
| 215 | — |
| 216 | — |
| 217 | — |
| 218 | — |
| 219 | — |
| 220 | — |
| 221 | — |
| 222 | — |
| 223 | — |
| 224 | 100 |
| 225 | — |
| 226 | — |
| 227 | 100 |
| 228 | 13 |
| 229 | — |
| 230 | — |
| 231 | — |
| 232 | — |
| 233 | — |
| 234 | 100 |
| 235 | 100 |
| 236 | 100 |
| 237 | 100 |
| 238 | 100 |
| 239 | 100 |
| 240 | 100 |
| 241 | 100 |
| 242 | 100 |
| 243 | — |
| 244 | — |
| 245 | 27 |
| 246 | — |
| 247 | — |
| 248 | — |
| 249 | — |
| 250 | — |
| 251 | — |
| 252 | 100 |
| 253 | 100 |
| 254 | 80 |
| 255 | 100 |
| 256 | — |
| 257 | 93 |
| 258 | 100 |
| 259 | — |
| 260 | 93 |
| 261 | — |
| 262 | — |
| 263 | — |
| 264 | — |
| 265 | — |
| 266 | — |
| 267 | — |
| 268 | — |
| 269 | — |

EXAMPLE 12

Boll Weevil

Five adult boll weevils (*Anthonomus grandis*) were placed into each of a series of 9-ounce cups. The test procedure employed was then otherwise the same as in Example 8 with three cups per treatment. Mortality readings were taken 48 hours after treatment. The results are tabulated below.

| Compound | % Mort. |
| --- | --- |
| 1 | 87 |
| 2 | 66 |
| 3 | 20 |
| 4 | 100 |
| 5 | 80 |
| 6 | — |
| 7 | 100 |
| 8 | — |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 22 | 93 |
| 23 | 100 |
| 24 | 100 |
| 25 | — |
| 26 | — |
| 27 | — |
| 28 | — |
| 29 | 100 |
| 30 | 100 |
| 31 | 100 |
| 32 | — |
| 33 | — |
| 34 | 100 |
| 35 | — |
| 36 | 87 |
| 37 | 100 |
| 38 | 73 |
| 39 | 87 |
| 40 | 100 |
| 41 | 100 |
| 42 | 100 |
| 43 | 100 |
| 44 | 93 |
| 45 | 93 |
| 46 | 93 |
| 47 | 100 |
| 48 | 80 |
| 49 | 67 |
| 50 | 80 |
| 51 | 93 |
| 52 | — |
| 53 | — |
| 54 | 100 |
| 55 | — |
| 56 | — |
| 57 | 53 |
| 58 | — |
| 59 | 100 |
| 60 | — |
| 61 | 100 |
| 62 | 100 |
| 63 | 100 |
| 64 | 100 |
| 65 | — |
| 66 | 100 |
| 67 | 100 |
| 68 | 100 |
| 69 | 93 |
| 70 | 53 |
| 71 | — |
| 72 | 40 |
| 73 | 87 |
| 74 | 100 |
| 75 | 60 |
| 76 | 93 |
| 77 | 100 |
| 78 | 100 |
| 79 | 100 |
| 80 | — |
| 81 | 100 |
| 82 | 100 |
| 83 | 100 |
| 84 | 100 |
| 85 | 80 |
| 86 | — |
| 87 | 100 |
| 88 | 100 |
| 89 | 100 |
| 90[1] | — |
| 91 | 93 |
| 92 | 100 |
| 93 | 100 |
| 94 | 100 |
| 95 | 100 |
| 96 | 73 |
| 97 | 67 |
| 98 | 100 |
| 99 | 100 |
| 100 | 100 |
| 101 | 100 |
| 102 | 40 |
| 103 | — |
| 104 | — |
| 105 | 100 |
| 106 | 100 |
| 107 | 100 |
| 108 | 100 |
| 109 | — |
| 110 | 100 |
| 111 | 100 |
| 112 | 100 |
| 113 | 7 |
| 114 | — |
| 115 | — |
| 116 | — |
| 117 | — |
| 118 | — |
| 119 | — |
| 120 | — |
| 121 | — |
| 122 | 67 |
| 123 | — |
| 124 | — |
| 125 | — |
| 126 | — |
| 127 | — |
| 128 | — |
| 129 | — |
| 130 | — |
| 131 | — |
| 132 | — |
| 133 | 100 |
| 134 | 93 |
| 135 | — |
| 136 | — |
| 137 | 93 |
| 138 | 100 |
| 139 | 47 |
| 140 | 93 |
| 141 | 93 |
| 142 | — |
| 143 | 100 |
| 144 | 100 |
| 145 | — |
| 146 | 60 |
| 147 | 93 |
| 148 | 67 |
| 149 | 0 |
| 150 | — |

-continued

| Compound | % Mort. |
|---|---|
| 151 | — |
| 152 | — |
| 153 | — |
| 154 | — |
| 155 | — |
| 156 | — |
| 157 | — |
| 158 | — |
| 159 | — |
| 160 | 33 |
| 161 | — |
| 162 | — |
| 163 | 33 |
| 164 | 73 |
| 165 | 100 |
| 166 | 80 |
| 167 | 13 |
| 168 | 93 |
| 169 | 87 |
| 170 | 100 |
| 171 | — |
| 172 | — |
| 173 | 20 |
| 174 | — |
| 175 | — |
| 176 | 100 |
| 177 | 100 |
| 178 | 73 |
| 179 | — |
| 180 | — |
| 181 | 100 |
| 182 | 87 |
| 183 | 100 |
| 184 | — |
| 185 | 87 |
| 186 | 73 |
| 187 | — |
| 188 | — |
| 189 | 100 |
| 190 | 93 |
| 191 | 100 |
| 192 | 100 |
| 193 | 100 |
| 194 | 60 |
| 195 | — |
| 196 | — |
| 197 | — |
| 198 | — |
| 199 | — |
| 200 | — |
| 201 | — |
| 202 | 100 |
| 203 | — |
| 204 | 100 |
| 205 | 100 |
| 206 | 100 |
| 207 | 87 |
| 208 | 100 |
| 209 | 100 |
| 210 | 93 |
| 211 | 100 |
| 212 | 100 |
| 213 | — |
| 214 | — |
| 215 | — |
| 216 | 100 |
| 217 | — |
| 218 | — |
| 219 | — |
| 220 | — |
| 221 | — |
| 222 | — |
| 223 | — |
| 224 | — |
| 225 | — |
| 226 | — |
| 227 | 87 |
| 228 | — |
| 229 | — |
| 230 | — |
| 231 | — |
| 232 | — |
| 233 | — |
| 234 | — |
| 235 | 33 |
| 236 | 80 |
| 237 | — |
| 238 | — |
| 239 | — |
| 240 | 93 |
| 241 | — |
| 242 | 100 |
| 243 | — |
| 244 | — |
| 245 | 27 |
| 246 | — |
| 247 | — |
| 248 | — |
| 249 | — |
| 250 | — |
| 251 | — |
| 252 | 100 |
| 253 | 100 |
| 254 | 100 |
| 255 | 93 |
| 256 | 100 |
| 257 | 87 |
| 258 | 93 |
| 259 | — |
| 260 | — |
| 261 | — |
| 262 | 20 |
| 263 | — |
| 264 | — |
| 265 | — |
| 266 | — |
| 267 | — |
| 268 | — |
| 269 | — |

What is claimed is:

1. A compound of the formula

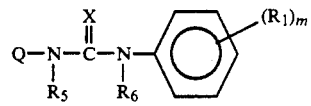

wherein:

Q is

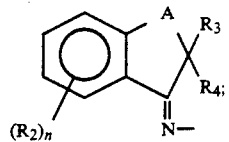

A is O, $S(O)_q$ or $NR_7$;

$R_1$ and $R_2$ are independently $R_8$, halogen, CN, $NO_2$, $N_3$, SCN, $OR_8$, $SR_8$, $SOR_8$, $SO_2R_8$, $NR_8R_9$, $C(O)R_8$, $CO_2R_8$, $C(O)NR_8R_9$, $OC(O)R_8$, $OCO_2R_8$, $OC(O)NR_8R_9$, $NR_9C(O)R_8$, $NR_9C(O)NR_8R_9$, $OSO_2R_8$, $NR_9SO_2R_8$, or when m is 2, $R_1$ is optionally taken together to form a 5 or 6 membered fused ring as $OCH_2O$, $OCH_2CH_2O$ or $CH_2CH_2O$ each of which is optionally substituted with 1 to 4 halogen atoms or 1 to 2 methyl groups, or when n is 2, $R_2$ is optionally taken together to form a 5 or 6 membered fused ring as $OCH_2O$, $OCH_2CH_2O$ or $CH_2CH_2O$ each of which can be substituted 1 to 4 halogens or 1 to 2 methyl groups;

$R_3$ is H, $C_1$-$C_6$ alkyl, $C_1$-$C_6$ haloalkyl, $C_4$-$C_6$ alkylcycloalkyl, $C_2$-$C_6$ alkenyl, $C_2$-$C_6$ haloalkenyl, $C_2$-$C_6$ alkynyl, $C_2$-$C_6$ haloalkynyl, $C_2$-$C_6$ alkoxyalkyl, $C_2$-$C_6$ cyanoalkyl, $C_3$-$C_8$ alkoxycarbonylakyl, $OR_8$, $S(O)_qR_8$, $NR_8R_9$, CN, $CO_2R_8$, $C(O)R_8$, $C(O)NR_8R_9$, $C(S)NR_8R_9$, $C(S)R_8$, $C(S)SR_8$, phenyl optionally substituted with $(R_{10})_p$ or benzyl optionally substituted with 1 to 3 substituents independently selected from W or $R_3$ is $C_3$-$C_6$ cycloalkyl optionally substituted with 1 to 2 halogens or 1 to 2 $CH_3$;

$R_4$ is H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_2$-$C_6$ alkoxyalkyl, $C_2$-$C_6$ cyanoalkyl, phenyl optionally substituted with $(R_{10})_p$ or benzyl optionally substituted with 1 to 3 substituents independently selected from W;

$R_5$ and $R_6$ are independently H, $C_1$-$C_{22}$ alkyl, $C_2$-$C_{22}$ alkoxyalkyl, $C_2$-$C_{22}$ alkylcarbonyl, $C_2$-$C_{22}$ alkoxycarbonyl, $C_2$-$C_{22}$ haloalkyl carbonyl, $C_2$-$C_{22}$ haloalkoxycarbony, $SR_{11}$, CHO, $C_1$-$C_4$ alkylsulfonyl, phenylsulfonyl optionally substituted with 1 to 3 substituents independently selected from W; $C_7$-$C_{15}$ phenoxycarbonyl optionally substituted with 1 to 3 substituents selected from W; $C_7$-$C_{15}$ phenylcarbonyl optionally substituted with 1 to 3 substituents independently selected from W; C(O)-$CO_2C_1$ to $C_4$ alkyl, $C_8$-$C_{12}$ benzyloxycarbonyl optionally substituted with 1 to 3 substituents independently selected from W; or $R_5$ and $R_6$ are independently phenyl optionally substituted with 1 to 3 substituents independently selected from W, or benzyl optionally substituted with 1 to 3 substituents independently selected from W;

$R_7$ is H, $C_1$-$C_4$ alkyl or phenyl optionally substituted with W; $SR_8$, $SOR_8$, $SO_2R_8$, $C(O)R_8$, $CO_2R_8$, $C(O)NR_8R_9$, $C(S)NR_8R_9$, $C(S)R_8$, $C(S)OR_8$, $P(O)(OR_8)_2$, $P(S)(OR_8)_2$, $P(O)(R_3)OR_8$ or $P(O)(R_8)SR_8$; provided that when $R_7$ is other than $COR_8$, $C(O)NR_8R_9$ or $C(S)NR_8R_9$ then $R_8$ is other than H;

$R_8$ is H, $C_1$-$C_6$ alkyl, $C_1$-$C_6$ haloalkyl, $C_4$-$C_7$ cycloalkylalkyl $C_2$-$C_6$ alkenyl, $C_2$-$C_6$ haloalkenyl, $C_2$-$C_6$ alkynyl, $C_2$-$C_6$ haloalkynyl, $C_2$-$C_6$ alkoxyalkyl, $C_2$-$C_6$ alkylthioalkyl, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, phenyl optionally substituted with 1 to 3 substituents independently selected from W or benzyl optionally substituted with 1 to 3 substituents independently selected from W;

$R_9$ is H, $C_1$-$C_4$ alkyl, $C_2$-$C_4$ alkenyl, $C_2$-$C_4$ alkynyl, or $R_8$ and $R_9$ is optionally taken together as $(CH_2)_4$, $(CH_2)_5$ or $(CH_2CH_2OCH_2CH_2)$;

$R_{10}$ is $R_8$, halogen, CN, $NO_2$, $N_3$, SCN, $OR_8$, $SR_8$, $SOR_8$, $SO_2R_8$, $NR_8R_9$, $COR_8$, $CO_2R_8$, $CONR_8R_9$, $SO_2NR_8R_9$, $OC(O)R_8$, $OCO_2R_8$, $OC(O)NR_8R_9$, $NR_9C(O)R_8$, $NR_9C(O)NR_8R_9$, $OSO_2R_8$, $NR_9SO_2R_8$ or when p is 2, $R_{10}$ is optionally taken together to form a 5 or 6 membered fused ring as $OCH_2O$, $OCH_2CH_2O$ or $CH_2CH_2O$ each of which is optionally substituted with independently, 1 to 4 halogen atoms or 1 to 2 methyl groups;

$R_{11}$ is $C_1$-$C_{22}$ alkyl, $C_1$-$C_{22}$ haloalkyl, phenyl optionally substituted with 1 to 3 substituents independently selected from W, or $R_{11}$ is $NR_{12}C(O)R_{13}$, $NR_{12}S(O)_aR_{13}$, $C(O)R_{13}$, $NR_{12}R_{16}$, $SR_{14}$,

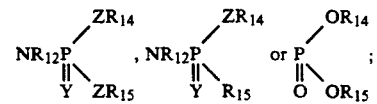

$R_{12}$ and $R_{16}$ are independently selected from $C_1$-$C_6$ alkyl, $C_1$-$C_6$ haloalkyl, $C_3$-$C_6$ cycloalkyl, $C_4$-$C_7$ cylcoalkylalkyl, $C_2$-$C_6$ cyanoalkyl, $C_2$-$C_6$ alkoxyalkyl, $C_3$-$C_8$ alkoxycarbonylalkyl, $C_4$-$C_8$ dialkylaminocarbonylalkyl, phenyl optionally substituted by 1 to 2 substituents selected from W, benzyl optionally substituted by 1 to 2 substituents selected from W and phenethyl optionally substituted by 1 to 2 substituents selected from W, or $R_{12}$-$R_{16}$ is optionally taken together as $(CH_2)_4$, $(CH_2)_5$ or $(CH_2)_2O(CH_2)_2$, each ring optionally substituted with 1 to 2 $CH_3$;

$R_{13}$ is F, $C_1$-$C_{20}$ alkyl, $C_1$-$C_6$ haloalkyl, $C_2$-$C_8$ dialkylamino, piperidinyl, pyrrolidinyl, morpholinyl, phenyl optionally substituted with 1 to 3 substituents selected from W, or $R_{13}$ is $C_1$-$C_{20}$ alkoxy $C_1$-$C_6$ haloalkoxy or $C_1$-$C_4$ alkoxy substituted with cyano, nitro, $C_1$-$C_4$ alkoxy, $C_4$-$C_8$ alkoxyalkoxy, $C_1$-$C_2$ alkylthio, $C_2$-$C_3$ alkoxycarbonyl, $C_3$-$C_5$ dialkylaminocarbonyl or phenyl optionally substituted with 1 to 3 substituents independently selected from W, or $R_{13}$ is phenoxy optionally substituted with 1 to 3 substituents selected from W;

$R_{14}$ and $R_{15}$ are independently selected from $C_1$-$C_4$ alkyl, $C_2$-$C_4$ haloalkyl, phenyl optionally substituted with 1 to 3 substituents independently selected from W or $R_{14}$ and $R_{15}$ is optionally taken together as $(CH_2)_2$, $(CH_2)_3$ or $CH_2C(CH_3)_2CH_2$;

W is halogen, CN, $NO_2$, $C_1$-$C_2$ alkyl, $C_1$-$C_2$ haloalkyl, $C_1$-$C_2$ alkoxy, $C_1$-$C_2$ haloalkoxy, $C_1$-$C_2$ alkylthio, $C_1$-$C_2$ haloalkylthio, $C_1$-$C_2$ alkylsulfonyl or $C_1$-$C_2$ haloalkylsulfonyl;

m is 1 to 5;
n is 1 to 4;
q is 0 to 2;
p is 1 to 3;
a is 0 to 2;
X is O or S;
Y is O or S; and
Z is O or S.

2. A compound according to claim 1 wherein: when $R_3$ or $R_4$ is H and A is oxygen then the remaining $R_3$ or $R_4$ is other than phenyl or phenyl optionally substituted with W.

3. A compound according to claim 1 wherein:

$R_1$, $R_2$ and $R_{10}$ are $R_8$, halogen, CN, $NO_2$, $OR_8$, $SR_8$, $SOR_8$, $SO_2R_8$, $NR_8R_9$, $CO_2R_8$, $SO_2NR_8R_9$, or when m, n or q is 2, then $R_1$, $R_2$ or $R_{10}$ respectively is optionally taken together to form a 5 or 6 membered fused ring as $OCH_2O$, $OCH_2CH_2O$ or $CH_2CH_2O$ each of which is optionally substituted with 1 to 4 halogens or 1 to 2 methyl groups;

$R_8$ is H, $C_1$-$C_6$ alkyl, $C_1$-$C_6$ haloalkyl, $C_3$-$C_6$ cycloalkylalkyl, $C_3$-$C_6$ halocycloalkylalkyl, $C_2$-$C_6$ alkenyl, $C_2$-$C_6$ haloalkenyl, $C_2$-$C_6$ alkynyl, $C_3$-$C_6$ cycloalkyl, phenyl optionally substituted with 1 to 2 substituents independently selected from W or benzyl optionally substituted with 1 to 2 substituents independently selected from W;

$R_5$ and $R_6$ are independently H, $C_1$-$C_3$ alkyl, $C_2$-$C_4$ alkylcarbonyl, $C_2$-$C_4$ alkoxycarbonyl, CHO, $SR_{11}$, phenyl optionally substituted with 1 to 2 substituents independently selected from W, or benzyl optionally substituted with 1 to 2 substituents independently selected from W;

$R_{11}$ is $C_1-C_3$ alkyl, phenyl optionally substituted with 1 to 2 substituents independently selected from W, $NR_{12}C(O)R_{13}$, $NR_{12}S(O)_aR_{13}$, $C(O)R_{13}$, $NR_{12}R_{16}$,

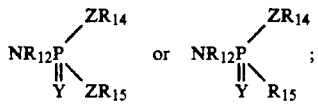

$R_{12}$ and $R_{16}$ are independently selected from $C_1-C_6$ alkyl, $C_1-C_6$ haloalkyl, $C_5-C_6$ cycloalkyl, $C_3-C_8$ alkoxycarbonyl- alkyl, phenyl, benzyl and phenethyl or each phenyl, benzyl and phenethyl optionally substituted with 1 to 2 substituents independently selected from W, or $R_{12}$ and $R_{16}$ can be taken together as $(CH_2)_4$, $(CH_2)_5$ or $(CH_2)_2O(CH_2)_2$;

$R_{14}$ and $R_{15}$ are independently selected from $C_1$ to $C_3$ alkyl or phenyl;

m is 1 to 2;
n is 1 to 2;
p is 1 to 2;
q is 0; and
a is 2.

4. A compound according to claim 3 wherein:
$R_3$ is H, $C_1-C_4$ alkyl, $C_1-C_4$ haloalkyl, $C_2-C_4$ alkenyl, $C_2-C_4$ alkynyl, CN, phenyl optionally substituted with $(R_{10})_p$ or benzyl optionally substituted with 1 to 2 substituents independently selected from W;
$R_4$ is H, $C_1-C_3$ alkyl, $C_3-C_4$ alkenyl or $C_3-C_4$ alkynyl;
$R_5$ is H, Me, $CO_2Me$, $CO_2Et$, $SR_{11}$ or phenyl optionally substituted with 1 to 2 substituents independently selected from W;
$R_6$ is H, Me, C(O)Me, $CO_2Me$ or $SR_{11}$;
$R_{11}$ is $C_1-C_3$ alkyl, $NR_{12}C(O)R_{13}$, $NR_{12}S(O)_aR_{13}$, $C(O)R_{13}$, or phenyl optionally substituted with Cl, $NO_2$ or $CH_3$;
$R_{12}$ is $C_1-C_4$ alkyl or phenyl optionally substituted with Cl or CH3;
$R_{13}$ is $C_1-C_{12}$ alkyl, $C_1-C_{12}$ alkoxy, $C_1-C_6$ haloalkyl, dimethylamino, phenyl optionally substituted with Cl or CH3, or $R_{13}$ is $C_1-C_4$ alkoxy substituted with $C_2-C_4$ alkoxy or 1 to 6 halogens;
$R_7$ is H, $C_1-C_4$ alkyl, $C_2-C_4$ alkenyl, $C_2-C_4$ alkynyl, $C_2-C_4$ alkylcarbonyl, $C_2-C_4$ alkoxycarbonyl or $C_1-C_4$ alkylsulfonyl.

5. A compound according to claim 4 wherein:
$R_1$ and $R_2$ are independently selected from F, Cl, Br, CN, $NO_2$, OMe, $CF_3$, $OCF_2H$, $OCF_2CF_2H$, SMe, $SO_2Me$, $SCF_2H$ or when m or n is 2 $R_1$ or $R_2$ respectively is optionally taken together as $CH_2C(CH_3)_2O$ or $CF_2CF_2O$;
$R_3$ is $C_1$ to $C_4$ alkyl, allyl, propargyl, or phenyl optionally substituted with F, Cl, Br, $CF_3$, $OCF_2H$, $OCF_3$, $SCF_2H$, CN, $NO_2$, $CH_3$, OMe or $CO_2Me$;
$R_4$ is H or CH3;
$R_5$ is H, $CH_3$ $CO_2CH_3$, $CO_2Et$, or phenyl optionally substituted with F or Cl;
$R_6$ is H, $CH_3$, $C(O)CH_3$ or $CO_2CH_3$; and
A is O.

6. A compound according to claim 5:
2-[6-chloro-2,3-dihydro-2-methyl-2-(2-propenyl)-3-benzo-furanylidene]-N-[4-(trifluoromethoxy)phenyl]hydrazine carboxamide.

7. An arthropodicidal composition comprising an arthropodicidally effective amount of a compound according to claim 1 and a carrier therefor.

8. A method for controlling arthropods comprising applying to them or to their environment an arthropodicidally effective amount of a compound according to claim 1.

* * * * *